US009128096B2

(12) United States Patent
Buggy et al.

(10) Patent No.: US 9,128,096 B2
(45) Date of Patent: *Sep. 8, 2015

(54) METHODS FOR DETERMINING CANCER RESISTANCE TO HISTONE DEACETYLASE INHIBITORS

(75) Inventors: Joseph J. Buggy, Mountain View, CA (US); Sriram Balasubramanian, San Carlos, CA (US)

(73) Assignee: PHARMACYCLICS, INC., Sunnyvale, CA (US)

( * ) Notice: Subject to any disclaimer, the term of this patent is extended or adjusted under 35 U.S.C. 154(b) by 1255 days.

This patent is subject to a terminal disclaimer.

(21) Appl. No.: 12/898,314

(22) Filed: Oct. 5, 2010

(65) Prior Publication Data

US 2011/0053164 A1 Mar. 3, 2011

Related U.S. Application Data

(63) Continuation of application No. 12/022,977, filed on Jan. 30, 2008, now Pat. No. 7,838,234.

(60) Provisional application No. 60/911,855, filed on Apr. 13, 2007, provisional application No. 60/887,318, filed on Jan. 30, 2007.

(51) Int. Cl.

| | |
|---|---|
| ***C07H 21/04*** | (2006.01) |
| ***C12N 15/11*** | (2006.01) |
| ***G01N 33/574*** | (2006.01) |
| ***C12N 5/09*** | (2010.01) |
| ***C12Q 1/68*** | (2006.01) |

(52) U.S. Cl.

CPC ........ *G01N 33/57492* (2013.01); *C12N 5/0693* (2013.01); *C12Q 1/6886* (2013.01); *G01N 33/57419* (2013.01); *C07H 21/04* (2013.01); *C12N 15/11* (2013.01); *C12N 2503/02* (2013.01); *C12Q 2600/106* (2013.01); *C12Q 2600/136* (2013.01); *G01N 2800/52* (2013.01)

(58) Field of Classification Search

None

See application file for complete search history.

(56) References Cited

U.S. PATENT DOCUMENTS

| | | | | |
|---|---|---|---|---|
| 4,999,378 | A | 3/1991 | Fujii et al. | |
| 5,254,731 | A | 10/1993 | Zimmer et al. | |
| 5,972,978 | A | 10/1999 | Andersen et al. | |
| 6,211,197 | B1 | 4/2001 | Belley et al. | |
| 6,960,685 | B2 | 11/2005 | Watkins et al. | |
| 7,247,426 | B2 | 7/2007 | Yakhini et al. | |
| 7,276,612 | B2 | 10/2007 | Verner et al. | |
| 7,420,089 | B2 | 9/2008 | Verner et al. | |
| 7,482,466 | B2 | 1/2009 | Verner et al. | |
| 7,517,988 | B2 | 4/2009 | Verner et al. | |
| 7,745,391 | B2 * | 6/2010 | Mintz et al. | 514/19.3 |
| 7,834,054 | B2 | 11/2010 | Verner et al. | |
| 7,838,234 | B2 | 11/2010 | Buggy et al. | |
| 8,026,371 | B2 | 9/2011 | Verner et al. | |
| 8,389,570 | B2 | 3/2013 | Verner et al. | |
| 8,779,171 | B2 | 7/2014 | Verner et al. | |
| 2003/0166026 | A1 | 9/2003 | Goodman | |
| 2004/0053908 | A1 | 3/2004 | Funahashi et al. | |
| 2004/0077726 | A1 | 4/2004 | Watkins et al. | |
| 2007/0293540 | A1 | 12/2007 | Verner et al. | |
| 2008/0233562 | A1 | 9/2008 | Sasakawa et al. | |
| 2012/0064032 | A1 | 3/2012 | Verner et al. | |
| 2013/0064880 | A1 | 3/2013 | Kloos et al. | |
| 2013/0142758 | A1 | 6/2013 | Verner et al. | |
| 2014/0301976 | A1 | 10/2014 | Verner et al. | |

FOREIGN PATENT DOCUMENTS

| | | | |
|---|---|---|---|
| CN | 1777675 | A | 5/2006 |
| DE | 2201968 | | 8/1973 |
| EP | 0084236 | A2 | 7/1983 |
| EP | 0394440 | A1 | 10/1990 |
| EP | 1400806 | A1 | 3/2004 |
| EP | 1426054 | A1 | 6/2004 |
| EP | 1595952 | A1 | 11/2005 |
| EP | 1611088 | B1 | 1/2006 |
| GB | 1381319 | A | 1/1975 |
| JP | 3-215470 | | 9/1991 |
| WO | WO-95-05358 | A1 | 2/1995 |
| WO | WO-00-20371 | A1 | 4/2000 |
| WO | WO-01-14331 | A2 | 3/2001 |

(Continued)

OTHER PUBLICATIONS

U.S. Appl. No. 13/744,265, filed Jan. 17, 2013, Verner et al.

Brzozowski, Z. et al., "Derivatives of 2-Mercapobenzenesulphonamide XI. Synthesis and Some Pharmacological Properties of 2- {2—[2-(3,4,5-Trimethoxybenzamido)Ethylthio]Benzenesulphonyl} Guanadines," Acta Poloniae Pharmaceutica-Drug Research 50(4-5):345-352 (1993).

Carter et al., Chemotherapy of Cancer, $2^{nd}$ ed., John Wiley & Sons, N.Y., N.Y. 1981, pp. 362-365.

Hines, J.W. and Stammer, C.H., "3-Hydroxyisoxazole-5-hydroxamic Acid," J. Med. Chem 20(7):965-967 (1977).

(Continued)

*Primary Examiner* — James Martinell

(74) *Attorney, Agent, or Firm* — Wilson Sonsini Goodrich & Rosati

(57) ABSTRACT

Described herein are methods and compositions for determining whether a particular cancer is resistant to or susceptible to a histone deacetylase inhibitor or to histone deacetylase inhibitors. The methods include analysis of the expression levels of at least four biomarker genes associated with response to a histone deacetylase inhibitor. Also described herein are methods and compositions for increasing the likelihood of a therapeutically effective treatment in a patient, comprising an analysis of the expression levels of at least four biomarker genes associated with response to a histone deacetylase inhibitor. Also described herein are isolated populations of nucleic acids derived from a cancer sensitive to or resistant to a histone deacetylase inhibitor. Further described are kits and indications that are optionally used in conjunction with the aforementioned methods and compositions.

8 Claims, 11 Drawing Sheets

(56) References Cited

FOREIGN PATENT DOCUMENTS

| | | | |
|---|---|---|---|
| WO | WO-01-38322 | A1 | 5/2001 |
| WO | WO-02-26703 | A1 | 4/2002 |
| WO | WO-02-30879 | A2 | 4/2002 |
| WO | WO-02-053775 | | 7/2002 |
| WO | WO-03-013493 | A1 | 2/2003 |
| WO | WO-03-066892 | | 8/2003 |
| WO | WO-03-070691 | A1 | 8/2003 |
| WO | WO-03066892 | | 8/2003 |
| WO | WO-2004-013130 | A1 | 2/2004 |
| WO | WO-2004-074478 | | 9/2004 |
| WO | WO-2004-092115 | A3 | 10/2004 |
| WO | WO-2005-059108 | A2 | 6/2005 |
| WO | WO-2008-095050 | | 8/2008 |

OTHER PUBLICATIONS

LaVoie, R., "Design and Synthesis of a Novel Class of Histone Deacetylase Inhibitors," Bioorg. Med. Chem. Ltrs. 11:2847-2850 (2001).

Uesato, S., "Novel Histone Deacetylase Inhibitors: N-Hydroxycarboxamides Possessing a Terminal Bicyclic Aryl Group," Bioorg. Med. Chem. Ltrs. 12:1347-1349 (2002).

Watanabe, S. et al., "Synthesis of 4-[1-(substituted pheny1)-2-oxo-pyrrolidin4-yl]methyloxybenzoic acids and related compounds, and their inhibitory capacities toward fatty-acid and sterol biosynthesis," Eur. J. Med. Chem. 29:675-686 (1994).

PCT/US2004/010549 Written Opinion dated Oct. 7, 2005.

PCT/US2004/010549 International Search Report dated Dec. 20, 2004.

CN200880006664.1 Office Action dated May 23, 2011.

Banwell, et al., "Antiproliferative signalling by 1,25(OH)2D3 in prostate and breast cancer is suppressed by a mechanism involving histone deacetylation." Recent Results Cancer Res.: 164:83-98 (2003).

De Schepper, et al. "Inhibition of Histone Deacetylases by chlamydocin Induces Apoptosis and Proteasome-Mediated Degradation of Survivin." The Journal of Pharmacology and Experimental Therapeutics, vol. 304, No. 2, pp. 881-888 (2003).

Kelly, et al., "Histone deacetylase inhibitors: from target to clinical trials." Expert Opin Investig Drugs. Dec.;11(12):1695-1713 (2002).

Mori et al., "FR235222, a fungal metabolite, is a novel immunosuppressant that inhibits mammalian histone deacetylase (HDAC). I. Taxonomy, fermentation, isolation and biological activities." J Antibiot (Tokyo). Feb.; 56(2):72-79 (2003).

U.S. Appl. No. 13/744,265 Office action mailed Jun. 10, 2013.

U.S. Appl. No. 10/818,755 Office action mailed Mar. 15, 2007.

U.S. Appl. No. 12/896,535 Office action mailed Mar. 8, 2011.

U.S. Appl. No. 13/209,147 Office Action mailed Apr. 18, 2012.

U.S. Appl. No. 13/744,265 Final Action dated Oct. 23, 2013.

U.S. Appl. No. 11/834,558 Office Action mailed Feb. 5, 2008.

Hardiman, "Microarray Platforms—Comparisons and Contrasts," Pharmacogenomics 5(5):487-50, (2004).

LePage, C. et al., "From gene profiling to diagnostic markers: IL-18 and FGF-2 complement CA125 as serum-based markers in epithelial ovarian cancer," Int. J. Cancer 118(7):1750-1758 (2006).

Natrajan, R. et al., "Array CGH profiling of favourable histology Wilms tumours reveals novel gains and losses associated with relapse," J. Pathol. 210(1):49-58 (2006).

Piekarz et al. "T-cell lymphoma as a model for the use of histone deacetylase inhibitors in cancer therapy: impact of depsipeptide on molecular markers, therapeutic targets, and mechanisms of resistance," Blood 103(12):4636-4643 (2004).

Sasakawa et al., "Marker genes to predict sensitivity to FK 228, a histone deacetylase inhibitor," Biochem. Pharmacol. 69(4):603-616 (2005).

EP 08728620 Supplementary Search Report mailed Aug. 24, 2010.

PCT/US08/52540 Search Report dated Jun. 17, 2008.

EP8728620 Examination Report dated Jan. 19, 2012.

EA200900927 Office Action dated Jul. 12, 2011.

Furumai et al. Potent histone deacetylase inhibitors built from trichostatin A and cyclic tetrapeptide antibiotics including trapoxin. PNAS. Jan. 2, 2001. 98(1):87-92.

Marks et al. Histone Deacetylase Inhibitors: Inducers of Differentiation or Apoptosis of Transformed Cells, Journal of the National Cancer Institute. 92(15):1210-1216. (Aug. 2, 2000).

U.S. Appl. No. 12/022,977 Office Action mailed Mar. 23, 2010.

U.S. Appl. No. 12/393,923 Office Action mailed Mar. 19, 2010.

U.S. Appl. No. 14/311,025 Office Action mailed Sep. 30, 2014.

Co-pending U.S. Appl. No. 14/671,384, filed Mar. 27, 2015.

* cited by examiner

SEQUENCE LISTING

```
<160> NUMBER OF SEQ ID NOS: 44

<210> SEQ ID NO 1
<211> LENGTH: 2376
<212> TYPE: DNA
<213> ORGANISM: Homo sapiens

<400> SEQUENCE: 1

tgaatagttt gctggtagca agacggatga agacctatat gggagattct ttatctctag      60

agctagcata tttacttgca tactttgttt cttttccaca tggatatttt actgctaaat     120

ggcagaggtg ggagggagat gtcacacagt accataaccc catattgaaa acaagaaacc     180

accagaaagt ttgcagctaa ggggcagggg attcagttcc tacgcccact cagcactaac     240

tacttgcggg cctggttgct tagaagctct acctctcttt cattatctgt aaaatagaaa     300

caatacttag gactttagtt ggaacatgag gattgaataa gatcacgcta ttcatgtgac     360

tttttatcgg ctagaacagc aacagacact gctgtgggtg agttacttag aaaagtttag     420

ttatcagtga ttagcccaaa aacacatcag tcaaaaatag aatccactgg atttttgtct     480

ctctttttag agacagggtc tcactgtcgc ccaggctgga gtacagtggc atgatcattg     540

ttcactgcag cctcaaattc ctgggctcaa gcaatcctcg cacctcagcc tcctgagtag     600

ccgggactat aggcacatgc cacctcacct ggcttgtgtg tgtgtgtgtg tgtgtgtgtg     660

tgtgtgtgtg tgtgtgtgta gagacaggat cttgatgtgt cgcctaggct ggtctcaaac     720

tcctggcctc aagtgatctt cccacctcag cctccaaaac tgttgggatt ataggcgtga     780

gccactgtgc ccagcctaac tgggttttta tgagaggaaa atagaaaatg ctcttctaga     840

agagagagaa caagagcaca aaataatctg gactcacaaa aattcagcaa gctccaagaa     900

agggggatgg agggaacgct ggcaaaaatt taaatgccat taggatattt agcaagttat     960

tactgtttgg taaaaatgca tcatcaccct gtgtgcaaaa tgcttgcaaa gtagtctaaa    1020

tgtctttgga gatgggtgtt ttactgcttt tttccaaaaa caaattgttt attatggttg    1080

cagaaatgca gccattacgg tcacataaat ttctaaaaag cctaccaaag gttgcaagca    1140

gtcttctgcc actgggcagg ccagcagttc agacccagcg aggttgccag gaacaaatcc    1200

aggaaatact gggaagaaca agacaagaga attacctaaa agagcaaaca attcaagtaa    1260

atcctgtagc tattaccact taaaatccgt agctcaagat tcctgtttca ccaccttata    1320

cacttaagca attatactta agccttttt tagtcctaag tgaagaacta catcagaatc     1380

aggataagta ttttgcctgg gaaatttggc tgcatatgaa tggagaagac atttacatcc    1440

tatgttctgg cactttctga aagatctaat taaacatgtt gatgtgccaa tttaatcaag    1500

atgagagatc cctgctggtg tcaccctcta gaacctgcac ttggtgtttt gactttccag    1560

aagaaaaaaa tgcaactttg gttagggggc agtggttgga tcacacagtt gtctttcgtt    1620

tcctaccaca gtaattcata tttaaatatg cttttagatt agtgtggata ctattgctgc    1680

tgtgttgcta cctgaccttt ttctgggggg ggtacctcag aaatgagcat ttgagggcaa    1740

gcgaaaaagc cctcttcatc ctccagaggc aacaaagagg cagcagaaat ggggaaagat    1800

tgtgagaggc agggcttggg tctagacctg gacttaggca agatatgttg ccctcaaccc    1860

tgagttttct tatatgtaaa aagggaaggt tgggctggac tagatgaggt caagatttgc    1920
```

-continued cattctggga ggctgatatt ccagagaatc aaaattaatc ctaaaccaaa gctttatggc 1980
tgctacagag acatgtcaca tttctgagac ttgtcaccaa gagtttgtcc ctcagacttt 2040
ggcgctgttg aatgcaaaga caaggatggc caccttctgg ttcttgcctg ttgtcctcag 2100
ctgagagcag tctcggtaaa ggtggcaaag attctgtgac ctcagaccgg ggaccaaatg 2160
cttgggagtc tgatggccgg gctgggccac cattctcata gctctcattc tgtttggagc 2220
aaccaaagga tttgtgtgaa gttatttgga aaaggacctt aactgagcag taatcttttt 2280
tctgtatatt tggaatgttt ttcattctga cctgttctgt cagtgattct actgaaaaac 2340
aatttaatca atataaaaat gttcaagcta tgcaac 2376

<210> SEQ ID NO 2
<211> LENGTH: 5310
<212> TYPE: DNA
<213> ORGANISM: Homo sapiens

<400> SEQUENCE: 2
ctccggcgcc cgctctgccc gccgctgggt ccgaccgcgc tcgccttcct tgcagccgcg 60
cctcggcccc atggacgccc tgtgcggttc cggggagctc ggctccaagt tctgggactc 120
caacctgtct gtgcacacag aaaacccgga cctcactccc tgcttccaga actccctgct 180
ggcctgggtg ccctgcatct acctgtgggt cgccctgccc tgctacttgc tctacctgcg 240
gcaccattgt cgtggctaca tcatcctctc ccacctgtcc aagctcaaga tggtcctggg 300
tgtcctgctg tggtgcgtct cctgggcgga cctttttttac tccttccatg gcctggtcca 360
tggccgggcc cctgcccctg ttttctttgt caccccccttg gtggtggggg tcaccatgct 420
gctggccacc ctgctgatac agtatgagcg gctgcagggc gtacagtctt cgggggtcct 480
cattatcttc tggttcctgt gtgtggtctg cgccatcgtc ccattccgct ccaagatcct 540
tttagccaag gcagagggtg agatctcaga ccccttccgc ttcaccacct tctacatcca 600
ctttgccctg gtactctcta ccctcatctt ggcctgcttc agggagaaac ctccattttt 660
ctccgcaaag aatgtcgacc ctaaccccta ccctgagacc agcgctggct ttctctcccg 720
cctgtttttc tggtggttca caaagatggc catctatggc taccggcatc ccctggagga 780
gaaggacctc tggtccctaa aggaagagga cagatcccag atggtggtgc agcagctgct 840
ggaggcatgg aggaagcagg aaaagcagac ggcacgacac aaggcttcag cagcacctgg 900
gaaaaatgcc tccggcgagg acgaggtgct gctgggtgcc cggcccaggc cccggaagcc 960
ctccttcctg aaggccctgc tggccacctt cggctccagc ttcctcatca gtgcctgctt 1020
caagcttatc caggacctgc tctccttcat caatccacag ctgctcagca tcctgatcag 1080
gtttatctcc aaccccatgg ccccctcctg gtggggcttc ctggtggctg ggctgatgtt 1140
cctgtgctcc atgatgcagt cgctgatctt acaacactat taccactaca tctttgtgac 1200
tggggtgaag tttcgtactg ggatcatggg tgtcatctac aggaaggctc tggttatcac 1260
caactcagtc aaacgtgcgt ccactgtggg ggaaattgtc aacctcatgt cagtggatgc 1320
ccagcgcttc atggaccttg ccccccttcct caatctgctg tggtcagcac ccctgcagat 1380
catcctggcg atctacttcc tctggcagaa cctaggtccc tctgtcctgg ctggagtcgc 1440
tttcatggtc ttgctgattc cactcaacgg agctgtggcc gtgaagatgc gcgccttcca 1500
ggtaaagcaa atgaaattga aggactcgcg catcaagctg atgagtgaga tcctgaacgg 1560
catcaaggtg ctgaagctgt acgcctggga gcccagcttc ctgaagcagg tggagggcat 1620
caggcagggt gagctccagc tgctgcgcac ggcggcctac ctccacacca caaccacctt 1680

-continued

```
cacctggatg tgcagcccct tcctggtgac cctgatcacc ctctgggtgt acgtgtacgt   1740
ggacccaaac aatgtgctgg acgccgagaa ggcctttgtg tctgtgtcct tgtttaatat   1800
cttaagactt cccctcaaca tgctgcccca gttaatcagc aacctgactc aggccagtgt   1860
gtctctgaaa cggatccagc aattcctgag ccaagaggaa cttgaccccc agagtgtgga   1920
aagaaagacc atctccccag gctatgccat caccatacac agtggcacct tcacctgggc   1980
ccaggacctg ccccccactc tgcacagcct agacatccag gtcccgaaag gggcactggt   2040
ggccgtggtg gggcctgtgg gctgtgggaa gtcctccctg gtgtctgccc tgctgggaga   2100
gatggagaag ctagaaggca aagtgcacat gaagggctcc gtggcctatg tgccccagca   2160
ggcatggatc cagaactgca ctcttcagga aaacgtgctt ttcggcaaag ccctgaaccc   2220
caagcgctac cagcagactc tggaggcctg tgccttgcta gctgacctgg agatgctgcc   2280
tggtggggat cagacagaga ttggagagaa gggcattaac ctgtctgggg gccagcggca   2340
gcgggtcagt ctggctcgag ctgtttacag tgatgccgat attttcttgc tggatgaccc   2400
actgtccgcg gtggactctc atgtggccaa gcacatcttt gaccacgtca tcgggccaga   2460
aggcgtgctg gcaggcaaga cgcgagtgct ggtgacgcac ggcattagct tcctgcccca   2520
gacagacttc atcattgtgc tagctgatgg acaggtgtct gagatgggcc cgtacccagc   2580
cctgctgcag cgcaacggct cctttgccaa ctttctctgc aactatgccc ccgatgagga   2640
ccaagggcac ctggaggaca gctggaccgc gttggaaggt gcagaggata aggaggcact   2700
gctgattgaa gacacactca gcaaccacac ggatctgaca gacaatgatc cagtcaccta   2760
tgtggtccag aagcagttta tgagacagct gagtgccctg tcctcagatg ggagagggaca   2820
gggtcggcct gtaccccgga ggcacctggg tccatcagag aaggtgcagg tgacagaggc   2880
gaaggcagat ggggcactga cccaggagga gaaagcagcc attggcactg tggagctcag   2940
tgtgttctgg gattatgcca aggccgtggg gctctgtacc acgctggcca tctgtctcct   3000
gtatgtgggt caaagtgcgg ctgccattgg agccaatgtg tggctcagtg cctggacaaa   3060
tgatgccatg gcagacagta gacagaacaa cacttccctg aggctgggcg tctatgctgc   3120
tttaggaatt ctgcaagggt tcttggtgat gctggcagcc atggccatgg cagcgggtgg   3180
catccaggct gcccgtgtgt tgcaccaggc actgctgcac aacaagatac gctcgccaca   3240
gtccttcttt gacaccacac catcaggccg catcctgaac tgcttctcca aggacatcta   3300
tgtcgttgat gaggttctgg cccctgtcat cctcatgctg ctcaattcct tcttcaacgc   3360
catctccact cttgtggtca tcatggccag cacgccgctc ttcactgtgg tcatcctgcc   3420
cctggctgtg ctctacacct tagtgcagcg cttctatgca gccacatcac ggcaactgaa   3480
gcggctggaa tcagtcagcc gctcacctat ctactcccac ttttcggaga cagtgactgg   3540
tgccagtgtc atccgggcct acaaccgcag ccgggatttt gagatcatca gtgatactaa   3600
ggtggatgcc aaccagagaa gctgctaccc ctacatcatc tccaaccggt cagaagccgc   3660
ctccctcgct ccctgctcct ccaggaattc ccagcaggct ctctggtgtt cagggtcctt   3720
gtccctcctt tcccctaagc agaaaactgg ccctgccctg cccctgcccc atttcctcct   3780
catctgatcc cccataggcg gctgagcatc ggagtggagt tcgtggggaa ctgcgtggtg   3840
ctctttgctg cactatttgc cgtcatcggg aggagcagcc tgaacccggg gctggtgggc   3900
ctttctgtgt cctactcctt gcaggtgaca tttgctctga actggatgat acgaatgatg   3960
tcagatttgg aatctaacat cgtggctgtg gagagggtca aggagtactc caagacagag   4020
```

-continued acagaggcgc cctgggtggt ggaaggcagc cgccctcccg aaggttggcc cccacgtggg 4080
gaggtggagt tccggaatta ttctgtgcgc taccggccgg gcctagacct ggtgctgaga 4140
gacctgagtc tgcatgtgca cggtggcgag aaggtgggga tcgtgggccg cactggggct 4200
ggcaagtctt ccatgaccct ttgcctgttc cgcatcctgg aggcggcaaa gggtgaaatc 4260
cgcattgatg gcctcaatgt ggcagacatc ggcctccatg acctgcgctc tcagctgacc 4320
atcatcccgc aggaccccat cctgttctcg gggaccctgc gcatgaacct ggaccccttc 4380
ggcagctact cagaggagga catttggtgg gctttggagc tgtcccacct gcacacgttt 4440
gtgagctccc agccggcagg cctggacttc cagtgctcag agggcgggga gaatctcagc 4500
gtgggccaga ggcagctcgt gtgcctggcc cgagccctgc tccgcaagag ccgcatcctg 4560
gttttagacg aggccacagc tgccatcgac ctggagactg acaacctcat ccaggctacc 4620
atccgcaccc agtttgatac ctgcactgtc ctgaccatcg cacaccggct taacactatc 4680
atggactaca ccagggtcct ggtcctggac aaaggagtag tagctgaatt tgattctcca 4740
gccaacctca ttgcagctag aggcatcttc tacgggatgg ccagagatgc tggacttgcc 4800
taaaatatat tcctgagatt tcctcctggc ctttcctggt tttcatcagg aaggaaatga 4860
caccaaatat gtccgcagaa tggacttgat agcaaacact gggggcacct taagattttg 4920
cacctgtaaa gtgccttaca gggtaactgt gctgaatgct ttagatgagg aaatgatccc 4980
caagtggtga atgacacgcc taaggtcaca gctagtttga gccagttaga ctagtccccc 5040
ggtctcccga ttcccaactg agtgttattt gcacactgca ctgttttcaa ataacgattt 5100
tatgaaatga cctctgtcct ccctctgatt tttcatattt tcctaaagtt tcgtttctgt 5160
tttttaataa aaagcttttt cctcctggaa cagaagacag ctgctgggtc aggccacccc 5220
taggaactca gtcctgtact ctggggtgct gcctgaatcc attaaaaatg ggagtactga 5280
tgaaataaaa ctacatggtc aacagtaaaa 5310

<210> SEQ ID NO 3
<211> LENGTH: 5490
<212> TYPE: DNA
<213> ORGANISM: Homo sapiens

<400> SEQUENCE: 3
gtgggggcca ggcagcacag atgaagcatt tacctatcta ggtaagtcag gaggagctca 60
aaaggagaag aaaacagtag gaggcagggg aagcagcctc tgtctccatc tctgcccttt 120
gaaacaaaag ggtatttctt ttctctcttc agcccccaac ccagtggagg cccggcttgg 180
gacattgttc acttcccctc gcttcccctc tagaagcccc ctttgccatc cctgcacctt 240
gtttcgggtg atgcccgaga gggagctgtg gccagcgggg actggctcag aacccgtgac 300
ccgtgtcggc agctgtgaca gcatgatgag cagcacctcc acccgctctg gatctagtga 360
tagcagctac gacttcctgt ccactgaaga gaaggagtgt ctgctcttcc tggaggagac 420
cattggctca ctggacacgg aggctgacag cggactgtcc actgacgagt ctgagccagc 480
cacaactccc agaggtttcc gagcactgcc cataacccaa cccactcccc ggggaggtcc 540
agaggagacc atcactcagc aaggacgaac gccaaggaca gtaactgagt ccagctcatc 600
ccaccctcct gagccccagg gcctaggcct caggtctggc tcctacagcc tccctaggaa 660
tatccacatt gccagaagcc agaacttcag gaaaagcacc acccaggcta gcagtcacaa 720
ccctggagaa ccggggaggc ttgcgccaga gcctgagaaa gaacaggtca gccagagcag 780
ccaacccagg caggcacctg ccagccccca ggaggctgcc cttgacttgg acgtggtgct 840

-continued

```
catccctccg ccagaagctt tccgggacac ccagccagag cagtgtaggg aagccagcct    900
gcccgagggg ccaggacagc agggccacac accccagctc cacacaccat ccagctccca    960
ggaaagagag cagactcctt cagaagccat gtcccaaaaa gccaaggaaa cagtctcaac   1020
caggtacaca caaccccagc ctcctcctgc agggttgcct cagaatgcaa gagctgaaga   1080
tgctcccctc tcatcagggg aggacccaaa cagccgacta gctcccctca caacccctaa   1140
gccccggaag ctgccaccta atattgttct gaagagcagc cgaagcagtt tccacagtga   1200
cccccagcac tggctgtccc gccacactga ggctgcccct ggagattctg gcctgatctc   1260
ctgttcactg caagagcaga gaaaagcacg taaagaagct ctagagaagc tggggctacc   1320
ccaggatcaa gatgagcctg gactccactt aagtaagccc accagctcca tcagacccaa   1380
ggagacacgg gcccagcatc tgtccccagc tccaggtctg gctcagcctg cagctccagc   1440
ccaggcctca gcagctattc ctgctgctgg gaaggctctg gctcaagctc cggctccagc   1500
tccaggtcca gctcagggac ctttgccaat gaagtctcca gctccaggca atgttgcagc   1560
tagcaaatct atgccaattc ctatccctaa ggccccaagg gcaaacagtg ccctgactcc   1620
accgaagcca gagtcagggc tgactctcca ggagagcaac accccctggcc tgagacagat   1680
gaacttcaag tccaacactc tggagcgctc aggcgtggga ctgagcagct acctttcaac   1740
tgagaaagat gccagcccca aaaccagcac ttctctggga aagggctcct tcttggacaa   1800
gatctcgccc agtgtcttac gtaattctcg gccccgcccg gcctccctgg gcacggggaa   1860
agattttgca ggtatccagg taggcaagct ggctgacctg gagcaggagc agagctccaa   1920
gcgcctgtcc taccaaggac agagccgtga caagcttcct cgcccccccct gtgtcagtgt   1980
caagatctcc ccaaagggtg tccccaatga acacagaagg gaggccctga agaagctggg   2040
actgttgaag gagtagactc tgcgaccagt acagaccctg tcctggctga acaagaagag   2100
acacatgctc cacttgggag cctttgccac cacgcaactc agggctcaag atgaatggga   2160
gggagagatt tgagtccaag catacattta tattcagtgt tgtgccattg agttcccatg   2220
tggatcattc tgaaggtgat ctccacaaga gggtgtgtgt gtgtgtgttt ggtgtgtgtg   2280
tggagggggg gccgctggat acatcactga agctattgat ataacacaat gagtcactgt   2340
tcagaatttt gctcttgtta gatgttttct tacattgggt agagtccagc ctagtgagag   2400
ctgagtgaag gggctggcca tgcctgagac aaaaagtcaa atgagacaat ggacgtgtca   2460
atgacttgaa aaaaagtcac atccagcaaa tgcagggtca catgaaatat gggcctcctg   2520
gaatccctac agtggatgga gactggctca taccttgcca gatccctctc tcagttccag   2580
ccttctggac aaggcctggg ctaagaggag ctgattcgtt atctcttcac ccactgccct   2640
ctcagtatca ccagtcccaa agacaggata cgtccctgta acccaatctc tcggttgatt   2700
gatagcagaa cagctcttgt tggtctgaga aggcaggata agtgaccaca tatttatgcc   2760
actacctcca ccagggagag tccttctcca caggcttgat aaattcaatc accaactgtg   2820
ctgtcgtccc tgactctgct actcccgttc ttcctgcttt cctgctccgt atctcagtct   2880
gcactgaccc cagggctggg ctgacatcaa gatgggagcc cagcccacgg gctttataaa   2940
cacccaagaa ccgtttcaga tcttctctgt gctgatgcag gtagttttaa atttttctca   3000
gttccagtga tagaaaaccc acacaataca tcctctgcca gtcttaatag aatatcagag   3060
gtaagagggg cctcagagaa gctctgacgc agtgctgctg gggaagggaa gtgactaacc   3120
ccgggtcagc ctgccattta gggaaagagc tgaggttctt acccttgttg catgctgcca   3180
```

-continued

```
cctctcctta gccagtgctc ttgtacatcc acacagcacc ctaaggagcc atagtcacca   3240
tcaaagactc aaccctaagg cccttcaaga tctcaaagtg ccttctgaag catcagagat   3300
taaatattgt tcaaactaat agttattgct gtggctttta attttatctt tggaagatag   3360
ctatatggta actcatcatt aaccagaaca cctctcccct caaattccgt gaccaagttg   3420
tgcagcttga gcaaatgccg aaagagggta ttatgggtgg gtggtgtggg cttgcaaata   3480
caagcttgga ggtgagacat ggccagacat gactcctgct tcccottagg aagtaaatct   3540
tacttatggt tgtgaactgc ttggagtcca ggatgcccag atgtgagggg cagatgaagg   3600
gaatgttgct ggaaaggtgc cttttaaggc tgctgagaat ttctggactg tgtcctgatg   3660
gacgcagcac catcaaagcc cagaatttct gaaaacggtg acaaggttaa cataaggaca   3720
acaaatactc caccctgtca tggtatgtga ggtgtgggtg tggcggtttc tgtgtacgtt   3780
tgctcataca cgcacatcca aaagcctgtg cctcattcct ggccatgggt gaggacttgg   3840
tctgtcacgg ctgatgagga ctcccacaac cggccaagtt atgtcttatt atacaccccc   3900
agaaagagag aaagctgcct tctggaggac tgattccaca tgctatattc agctgagttg   3960
atttctgtgt ctatttcaac ccataacctg aagaatgatc accttattcc ttattcatta   4020
attttcttga ttaataggga aacttgggaa tagctataaa gtaaaacttg ggtggaacct   4080
ggggccctgg catcacacaa gtgtgattag gatggtcaag gtcatcagga gtacagccta   4140
ttatattccc acatcctgag aaaggtcatt tctcccacac acgacaaagt cacagacatc   4200
ctgcacctgc cactaggcat cctcatccta ctgacatgcc catttctcca gttttcttaa   4260
tctgagactc ccttcccttg ttttttaaag ataccgtgct tctccacatc ctcatccttc   4320
aaggagcata ttttgctctt aggatggtct ttgggattca agaatagaat aataaatcca   4380
aacttggtca ttcccatttt gaagagatgc aagagggccc agtgaggaca tccgcctccc   4440
tgaaagtggt gctagacaga gctgaggtca ttgtatctgt gtatccacat aggatttctc   4500
ttaattcagc ttgaattgat ggggagggag gtaagagtag ggtcagagtt actcatccct   4560
tttcaaagaa ttgtgggtgg aagtttgtaa aggccattca tttgattttc aaaatcaaag   4620
cgacagctct acttccactt ggccttagat ctctgctata ccctgccata gccttgatgc   4680
cactgggcac aagccacctg ccaaatacag gagtggcctc tcccagcctg gcatgatagg   4740
ggggtctgtg ccctcagatg tgttgacagc tgctcttctg aattgccaca cctgtgctac   4800
acttggaatt ctgtgctctg actctgcagg gtaggaccac gtgccatctc acacagaggt   4860
caaccgatga gcccactcac tcgtacatgc cttcttccac agtgggaagc atgatctggc   4920
aggggccgcc ctgtaggctg gggatgggct gctgtgtgaa tgttgacgtt cgtttcatgg   4980
agaaagggga ggtgaaagat tgaagagcag gttcctgtca atgttctgag ttcgagctgg   5040
aggtgtagat tgaatagtct acatggtctg tgagtgtgtg agatgaaccc ttccatcctt   5100
tgacacctgg ttgtatgtgt aggctaagaa ggaaggaccc tcctgtcagt gtgcaaagct   5160
gtaatctcat ggactagagg agagggggcc aaggggatgg acaggagaag tcatgcagaa   5220
tctaagcagg aatgcagata gaacacatct aggctctttt ccccaggaga gtgatgatgg   5280
agcatataga tctggctcaa attcagcctc catcacttac cagtcaggaa ccctggcgat   5340
atcactttaa ctttctgaac ctcagagtct tcacctataa gacggggaaa ataataccac   5400
cctttcaaga ttgttgagat aaataagtga tataaaacat gtaaagctta gttctggcca   5460
cagtgtagct actcaataaa tgataatact                                     5490
```

<210> SEQ ID NO 4
<211> LENGTH: 1270
<212> TYPE: DNA
<213> ORGANISM: Homo sapiens

<400> SEQUENCE: 4
ctcctctccg cgcggggcgg gctccgcgcc acgtgactcc gcggccgggc cgggacgcga 60
cgggacgcgc tgggaccggc gtcgggggtc gcggggacca tgcagcggag cctccctgcc 120
cttcgctatc ctgacgctgg tgaacgcccc gtacaagcga ggattttact gcggggatga 180
ctccatccgg taccccctacc gtccagatac catcacccac gggctcatgg ctggggtcac 240
catcacggcc accgtcatcc ttgtctcggc cggggaagcc tacctggtgt acacagaccg 300
gctctattct cgctcggact tcaacaacta cgtggctgct gtatacaagg tgctggggac 360
cttcctgttt ggggctgccg tgagccagtc tctgacagac ctggccaagt acatgattgg 420
gcgtctgagg cccaacttcc tagccgtctg cgaccccgac tggagccggg tcaactgctc 480
ggtctatgtg cagctggaga aggtgtgcag gggaaaccct gctgatgtca ccgaggccag 540
gttgtctttc tactcgggac actcttcctt tgggatgtac tgcatggtgt tcttggcgct 600
gtatgtgcag gcacgactct gttggaagtg ggcacggctg ctgcgaccca cagtccagtt 660
cttcctggtg gcctttgccc tctacgtggg ctacacccgc gtgtctgatt acaaacacca 720
ctggagcgat gtccttgttg gcctcctgca gggggcactg gtggctgccc tcactgtctg 780
ctacatctca gacttcttca aagcccgacc cccacagcac tgtctgaagg aggaggagct 840
ggaacggaag cccagcctgt cactgacgtt gaccctgggc gaggctgacc acaaccacta 900 tggataccg cactcctcct cctgaggccg gaccccgccc aggcagggag ctgctgtgag 960
tccagctgag gcccacccag gtggtccctc cagccctggt taggcactga gggctctgga 1020
cgggctccag gaaccctggg ctgatgggag cagtgagcgg gctccgctgc cccctgccct 1080
gcactggacc aggagtctgg agatgcctgg gtagccctca gcatttggag gggaacctgt 1140
tcccgtcggt ccccaaatat ccccttcttt ttatggggtt aaggaaggga ccgagagatc 1200
agatagttgc tgttttgtaa aatgtaatgt atatgtggtt tttagtaaaa tagggcacct 1260
gtttcacaaa 1270

<210> SEQ ID NO 5
<211> LENGTH: 1500
<212> TYPE: DNA
<213> ORGANISM: Homo sapiens

<400> SEQUENCE: 5
gcgcgcctcg ccggcgcctc catcccggat ccttgctgca gcgtcagcgc cgccgcccgt 60
gcctttcctc ttcctcctcc tcctccttgg catccgcctc ttcttcctcc tgcgtcctcc 120
cccgctgcct ccgctgctcc cgacgcggag cccggagccc gcgccgagcc cctggcctcg 180
cggtgccatg ctgccccggc ggcggcgctg aaggatggcg acgccgctgc ctccgccctc 240
cccgcggcac ctgcggctgc tgcggctgct gctctccggc ctcgtcctcg gcgccgccct 300
gcgtggagcc gccgccggcc acccggatgt agccgcctgt cccgggagcc tggactgtgc 360
cctgaagagg cgggcaaggt gtcctcctgg tgcacatgcc tgtgggccct gccttcagcc 420
cttccaggag gaccagcaag ggctctgtgt gcccaggatg cgccggcctc caggcggggg 480
ccggccccag cccagactgg aagatgagat tgacttcctg gcccaggagc ttgcccggaa 540
ggagtctgga cactcaactc cgcccctacc caaggaccga cagcggctcc cggagcctgc 600 cacccctgggc ttctcggcac gggggcaggg gctggagctg ggcctcccct ccactccagg 660 aaccccacg cccacgcccc acacctccat gggctcccct gtgtcatccg acccggtgca 720
catgtcgccc ctggagcccc ggggagggca aggcgacggc ctcgcccttg tgctgatcct 780
ggcgttctgt gtggccggtg cagccgccct ctccgtagcc tccctctgct ggtgcaggct 840
gcatcgtgag atccgcctga ctcagaaggc cgactacgcc actgcgaagg cccctggctc 900
acctgcagct ccccggatct cgcctgggga ccaacggctg gcacagagcg cggagatgta 960
ccactaccag caccaacggc aacagatgct gtgcctggag cggcataaag agccacccaa 1020
ggagctggac acggcctcct cggatgagga gaatgaggac ggagacttca cggtgtacga 1080
gtgcccgggc ctggccccga ccggggaaat ggaggtgcgc aaccctctgt tcgaccacgc 1140
cgcactgtcc gcgcccctgc cggcccccag ctcaccgcct gcactgccat gacctggagg 1200
cagacagacg cccacctgct ccccgacctc gaggcccccg gggaggggca gggcctggag 1260
cttcccacta aaaacatgtt ttgatgctgt gtgcttttgg ctgggcctcg ggctccaggc 1320
cctgggaccc cttgccaggg agacccccga acctttgtgc caggacacct cctggtcccc 1380
tgcacctctc ctgttcggtt tagaccccca aactggaggg ggcatggaga accgtagagc 1440
gcaggaacgg gtgggtaatt ctagagacaa aagccaatta aagtccattt cagaaaaaaa 1500

<210> SEQ ID NO 6
<211> LENGTH: 4005
<212> TYPE: DNA
<213> ORGANISM: Homo sapiens

<400> SEQUENCE: 6
gggcaacagt ctgcccacct gtggacacca gatcctggga gctcctggtt agcaagtgag 60
atctctggga tgtcagtgag gctggttgaa gaccagaggt aaactgcaga ggtcaccacc 120
cccaccatgt cccaggtgat gtccagccca ctgctggcag gaggccatgc tgtcagcttg 180
gcgccttgtg atgagcccag gaggaccctg cacccagcac ccagccccag cctgccaccc 240
cagtgttctt actacaccac ggaaggctgg ggagcccagg ccctgatggc ccccgtgccc 300
tgcatggggc cccctggccg actccagcaa gccccacagg tggaggccaa agccacctgc 360
ttcctgccgt cccctggtga gaaggccttg gggaccccag aggaccttga ctcctacatt 420
gacttctcac tggagagcct caatcagatg atcctggaac tggaccccac cttccagctg 480
cttcccccag ggactggggg ctcccaggct gagctggccc agagcaccat gtcaatgaga 540
aagaaggagg aatctgaagc cttggacata aagtacatcg aggtgacctc cgccagatca 600
aggtgccacg attggcccca gcactgctcc agcccctctg tcaccccgcc cttcggctcc 660
cctcgcagtg gtggcctcct cctttccaga gacgtccccc gagagacacg aagcagcagt 720
gagagcctca tcttctctgg gaaccagggc agggggcacc agcgccctct gccccccctca 780 gagggtctct cccctcgacc cccaaattcc cccagcatct caatcccttg catggggagc 840
aaggcctcga gcccccatgg tttgggctcc ccgctggtgg cttctccaag actggagaag 900
cggctgggag gcctggcccc acagcggggc agcaggatct ctgtgctgtc agccagccca 960
gtgtctgatg tcagctatat gtttggaagc agccagtccc tcctgcactc cagcaactcc 1020
agccatcagt catcttccag atccttggaa agtccagcca actcttcctc cagcctccac 1080
agccttggct cagtgtccct gtgtacaaga cccagtgact tccaggctcc cagaaacccc 1140
accctaacca tgggccaacc cagaacaccc cactctccac cactggccaa agaacatgcc 1200
agcatctgcc ccccatccat caccaactcc atggtggaca tacccattgt gctgatcaac 1260

```
ggctgcccag aaccagggtc ttctccaccc cagcggaccc caggacacca gaactccgtt   1320
caacctggag ctgcttctcc cagcaacccc tgtccagcca ccaggagcaa cagccagacc   1380
ctgtcagatg ccccctttac cacatgccca gagggtcccg ccagggacat gcagcccacc   1440
atgaagttcg tgatggacac atctaaatac tggtttaagc caaacatcac ccgagagcaa   1500
gcaatcgagc tgctgaggaa ggaggagcca ggggcttttg tcataaggga cagctcttca   1560
taccgaggct ccttcggcct ggccctgaag gtgcaggagg ttcccgcgtc tgctcagaat   1620
cgaccaggtg aggacagcaa tgacctcatc cgacacttcc tcatcgagtc gtctgccaaa   1680
ggagtgcatc tcaaaggagc agatgaggag ccctactttg ggagcctctc tgccttcgtg   1740
tgccagcatt ccatcatggc cctggccctg ccctgcaaac tcaccatccc acagagagaa   1800
ctgggaggtg cagatggggc ctcggactct acagacagcc cagcctcctg ccagaagaaa   1860
tctgcgggct gccacaccct gtacctgagc tcagtgagcg tggagaccct gactggagcc   1920
ctggccgtgc agaaagccat ctccaccacc tttgagaggg acatcctccc cacgcccacc   1980
gtggtccact tcgaagtcac agagcagggc atcactctga ctgatgtcca gaggaaggtg   2040
tttttccggc gccattaccc actcaccacc ctccgcttct gtggtatgga ccctgagcaa   2100
cggaagtggc agaagtactg caaaccctcc tggatctttg ggtttgtggc caagagccag   2160
acagagcctc aggagaacgt atgccacctc tttgcggagt atgacatggt ccagccagcc   2220
tcgcaggtca tcggcctggt gactgctctg ctgcaggacg cagaaaggat gtaggggaga   2280
gactgcctgt gcacctaacc aacacctcca ggggctcgct aaggagcccc cctccacccc   2340
ctgaatgggt gtggcttgtg gccatattga cagaccaatc tatgggacta gggggattgg   2400
catcaagttg acacccttga acctgctatg gccttcagca gtcaccatca tccagacccc   2460
ccgggcctca gtttcctcaa tcatagaaga agaccaatag acaagatcag ctgttcttag   2520
atgctggtgg gcatttgaac atgctcctcc atgattctga agcatgcaca cctctgaaga   2580
cccctgcatg aaaataacct ccaaggaccc tctgacccca tcgacctggg ccctgcccac   2640
acaacagtct gagcaagaga cctgcagccc ctgtttcgtg gcagacagca ggtgcctggc   2700
ggtgacccac ggggctcctg gcttgcagct ggtgatggtc aagaactgac tacaaaacag   2760
gaatggatag actctatttc cttccatatc tgttcctctg ttccttttcc cactttctgg   2820
gtggcttttt gggtccaccc agccaggatg ctgcaggcca agctgggtgt ggtatttagg   2880
gcagctcagc agggggaact tgtccccatg gtcagaggag acccagctgt cctgcacccc   2940
cttgcagatg agtatcaccc catcttttct ttccacttgg tttttatttt tattttttt   3000
gagacagagt ctcactgtca cccaggctga actgcagtgg tgtgatctag gctcactgca   3060
acctccacct cccaggttca agcaattatc ctgcctcagg ctcccgagta gctgggatta   3120
caggcatgtg caactcaccc agctaatttt gtatttttag tagagacagg gtttcaccat   3180
gttggccagg ctggtcttga actcctgacc gcaggtaatc cacctgcttc ggcctcccaa   3240
agtgctggga ttacaggcgc aagccaccca gcccagcttc tttccattcc ttgataggcg   3300
agtattccaa agctggtatc gtagctgccc taatgttgca tattaggcgg cgggggcaga   3360
gataagggcc atctctctgt gattctgcct cagctcctgt cttgctgagc cctcccccaa   3420
cccacgctcc aacacacaca cacacacaca cacacacaca cacacacaca cacacacaca   3480
cacgcccctc tactgctatg tggcttcaac cagcctcaca gccacacggg ggaagcagag   3540
agtcaagaat gcaaagaggc cgcttcccta agaggcttgg aggagctggg ctctatccca   3600
```

-continued cacccacccc caccccaccc ccacccagcc tccagaagct ggaaccattt ctcccgcagg 3660
cctgagttcc taaggaaacc accctaccgg ggtggaaggg agggtcaggg aagaaaccca 3720
ctcttgctct acgaggagca agtgcctgcc ccctcccagc agccagccct gccaaagttg 3780
cattatcttt ggccaaggct gggcctgacg gttatgattt cagccctggg cctgcaggag 3840
aggctgagat cagcccaccc agccagtggt cgagcactgc cccgccgcca aagtctgcag 3900
aatgtgagat gaggttctca aggtcacagg ccccagtccc agcctggggg ctggcagagg 3960
cccccatata ctctgctaca gctcctatca tgaaaaataa aatgt 4005

<210> SEQ ID NO 7
<211> LENGTH: 1090
<212> TYPE: DNA
<213> ORGANISM: Homo sapiens

<400> SEQUENCE: 7
ctctgcttcc ttacagcacc cccacctgcc agagctgatc ctccctaggc cctgcctaac 60
cttgagttgg cccccaatcc ctctggctgc agaagtcccc ttacccccaa tgagaggagg 120
ggcaggacca gatcttttga gagctgaggg ttgagggcat tgagccaaca cacagatttg 180
tcgcctctgt ccccgaagac acctgcaccc tccatgcgga gccaagatgg ggaatggaac 240
tgaggaagat tataactttg tcttcaaggt ggtgctgatc ggcgaatcag gtgtggggaa 300
gaccaatcta ctctcccgat tcacgcgcaa tgagttcagc cacgacagcc gcaccaccat 360
cggggttgag ttctccaccc gcactgtgat gttgggcacc gctgctgtca aggctcagat 420
ctgggacaca gctggcctgg agcggtaccg agccatcacc tcggcgtact atcgtggtgc 480
agtgggggcc ctcctggtgt ttgacctaac caagcaccag acctatgctg tggtggagcg 540
atggctgaag gagctctatg accatgctga agccacgatc gtcgtcatgc tcgtgggtaa 600
caaaagtgac ctcagccagg cccgggaagt gcccactgag gaggcccgaa tgttcgctga 660
aaacaatgga ctgctcttcc tggagacctc agccctggac tctaccaatg ttgagctagc 720
ctttgagact gtcctgaaag aaatctttgc gaaggtgtcc aagcagagac agaacagcat 780
ccggaccaat gccatcactc tgggcagtgc ccaggctgga caggagcctg gccctgggga 840
gaagagggcc tgttgcatca gcctctgacc ttggccagca ccacctgccc ccactggctt 900
tttggtgccc cttgtcccca cttcagcccc aggacctttc cttgcccttt ggttccagat 960
atcagactgt tccctgttca cagcaccctc agggtcttaa ggtcttcatg ccctatcaca 1020
aatacctctt ttatctgtcc acccctcaca gactaggacc ctcaaataaa gctgttttat 1080
atcaaaaaaa 1090

<210> SEQ ID NO 8
<211> LENGTH: 4260
<212> TYPE: DNA
<213> ORGANISM: Homo sapiens

<400> SEQUENCE: 8
gcccagcctg cctggagaaa agtgtctgct cctagccaag atctcctcat cacaaaagta 60
atgtgggcca tggagtcagg ccacctcctc tgggctctgc tgttcatgca gtccttgtgg 120
cctcaactga ctgatggagc cactcgagtc tactacctgg gcatccggga tgtgcagtgg 180
aactatgctc ccaagggaag aaatgtcatc acgaaccagc ctctggacag tgacatagtg 240
gcttccagct tcttaaagtc tgacaagaac cggatagggg gaacctacaa gaagaccatc 300
tataaagaat acaaggatga ctcatacaca gatgaagtgg cccagcctgc ctggttgggc 360

-continued

```
ttcctggggc cagtgttgca ggctgaagtg ggggatgtca ttcttattca cctgaagaat    420
tttgccactc gtccctatac catccaccct catggtgtct tctacgagaa ggactctgaa    480
ggttccctat acccagatgg ctcctctggg ccactgaaag ctgatgactc tgttcccccg    540
gggggcagcc atatctacaa ctggaccatt ccagaaggcc atgcacccac cgatgctgac    600
ccagcgtgcc tcacctggat ctaccattct catgtagatg ctccacgaga cattgcaact    660
ggcctaattg ggcctctcat cacctgtaaa agaggagccc tggatgggaa ctcccctcct    720
caacgccagg atgtagacca tgatttcttc ctcctcttca gtgtggtaga tgagaacctc    780
agctggcatc tcaatgagaa cattgccact tactgctcag atcctgcttc agtggacaaa    840
gaagatgaga catttcagga gagcaatagg atgcatgcaa tcaatggctt tgtttttggg    900
aatttacctg agctgaacat gtgtgcacag aaacgtgtgg cctggcactt gtttggcatg    960
ggcaatgaaa ttgatgtcca cacagcattt ttccatggac agatgctgac tacccgtgga   1020
caccacactg atgtggctaa catctttcca gccacctttg tgactgctga gatggtgccc   1080
tgggaacctg gtacctggtt aattagctgc caagtgaaca gtcactttcg agatggcatg   1140
caggcactct acaaggtcaa gtcttgctcc atggcccctc ctgtggacct gctcacaggc   1200
aaagttcgac agtacttcat tgaggcccat gagattcaat gggactatgg cccgatgggg   1260
catgatggga gtactgggaa gaatttgaga gagccaggca gtatctcaga taagtttttc   1320
cagaagagct ccagccgaat tgggggcact tactggaaag tgcgatatga agcctttcaa   1380
gatgagacat tccaagagaa gatgcatttg gaggaagata ggcatcttgg aatcctgggg   1440
ccagtgatcc gggctgaggt gggtgacacc attcaggtgg tcttctacaa ccgtgcctcc   1500
cagccattca gcatgcagcc ccatggggtc ttttatgaga aagactatga aggcactgtg   1560
tacaatgatg gctcatctta ccctggcttg gttgccaagc cctttgagaa agtaacatac   1620
cgctggacag tccccccctca tgccggtccc actgctcagg atcctgcttg tctcacttgg   1680
atgtacttct ctgctgcaga tcccataaga gacacaaatt ctggcctggt gggcccgctg   1740
ctggtgtgca gggctggtgc cttgggtgca gatggcaagc agaaaggggt ggataaagaa   1800
ttctttcttc tcttcactgt gttggatgag aacaagagct ggtacagcaa tgccaatcaa   1860
gcagctgcta tgttggattt ccgactgctt tcagaggata ttgagggctt ccaagactcc   1920
aatcggatgc atgccattaa tgggtttctg ttctctaacc tgcccaggct ggacatgtgc   1980
aagggtgaca cagtggcctg gcacctgctc ggcctgggca cagagactga tgtgcatgga   2040
gtcatgttcc agggcaacac tgtgcagctt cagggcatga ggaagggtgc agctatgctc   2100
tttcctcata cctttgtcat ggccatcatg cagcctgaca accttgggac atttgagatt   2160
tattgccagg caggcagcca tcgagaagca gggatgaggg caatctataa tgtctcccag   2220
tgtcctggcc accaagccac ccctcgccaa cgctaccaag ctgcaagaat ctactatatc   2280
atggcagaag aagtagagtg ggactattgc cctgaccgga gctgggaacg ggaatggcac   2340
aaccagtctg agaaggacag ttatggttac attttcctga gcaacaagga tgggctcctg   2400
ggttccagat acaagaaagc tgtattcagg gaatacactg atggtacatt caggatccct   2460
cggccaagga ctggaccaga agaacacttg ggaatcttgg gtccacttat caaaggtgaa   2520
gttggtgata tcctgactgt ggtattcaag aataatgcca gccgccccta ctctgtgcat   2580
gctcatggag tgctagaatc tactactgtc tggccactgg ctgctgagcc tggtgaggtg   2640
gtcacttatc agtggaacat cccagagagg tctggccctg ggcccaatga ctctgcttgt   2700
```

-continued gtttcctgga tctattattc tgcagtggat cccatcaagg acatgtatag tggcctggtg 2760
gggcccttgg ctatctgcca aaagggcatc ctggagcccc atggaggacg gagtgacatg 2820
gatcgggaat ttgcattgtt gttcttgatt tttgatgaaa ataagtcttg gtatttggag 2880
gaaaatgtgg caacccatgg gtcccaggat ccaggcagta ttaacctaca ggatgaaact 2940
ttcttggaga gcaataaaat gcatgcaatc aatgggaaac tctatgccaa ccttaggggt 3000
cttaccatgt accaaggaga acgagtggcc tggtacatgc tggccatggg ccaagatgtg 3060
gatctacaca ccatccactt tcatgcagag agcttcctct atcggaatgg cgagaactac 3120
cgggcagatg tggtggatct gttcccaggg acttttgagg ttgtggagat ggtggccagc 3180
aaccctggga catggctgat gcactgccat gtgactgacc atgtccatgc tggcatggag 3240
accctcttca ctgtttttc tcgaacagaa cacttaagcc ctctcaccgt catcaccaaa 3300
gagactgaaa aagcagtgcc ccccagagac attgaagaag gcaatgtgaa gatgctgggc 3360
atgcagatcc ccataaagaa tgttgagatg ctggcctctg ttttggttgc cattagtgtc 3420
acccttctgc tcgttgttct ggctcttggt ggagtggttt ggtaccaaca tcgacagaga 3480
aagctacgac gcaataggag gtccatcctg gatgacagct tcaagcttct gtctttcaaa 3540
cagtaacatc tggagcctgg agatatcctc aggaagcaca tctgtagtgc actcccagca 3600
ggccatggac tagtcactaa ccccacactc aaaggggcat gggtggtgga gaagcagaag 3660
gagcaatcaa gcttatctgg atatttcttt ctttatttat tttacatgga aataatatga 3720
tttcactttt tctttagttt ctttgctcta cgtgggcacc tggcactaag ggagtacctt 3780
attatcctac atcgcaaatt tcaacagcta cattatattt ccttctgaca cttggaaggt 3840
attgaaattt ctagaaatgt atccttctca caaagtagag accaagagaa aaactcattg 3900
attgggtttc tacttctttc aaggactcag gaaatttcac tttgaactga ggccaagtga 3960
gctgttaaga taacccacac ttaaactaaa ggctaagaat ataggcttga tgggaaattg 4020
aaggtaggct gagtattggg aatccaaatt gaattttgat tctccttggc agtgaactac 4080
tttgaagaag tggtcaatgg gttgttgctg ccatgagcat gtacaacctc tggagctaga 4140
agctcctcag gaaagccagt tctccaagtt cttaacctgt ggcactgaaa ggaatgttga 4200
gttacctctt catgttttag acagcaaacc ctatccatta aagtacttgt tagaacactg 4260

<210> SEQ ID NO 9
<211> LENGTH: 3250
<212> TYPE: DNA
<213> ORGANISM: Homo sapiens

<400> SEQUENCE: 9
gcgggcggag gcggggcgcg gagaagtggc ggaggtggaa gcggaggcgt acccgcccct 60
ggggacgtca ttggtggcgg aggcaatggc cggcaaccag ctgtaagcga ggcacggaag 120
acatatgctt gtgagacaaa ggtgtctctg aaactatgga tggtacaaga acttcacttg 180
acattgaaga gtactcggat actgaggtac agaaaaacca agtactaact ctggaagaat 240
ggcaagacaa gtgggtgaac ggcaagactg cttttcatca ggaacaagga catcagctat 300
taaagaagca tttagatact ttccttaaag gcaagagtgg actgagggta ttttttcctc 360
tttgcggaaa agcggttgag atgaaatggt ttgcagaccg gggacacagt gtagttggtg 420
tggaaatcag tgaacttggg atacaagaat tttttacaga gcagaatctt tcttactcag 480
aagaaccaat caccgaaatt cctggaacca aagtatttaa gagttcttcg gggaacattt 540
cattgtactg ttgcagtatt tttgatcttc ccaggacaaa tattggcaaa tttgacatga 600

-continued

```
tttgggatag aggagcatta gttgccatca atccaggtga tcgcaaatgc tatgcagata    660
caatgttttc cctcctggga aagaagtttc agtatctcct gtgtgttctt tcttatgatc    720
caactaaaca tccaggtcca ccattttatg ttccacatgc tgaaattgaa aggttgtttg    780
gtaaaatatg caatatacgt tgtcttgaga aggttgatgc ttttgaagaa cgacataaaa    840
gttggggaat tgactgtctt tttgaaaagt tatatctact tacagaaaag taaatgagac    900
atagataaaa taaaatcaca ctgacatgtt tttgaggaat tgaaaattat gctaaagcct    960
gaaaatgtaa tggatgaatt tttaaaattg tttataaatc atatgataga tctttactaa   1020
aaatggcttt ttagtaaagc catttacttt ttctaaaaaa gttttagaag aaaaagatgt   1080
aactaaactt ttaaagtagc tcctttggag aggagattat gatgtgaaag attatgccta   1140
tgtgtcttgc agattgcaag atattttacc aatcagcatg tgttacctgt acaattaaaa   1200
aaatatttca aaatgcaatg catattaaat ataatacaca cagaaaaact ggcatttatt   1260
ttgttttatt tttttgagat ggagtttcgt tcttgttgcc caacctggag tgcaatggtg   1320
caatctcagc tcactgcaac ctctgcctcc caggttcagg tgattctcct gcctcagcct   1380
cctgagtagc tgggattaca ggtgtgcgcc accacgccca gctaattttt tgtattttta   1440
gtagagacag ggtttcacca tgttggtcag gctgatctcg agctcctgac ctcaggtgat   1500
ctacccacct cggcctccca aagtgctggg attacaggcg tgagccactg cacctggcct   1560
gacattcttt atgaaattta gaattgttga agaactataa catttcagta gggttcaagg   1620
tggtcccaaa agttatataa aagattagtt tttactataa acccttgtct tttactcaga   1680
tcctagcatc ccttttcaca tggtttctcc atgtatataa cagaatcaag aaacaaattt   1740
taattaaaca atctgtaaca gaatcaagaa acaaatacat tttaattaaa caatctatat   1800
ggaacaaaca ttcccaaatt ctaagaataa atttttcttt aagttttctc tgagtttggc   1860
aattgttgtt ttttataatt taatctgttt aaatcatcag gtcttataaa atataatgta   1920
cttagagctg gattcatggc tgtttattat gaaaggttag atttctcagt tcttctttaa   1980
ccacattttg ttatatcaga cagtcctcta taactctgta ctacccaaca actaaatggt   2040
ttagattgtt tagctcatgt taataggatg gttgtgtatt ataaaaaacg agttacgtgt   2100
gtgtgtgcac gcatgcacgc acatgtgctg gcttaaaggt tgttaatgca aggtttgggg   2160
tcccctttaa cactggtgaa agctacggta ctctccccag agatatgtct tgtcagcctc   2220
tctagttccc cttggcctgc atgtacaaac ttctacccta gaagctctct gccatcgatg   2280
tattctaata gatttgtaag gctattaatt tgaagcaact ccttgctcac agtgattctt   2340
gcttctctga gacctgctcc cagtcgatac tgtgggcttc agaagccatg actccccaac   2400
tctgcctgta tcaccggttg aatggacaac taacccgagc tggaccaaca caattctctc   2460
cagagacttt tgattttact tttatgtaga gacagggtct cactttgttg cccacgctga   2520
tgttgaactt gacgtgaggc ctcaagcagt cctcctgtct tggccaccca aagtgctagg   2580
attacaggta tgagccattg cgctggccct cttcataggc ttttggactt gggaatagaa   2640
aagcaacccc gtctctacta aaaatacaaa aaaattagcc aggcgtggtg gcacgtgcct   2700
gtaatcccag ctacttggga ggctgaggca ggagaatcac ttgaacctag gaggcggagg   2760
ttgcagtgag ctgagatcat gccactgcac gcaagcctgg gcaacagagc aagactctgt   2820
ctcaaaagaa agaaaaagaa aagaaaaaaa agaaaggcaa gttgactgct gaaaggggaa   2880
tctgtgtacg cctgggagct gtggggcagc cacattccag cacatggatc tgagaaacag   2940
```

-continued

```
aacgctgatc tgcagaaaga gatgagaacc aaagagaggc cacctgcgtc ctgggtccat   3000

tttcatcctc cctgaagccc agctgcccag ggtggggaga aacaccctgt gtccatggga   3060

tagagtcctt tccgcttgca gttgtgccca aagaatctta aatacaaatg agatatcctt   3120

aggtagttga tcatttatgt aatatgtgtc ttcactgggg aatactgact tcctaaaatc   3180

tcaagatgga agatatacca catgtaaatt attttagagc aattaaattg ttttcaggat   3240

tttccaaaaa                                                          3250


<210> SEQ ID NO 10
<211> LENGTH: 2810
<212> TYPE: DNA
<213> ORGANISM: Homo sapiens

<400> SEQUENCE: 10

ggcctcgagg gacaggacgt gaagatagtt gggtttggag gcggccgcca ggcccaggcc     60

cggtggacct gccgccatgc aggacggtaa cttcctgctg tcggccctgc agcctgaggc    120

cggcgtgtgc tccctggcgc tgccctctga cctgcagctg gaccgccggg gcgccgaggg    180

gccggaggcc gagcggctgc gggcagcccg cgtccaggag caggtccgcg cccgcctctt    240

gcagctggga cagcagccgc ggcacaacgg ggccgctgag cccgagcctg aggccgagac    300

tgccagaggc acatccaggg ggcagtacca caccctgcag gctggcttca gctctcgctc    360

tcagggcctg agtggggaca agacctcggg cttccggccc atcgccaagc cggcctacag    420

cccagcctcc tggtcctccc gctccgccgt ggatctgagc tgcagtcgga ggctgagttc    480

agcccacaac gggggcagcg cctttggggc cgctgggtac gggggtgccc agcccacccc    540

tcccatgccc accaggcccg tgtccttcca tgagcgcggt ggggttggga gccgggccga    600

ctatgacaca ctctccctgc gctcgctgcg gctggggccc gggggcctgg acgaccgcta    660

cagcctggtg tctgagcagc tggagcccgc ggccacctcc acctacaggg cctttgcgta    720

cgagcgccag gccagctcca gctccagccg ggcagggggg ctggactggc ccgaggccac    780

tgaggtttcc ccgagccgga ccatccgtgc ccctgccgtg cggaccctgc agcgattcca    840

gagcagccac cggagccgcg gggtaggcgg ggcagtgccg ggggccgtcc tggagccagt    900

ggctcgagcg ccatctgtgc gcagcctcag cctcagcctg gctgactcgg gccacctgcc    960

ggacgtgcat gggttcaaca gctacggtag ccaccgaacc ctgcagagac tcagcagcgg   1020

ttttgatgac attgacctgc cctcagcagt caagtacctc atggcttcag accccaacct   1080

gcaggtgctg ggagcggcct acatccagca caagtgctac agcgatgcag ccgccaagaa   1140

gcaggcccgc agccttcagg ccgtgcctag gctggtgaag ctcttcaacc acgccaacca   1200

ggaagtgcag cgccatgcca caggtgccat gcgcaacctc atctacgaca acgctgacaa   1260

caagctggcc ctggtggagg agaacgggat cttcgagctg ctgcggacac tgcgggagca   1320

ggatgatgag cttcgcaaaa atgtcacagg gatcctgtgg aacctttcat ccagcgacca   1380

cctgaaggac cgcctggcca gagacacgct ggagcagctc acagacctgg tgttgagccc   1440

cctgtcgggg gctgggggtc ccccccctcat ccagcagaac gcctcggagg cggagatctt   1500

ctacaacgcc accggcttcc tcaggaacct cagctcagcc tctcaggcca ctcgccagaa   1560

gatgcgggag tgccacgggc tggtggacgc cctggtcacc tctatcaacc acgccctgga   1620

cgcgggcaaa tgcgaggaca agagcgtgga gaacgcggtg tgcgtcctgc ggaacctgtc   1680

ctaccgcctc tacgacgaga tgccgccgtc cgcgctgcag cggctggagg gtcgcggccg   1740

cagggacctg gcgggggcgc cgccgggaga ggtcgtgggc tgcttcacgc cgcagagccg   1800
```

-continued gcggctgcgc gagctgcccc tcgccgccga tgcgctcacc ttcgcggagg tgtccaagga 1860
ccccaagggc ctcgagtggc tgtggagccc ccagatcgtg ggctgtaca accggctgct 1920 gcagcgctgc gagctcaacc ggcacacgac ggaggcggcc gccggggcgc tgcagaacat 1980
cacggcaggc gaccgcaggt gggcgggggt gctgagccgc ctggccctgg agcaggagcg 2040
tattctgaac cccctgctag accgtgtcag gaccgccgac caccaccagc tgcgctcact 2100
gactggcctc atccgaaacc tgtctcggaa cgctaggaac aaggacgaga tgtccacgaa 2160
ggtggtgagc cacctgatcg agaagctgcc gggcagcgtg ggtgagaagt cgcccccagc 2220
cgaggtgctg gtcaacatca tagctgtgct caacaacctg gtggtggcca gccccatcgc 2280
tgcccgagac ctgctgtatt ttgacggact ccgaaagctc atcttcatca agaagaagcg 2340
ggacagcccc gacagtgaga agtcctcccg ggcagcatcc agcctcctgg ccaacctgtg 2400
gcagtacaac aagctccacc gtgacttccg ggcgaagggc tatcggaagg aggacttcct 2460
gggcccatag gtgaagcctt ctggaggaga aggtgacgtg gcccagcgtc caagggacag 2520
actcagctcc aggctgcttg gcagcccagc ctggaggaga aggctaatga cggaggggcc 2580
cctcgctggg gcccctgtgt gcatctttga gggtcctggg ccaccaggag gggcagggtc 2640
ttatagctgg ggacttggct tccgcagggc agggggtggg gcagggctca aggctgctct 2700
ggtgtatggg gtggtgaccc agtcacattg gcagaggtgg gggttggctg tggcctggca 2760
gtatcttggg atagccagca ctgggaataa agatggccat gaacagtcaa 2810

<210> SEQ ID NO 11
<211> LENGTH: 3131
<212> TYPE: DNA
<213> ORGANISM: Homo sapiens

<400> SEQUENCE: 11
agtgtttatc agaacttagc cagggccagc caagcaggca cagatgctct gctatgaaat 60
gccacgcagg cagagactga caagcggtag gaactgagct ttccccttgg actgctgctt 120
cctgctgtgt tcaggggagg gggtcacttt ctggcaactc tgctgctgct gctgctgctg 180
ctgctacttc agcttcctct ccactcaagg taagcaggct aagggagggc aggctgctag 240
ggaaagcttt gtaccatgaa caggatccga aagtttttcc gaggaagtgg gcgagtcttg 300
gcatttatct ttgtagcttc tgtcatctgg ctcctctttg acatggcagc tctccgcctc 360
tcattcagtg agatcaacac tcgggtcatc aaggaagaca ttgtgaggag ggagcggata 420
ggattcagag ttcagccaga ccaaggaaaa attttttaca gcagcataaa agagatgaaa 480
cctcccctaa ggggacatgg gaaaggggca tggggcaaag agaatgttag aaaaactgag 540
gagagtgtgc tcaaggttga ggtggacttg gaccaaaccc agagggaaag aaaaatgcag 600
aatgccctgg gaaggggcaa ggttgtgccg ttgtggcatc ctgcacatct gcagaccctc 660
cctgtgactc ctaacaagca gaagacagac gggagaggca ccaaacctga agcctcctct 720
caccagggga caccaaagca aacgacagct cagggggctc caaagacctc attcatagca 780
gcaaaaggaa ctcaggtagt caaaatatca gtacacatgg gacgtgtcag tttaaaacag 840
gagccccgga agagtcatag tcccagcagt gacacatcaa aactagcagc tgaaagggac 900
ttgaatgtga ccatcagtct tagtactgat agaccaaagc agcgatcaca ggcagtagca 960
aacgagaggg cacaccctgc cagcacagca gtgccgaagt ctggggaagc catggcctta 1020
aacaaaacta agactcagag caaagaagtc aatgcaaata aacacaaagc caatacgagt 1080

-continued

```
cttccttttc ctaagttcac tgtcaattca aatcgcttaa ggaagcaatc tattaatgag   1140

acacctttgg gaagtttgtc aaaggatgat ggagctagag gggctcatgg gaagaaactc   1200

aatttctctg aaagccatct tgtgattata accaaagagg aagagcaaaa ggcagacccc   1260

aaagaggtct ctaattctaa aaccaaaaca atatttccta aagtattggg taaaagccaa   1320

agtaaacaca tttccaggaa tagaagtgag atgtcttcct cttcacttgc tccacataga   1380

gtgccactgt cccaaactaa ccatgcttta actggagggc tagagccagc aaaaatcaac   1440

ataactgcca aagccccctc tacagaatac aaccagagtc atataaaagc ccttttacct   1500

gaagacagtg gaacgcacca ggtgttaaga attgatgtga cactttctcc aagggacccc   1560

aaagctccag ggcagtttgg gcgtcctgta gttgtccccc atggaaagga gaaggaggca   1620

gaaagaagat ggaaagaagg aaacttcaat gtctacctta gcgatttgat cccagtggat   1680

agagccattg aagacaccag acctgctgga tgtgcagagc agctagttca caataacctc   1740

ccaaccacca gtgtcatcat gtgctttgtg gatgaagtgt ggtccactct cctgagatct   1800

gttcacagtg tcatcaatcg ctctcctcca cacctcatca aggagattct gctggtagat   1860

gacttcagca ccaaagacta tctaaaagat aatttggata aatacatgtc ccagtttcca   1920

aaagttcgga ttcttcgcct caaagagaga catggcttaa taagggccag gctggcagga   1980

gcacagaatg caacaggtga tgtgttgaca tttttagatt ctcatgtgga atgtaacgtt   2040

ggttggttgg aacctcttct ggaaagagtt tatttaagta gaaagaaagt ggcctgtcca   2100

gtaatcgaag tcatcaatga taaggatatg agttacatga cagtggataa ctttcaaaga   2160

ggcatctttg tgtggcccat gaactttggt tggagaacaa ttcctccaga tgtcattgca   2220

aaaaacagaa ttaaagaaac tgatacaata aggtgccctg tcatggctgg tggattgttt   2280

tctattgaca aaagttactt ttttgaactt ggaacatacg accctggcct tgatgtttgg   2340

ggtggggaaa atatggagct ctcattcaag gtgtggatgt gtggtggtga aattgagatc   2400

attccctgct cccgagtggg ccatatattc agaaatgaca atccatattc cttccccaaa   2460

gaccggatga agacagtgga gcggaacttg gtgcgggttg ccgaggtctg gctggatgag   2520

tataaggagc tgttctatgg ccacggagac cacctcatcg accaagggct agatgttggc   2580

aacctcaccc agcaaaggga gctgcgaaag aaactgaagt gcaaaagttt caaatggtac   2640

ttggagaatg tctttcctga cttaagggct cccattgtga gagctagtgg tgtgcttatt   2700

aatgtggctt tgggtaaatg catttccatt gaaaacacta cagtcattct ggaagactgc   2760

gatgggagca aagagcttca acaatttaat tacacctggt taagacttat taaatgtgga   2820

gaatggtgta tagcccccat ccctgataaa ggagccgtaa ggctgcaccc ttgtgataac   2880

agaaacaaag ggctaaaatg gctgcataaa tcaacatcag tctttcatcc agaactggtg   2940

aatcacattg tttttgaaaa caatcagcaa ttattatgct tggaaggaaa tttttctcaa   3000

aagatcctga aagtagctgc ctgtgaccca gtgaagccat atcaaaagtg gaaatttgaa   3060

aaatattatg aagcctgaag tgtaactgat gtttttatat agtaaaccca ttaaatactg   3120

tgaaaataac a                                                        3131
```

```
<210> SEQ ID NO 12
<211> LENGTH: 4640
<212> TYPE: DNA
<213> ORGANISM: Homo sapiens

<400> SEQUENCE: 12

ggggctgagg gtggagagag gaagggaagg aagaaaaggg gagccttcct ggccagggta     60
```

-continued

```
accggcacta agaggcctca ctccaagccc ccgaggagcc tgtggtgggg ctggagaccc    120
ggctcaggcc cctccaccac ccttaaagtc ctcagaaggt gggaactgaa ctggcacagg    180
atgggaaccg gctgtgcgct ggccacttga ttttgccagc tgccctgtaa ttcagctggt    240
gaggaaactg aggcacagac tgaggtagaa tgattcgcca gtcactcagc aagtcagcag    300
acggggagga ctgaatccca gcctgagagc accgaagctt gtatccctgc aataccgagc    360
cccaagcctg cgagccccgg tgcccatctc tgagttaggc cgtcttggaa gggttccctt    420
cctcctacaa gatggtgtgt gaggagcctt caatacgacc cggggtgtaa agtgtccaac    480
tctagtaggg gcctgatggc atccccgccg agtcccagga gagagagaga agaccccttc    540
ctggagtcca gggctcccgg gaagaaacac tggcatttgt ccctttgctt cggcttctgg    600
aggcagagac tctgagccca gggagagcct tctgcagccc catttcctca aaaatccaac    660
ctgcccaggt ggcgggtcat gagctgtgct caggaagctg gaatctgacc ctggtggcgt    720
cgggcccagt ctccatggca gccgagcatt tattacccgg gcctccaccc agcttggcag    780
actttagact tgaggctgga ggaaagggaa ctgaacgcgg ttctgggagc agcaagccca    840
cgggtagcag ccgaggcccc agaatggcca agtttctttc ccaagaccaa attaatgagt    900
acaaggaatg cttctccctg tatgacaagc agcagagggg gaagataaaa gccaccgacc    960
tcatggtggc catgaggtgc ctgggggcca gcccgacgcc aggggaggtg cagcggcacc   1020
tgcagaccca cgggatagac ggaaatggag agctggattt ctccactttt ctgaccatta   1080
tgcacatgca aataaaacaa gaagacccaa agaaagaaat tcttctagcc atgttgatgg   1140
tggacaagga gaagaaaggt tacgtcatgg cgtccgacct gcggtcaaaa ctcacgagtc   1200
tgggggagaa gctcacccac aaggaagtgg atgatctctt cagggaagca gatatcgaac   1260
ccaatggcaa agtgaagtat gatgaattta tccacaagat caccctttcct ggacgggact  1320
attgaaggag gagaatggga gagcctcccc tgggcctgaa aacttggagc aattaatttt   1380
ttttaaaaag tgttcttttc acttgggaga gatggcaaac acagtggcaa gacaacatta   1440
cccaactata gaagagaggc taactagcaa caataataga tgatttcagc catggtatga   1500
gtagatcttt aataaaagat ttgtattgat tttattaact accgtgagtc cggccctttc   1560
aagcatggaa ggagcctgcg gtttggagtc tggcctgggt tccagtcctg gctctgctgc   1620
ttcccactgt gactttgggc aaatcatttc actcctcaaa gcccccccac acaagctgga   1680
ttcccacttc ttacctcatg gagcctgttg aggaaggatt gagctgatga cttaagggca   1740
atctaccaag agacttattc tgtatttggg ggctagaacc atcttccata tttccaagat   1800
tttccaagat gaagccagtg ctagctgaga agcagcaatg aacagaaagc tgtaacactt   1860
atgacaacaa ttcttgcagt gccagaggcc catttacaaa ttctcatttc catctcaaca   1920
gatatagtga catagctcag gctattcatt cataaacaca gagtgtagag tgaaaacact   1980
agagtgaaaa cacatgctac aatgaggcag catcagctga gagcaggaag agcgatctac   2040
tttacacccc acaccaaagg aaaccagatg tgagctgcta aattgactgg ccttgcagag   2100
ctcaagaagg gggcttccaa tgctgtgaga attccgagct gttccctggg ctctgttaac   2160
aggcagagag gttccgggat ggtctgctca agtggcccac actggtcatt gccttaagcc   2220
acctccccag gacttacgga gagaaataag gggatgtaac cagcaatggc cagggtacaa   2280
cagccctgga aaacagtagt aggagcacta ggctttctgg gagtccatcc agctggagtg   2340
gctttgagtg agttacacag ctagaaggtg ccaggttggt gctgccagag attcagaggt   2400
```

```
gccatacact tgtcaaatct ggatcattcg tagtgccagc acagtcctaa aagggctgga   2460

gtaccacacc aacacaggta ggggtgcagg gcttcaagta caaagatttg catccatgta   2520

tgtatcaaaa gtgggttctc tgggctgtgg ctttgtctag tagtaccaca gtggctaaag   2580

tagaagaaaa ccaaatcaaa tgggatgtgt cttttgggag gatgtacaag acacaaatct   2640

ttcactaggc accgggcaca gggaaaactg cagggaacaa gagttgtagt gttagtgcaa   2700

ctgtctcaac gatgctgtgt ggcttcagac ccaaacaagg ccctgaggaa ggagactctc   2760

atttccccaa gcataactgc aaggagagga ggaattccta ggagccaaag agttttgtgg   2820

ggtgagggta aataaatggc ccaaatgcca actaggtgaa gttgtgacca tctggctggg   2880

aagcccaggt ccacacagtg taggagcaga tgttttgtgg ggtctgaggt ttacgagatt   2940

tggctgcctt aagaatacaa aaacagaaat gcagaatttc tggggctgct cctaggacca   3000

gaacaagtga agggtcctgg tgcttaaact tcattacctt catggtaaat ccaccagagg   3060

gccggttaga tgctggcccc gccgagagaa ctgctgtcac tttcaggcaa agctcaaagg   3120

tcctaggccc acagttcttt tgagctccag tcatggacat taggaagtaa atcctgcaca   3180

gccaacctgg aataccaaag attagatggg agatagatac caatgattta gatggcacag   3240

gaagagcaag ttctggatat aataaatgag ggtactttcc gtcaaagctt ttctatgtct   3300

atatttatca ctgaatagtc ccagtatggt tttaaagcaa gttttatgaa tctcatttgc   3360

ctaacaggaa tctgaaatat aacttgccaa aaacacacag ttggtgtgga atggtcatta   3420

gaacctgggg ctcctcttca cggactccct gctcattaag ggattcagtg gtccagagtc   3480

taagatccta ttaagtgttt gattcaaacc tctacccgag gaagggctgt taccttactc   3540

ctggtcctgg tttcaagctc attcctgaaa ttccagctgg tttctctagc acctagtgtt   3600

gtttacaaga aggccacggt gctcttagca ttcaaactgc agatactaaa cagatgctgt   3660

gatttattaa agagttagcc atatttcaac aagaaaggga aatgatggct atattcatta   3720

cttacctcaa agcatgctgc aagaaaatta gttagttact tgtcatgctt tgaaatctct   3780

ggatgaaagg tgctttggaa gcacaaacca ttatcacttg tctcataggg attgtcccct   3840

tgaacatcca gcagtgttat tttacagaag acaaattaac tgaaggcttt tcttttatta   3900

catctaaaga gctctacata aacaggtaac attcaatagg taaacaattt ttttccaatg   3960

catgtaataa atattttcac ttggtacttt tatacaaact gacattgtct actatacatt   4020

tttaaaagcc attttactgg tttggcatgc ggtatggaaa ttctaagaga gaaagtttta   4080

aggcaatgaa tcacagattt aagttcatgg aatttatggt aactttatct gtttatgtac   4140

attttcccct ttgttaaaca attaacagca gcacactctg ggaccaccag ctattttccc   4200

tctctttctg aaatctaagc tttgtattta attaaaaaac agaattcaac atctattgat   4260

aaaacaaaat tcttactaaa ataatttcaa atgtgcttta aaaagtcctg aagatcttga   4320

aagttttatg tgtttaaaat tgaaattgtc taaaaaaatg ctctttccac attaatttag   4380

ttaggatata ttttcactcc atttcagaca cttgactcaa aggaaaatct gccaaagaat   4440

ccgatttttc agagcttacg tgaatctttc ctcagtaaag atacagaatt gtgatcatgt   4500

ctaaataatt agtaaagcaa ttttaatgct caaaatagtc aaccaagtat ggcatggttc   4560

tggttcagat tttttttttt taagatgtat ccaataacac tcacgaagta attaaaagcc   4620

actttaaccc tgctaaaaaa                                                4640
```

<210> SEQ ID NO 13
<211> LENGTH: 2300

-continued

<212> TYPE: DNA
<213> ORGANISM: Homo sapiens

<400> SEQUENCE: 13
cattttataa tgaagcctgg tcaactctcc ttcggacagt ttacagtgtc cttgagacat 60
ccccggatat cctgctagaa gaagtgatcc ttgtagatga ctacagtgat agagagcacc 120
tgaaggagcg cttggccaat gagctttcgg gactgcccaa ggtgcgcctg atccgcgcca 180
acaagagaga gggcctggtg cgagcccggc tgctgggggc gtctgcggcg aggggcgatg 240
ttctgacctt cctggactgt cactgtgagt gccacgaagg gtggctggag ccgctgctgc 300
agaggatcca tgaagaggag tcggcagtgg tgtgcccggt gattgatgtg atcgactgga 360
acaccttcga atacctgggg aactccgggg agccccagat cggcggtttc gactggaggc 420
tggtgttcac gtggcacaca gttcctgaga gggagaggat acggatgcaa tccccgtcg 480 atgtcatcag gtctccaaca atggctggtg ggctgtttgc tgtgagtaag aaatattttg 540
aatatctggg gtcttatgat acaggaatgg aagtttgggg aggagaaaac ctcgaatttt 600
cctttaggat ctggcagtgt ggtggggttc tggaaacaca cccatgttcc catgttggcc 660
atgttttccc caagcaagct ccctactccc gcaacaaggc tctggccaac agtgttcgtg 720
cagctgaagt atggatggat gaatttaaag agctctacta ccatcgcaac ccccgtgccc 780
gcttggaacc ttttggggat gtgacagaga ggaagcagct ccgggacaag ctccagtgta 840
aagacttcaa gtggttcttg gagactgtgt atccagaact gcatgtgcct gaggacaggc 900
ctggcttctt cgggatgctc cagaacaaag gactaacaga ctactgcttt gactataacc 960
ctcccgatga aaaccagatt gtgggacacc aggtcattct gtacctctgt catgggatgg 1020
gccagaatca gtttttcgag tacacgtccc agaaagaaat acgctataac acccaccagc 1080
ctgagggctg cattgctgtg gaagcaggaa tggataccct tatcatgcat ctctgcgaag 1140
aaactgcccc agagaatcag aagttcatct tgcaggagga tggatcttta tttcacgaac 1200
agtccaagaa atgtgtccag gctgcgagga aggagtcgag tgacagtttc gttccactct 1260
tacgagactg caccaactcg gatcatcaga aatggttctt caaagagcgc atgttatgaa 1320
gcctcgtgta tcaaggagcc catcgaagga gactgtggag ccaggactct gcccaacaaa 1380
gacttagcta agcagtgacc agaacccacc aaaaactagg ctgcattgct ttgaagaggc 1440
aatcattttg ccatttgtga aagttgtgtt ggatttagta aaaatgtgaa taagctttgt 1500
acttattttg agaacttttt aaatgttcca aaatacccta ttttcaaagg gtaatcgtaa 1560
gatgttaacc cttggtattt agaaaattaa aaccttataa tatttttcta tcaagatgta 1620
tattttacag tcgtgccttt tactctcatt agcaaaaaag ataaagattt tattttggta 1680
tttacaagaa ttcccaggta cgaagatatc tgcatgggtg gaaatcaggt tcaagcaacg 1740
tactttgcat taactgataa tacctcagct gcggggttaa agttttccca gtatagagag 1800
actgtcacta ggaacattgt attgatttat tcaggtcatt gagatcttct agatgtattt 1860
taaaaagaat gctttttggt tatgtgttgc taccacagtt aacactccat aatgttcatg 1920
tcagccaaag aggactaacc aaagctgaaa tctcagagaa caatttgctt tactaagctg 1980
agtcaacttg agagcgaact tctaacaatg ccgcactgta gtgtggctgg ttctaccact 2040
atgactttaa aacatgttta tatcattttt aatttttatg atacggtagt gtcagggaga 2100
aatgtaatgt tctatatgaa attccttttt caagtttgtt cattaataac agttattaat 2160
ttaaatcagc gttagagttt gtgctgctgc aactgctgtg aaaatttctc tgagtaattc 2220

-continued

```
tgatttgtga atgatcccag accaaccctg agattttgtc aacctgatta agtcaatatg   2280

aatgattaaa aagatgtgag                                               2300


<210> SEQ ID NO 14
<211> LENGTH: 2440
<212> TYPE: DNA
<213> ORGANISM: Homo sapiens

<400> SEQUENCE: 14

aaggctcctc agccgagcgc cgagcggtcg atcgccgtag ctcccgcagc ctgcgatctc     60

cagtctgtgg ctcctaccag ccattgtagg ccaataatcc gttatggagc atgcctttac    120

cccgttggag cccctgcttt ccactgggaa tttgaagtac tgccttgtaa ttcttaatca    180

gcctttggac aactattttc gtcatctttg gaacaaagct cttttaagag cctgtgccga    240

tggaggtgcc aaccgcttat atgatatcac cgaaggagag agagaaagct tttgcctga     300

attcatcaat ggagactttg attctattag gcctgaagtc agagaatact atgctactaa    360

gggatgtgag ctcatttcaa ctcctgatca agaccacact gactttacta agtgccttaa    420

aatgctccaa aagaagatag aagaaaaaga cttaaaggtt gatgtgatcg tgacactggg    480

aggccttgct gggcgttttg accagattat ggcatctgtg aataccttgt tccaagcgac    540

tcacatcact ccttttccaa ttataataat ccaagaggaa tcgctgatct acctgctcca    600

accaggaaag cacaggttgc atgtagacac tggaatggag ggtgattggt gtggccttat    660

tcctgttgga cagccttgta tgcaggttac aaccacaggc ctcaagtgga acctcacaaa    720

tgatgtgctt gcttttggaa cattggtcag tacttccaat acctacgacg ggtctggtgt    780

tgtgactgtg gaaactgacc acccactcct ctggaccatg gccatcaaaa gctaacctgt    840

tgactggcat ccataagtgt gcctctgcct tatctcattt ctcaacagtt cattgctcaa    900

caagaacgat tcacctgggt ttgcaagaat ctaaacctct ctaggggaag cccactgggt    960

ttaaagatgt tagtgtttag ataatacagg taacattata aatgacagat ctcaatttta   1020

tagtagtggg aaagatacat gctaagaaag caaataagct ctattatatt cggttggaac   1080

ctaatgggaa tcattccact atacaattca gtactgatta ttcttcttac attattaatc   1140

attccattta tcctagaaaa ttgtttttaa tttgaatcag agaaaactgt tgaggttcct   1200

cttggagtct agaacatcct taaatgtcta acaacaaggg ctacctctga gtacctttta   1260

gtattagttt tctgtatatg atatatatta tcttatactg aaaaaaaatt cctttcagat   1320

tggggtgtta gaagtgcacc aggtcactct gaccttatta ctgtctttgg tattgtctta   1380

aataaatcaa gaatcattga cctaattgtt aaatttaaaa ataggtagtt agcaataggt   1440

ggaaagagaa atgatgtgaa agataaatga tgattcgtgg agccctactc acacattaac   1500

ccccaaattc aaaagtaaga atgcaaaagt ctagaggggg taacagtctg catcatcatc   1560

acaacctaaa tggagaaagc tgtgcagagg aaacttaagc ataaaaattg aattcgtttc   1620

tgacatacct tagactgaaa aactgttggt tcatccagaa gtgtattcat attaccagaa   1680

aatgagtttg tctatgggga tacatgaact tcatatacta aggagcctaa ctccaaagcc   1740

tgcgttctca tcccagtctg atattcacct aagtttccgg acccttttcc ttagctgtaa   1800

aatggaagcg gttggactga tggtgtctga ggttctttcc cacactgaaa ttctaaatat   1860

tgacacttag cagtcatagg gctgataata cacacagtta ctgacttagc ctaaacaacc   1920

tggtgcatcg aaatgtattc acctttcttt tgtaaagaga ccatcttcta tcttctttcc   1980

acctttctct gttttatgaa accaactgtt gacatacaaa ccatgattga aggagaacct   2040
```

-continued gtccaacatg ttttatgtac acaaatccct atgttgctat aagaaaagtg aaagtaactg 2100
ttttcttctt ggtgctatga cagtgtgaga ctcaggttgt ctgtagagaa tgaaaggagc 2160
agtggcccgc gtgattgtgg catttaagga gcagtggccc atgtgactgt ggcattttcg 2220
gcacttttca ttactttctg cttgaccgga agttgaggct tagctatgtt tccatcttca 2280
gtttctgaag actagttata tattccttac tagaaatata ttcataatat ataaaagaaa 2340
tatatctgtg attttaaaat tttgctacca aagaatgcat gttctgtgtg ccctgaaaat 2400
gttaccagtg ttaataaatg gatacttatc aaaaaagaaa 2440

<210> SEQ ID NO 15
<211> LENGTH: 475
<212> TYPE: DNA
<213> ORGANISM: Homo sapiens

<400> SEQUENCE: 15
acacatctgc tcctgctctc tctcctccag cgaccctagc catgagaacc ctcaccatcc 60
tcactgctgt tctcctcgtg gccctccagg ccaaggctga gccactccaa gctgaggatg 120
atccactgca ggcaaaagct tatgaggctg atgcccagga gcagcgtggg gcaaatgacc 180
aggactttgc cgtctccttt gcagaggatg caagctcaag tcttagagct ttgggctcaa 240
caagggcttt cacttgccat tgcagaaggt cctgttattc aacagaatat tcctatggga 300
cctgcactgt catgggtatt aaccacagat tctgctgcct ctgagggatg agaacagaga 360
gaaatatatt cataatttac tttatgacct agaaggaaac tgtcgtgtgt cccatacatt 420
gccatcaact ttgtttcctc atctcaaata aagtcctttc agcaaaaaaa aaaaa 475

<210> SEQ ID NO 16
<211> LENGTH: 3650
<212> TYPE: DNA
<213> ORGANISM: Homo sapiens

<400> SEQUENCE: 16
gcgctaggta gagcgccggg acctgtgaca gggctggtag cagcgcagag gaaaggcggc 60
ttttagccag gtatttcagt gtctgtagac aagatggaat catctccatt taatagacgg 120
caatggacct cactatcatt gagggtaaca gccaaagaac tttctcttgt caacaagaac 180
aagtcatcgg ctattgtgga aatattctcc aagtaccaga aagcagctga agaaacaaac 240
atggagaaga agagaagtaa caccgaaaat ctctcccagc actttagaaa ggggaccctg 300
actgtgttaa agaagaagtg ggagaaccca gggctgggag cagagtctca cacagactct 360
ctacggaaca gcagcactga gattaggcac agagcagacc atcctcctgc tgaagtgaca 420
agccacgctg cttctggagc caaagctgac caagaagaac aaatccaccc cagatctaga 480
ctcaggtcac ctcctgaagc cctcgttcag ggtcgatatc cccacatcaa ggacggtgag 540
gatcttaaag accactcaac agaaagtaaa aaaatggaaa attgtctagg agaatccagg 600
catgaagtag aaaaatcaga aatcagtgaa aacacagatg cttcgggcaa aatagagaaa 660
tataatgttc cgctgaacag gcttaagatg atgtttgaga aaggtgaacc aactcaaact 720
aagattctcc gggcccaaag ccgaagtgca agtggaagga agatctctga aaacagctat 780
tctctagatg acctggaaat aggcccaggt cagttgtcat cttctacatt tgactcggag 840
aaaaatgaga gtagacgaaa tctggaactt ccacgcctct cagaaacctc tataaaggat 900
cgaatggcca agtaccaggc agctgtgtcc aaacaaagca gctcaaccaa ctatacaaat 960

```
gagctgaaag ccagtggtgg cgaaatcaaa attcataaaa tggagcaaaa ggagaatgtg   1020
cccccaggtc ctgaggtctg catcacccat caggaagggg aaaagatttc tgcaaatgag   1080
aatagcctgg cagtccgttc cacccctgcc gaagatgact cccgtgactc ccaggttaag   1140
agtgaggttc aacagcctgt ccatcccaag ccactaagtc cagattccag agcctccagt   1200
ctttctgaaa gttctcctcc caaagcaatg aagaagtttc aggcacctgc aagagagacc   1260
tgcgtggaat gtcagaagac agtctatcca atggagcgtc tcttggccaa ccagcaggtg   1320
tttcacatca gctgcttccg ttgctcctat tgcaacaaca aactcagtct aggaacatat   1380
gcatctttac atggaagaat ctattgtaag cctcacttca atcaactctt taaatctaag   1440
ggcaactatg atgaaggctt tgggcacaga ccacacaagg atctatgggc aagcaaaaat   1500
gaaaacgaag agattttgga gagaccagcc cagcttgcaa atgcaaggga gacccctcac   1560
agcccagggg tagaagatgc ccctattgct aaggtgggtg tcctggctgc aagtatggaa   1620
gccaaggcct cctctcagca ggagaaggaa gacaagccag ctgaaaccaa gaagctgagg   1680
atcgcctggc cacccccac tgaacttgga agttcaggaa gtgccttgga ggaagggatc   1740
aaaatgtcaa agcccaaatg gcctcctgaa gacgaaatca gcaagcccga agttcctgag   1800
gatgtcgatc tagatctgaa gaagctaaga cgatcttctt cactgaagga aagaagccgc   1860
ccattcactg tagcagcttc atttcaaagc acctctgtca agagcccaaa aactgtgtcc   1920
ccacctatca ggaaaggctg gagcatgtca gagcagagtg aagagtctgt gggtggaaga   1980
gttgcagaaa ggaaacaagt ggaaaatgcc aaggcttcta agaagaatgg gaatgtggga   2040
aaaacaacct ggcaaaacaa agaatctaaa ggagagacag ggaagagaag taaggaaggt   2100
catagtttgg agatggagaa tgagaatctt gtagaaaatg gtgcagactc cgatgaagat   2160
gataacagct tcctcaaaca acaatctcca caagaaccca agtctctgaa ttggtcgagt   2220
tttgtagaca acacctttgc tgaagaattc actactcaga atcagaaatc ccaggatgtg   2280
gaactctggg agggagaagt ggtcaaagag ctctctgtgg aagaacagat aaagagaaat   2340
cggtattatg atgaggatga ggatgaagag tgacaaattg caatgatgct gggccttaaa   2400
ttcatgttag tgttagcgag ccactgccct ttgtcaaaat gtgatgcaca taagcaggta   2460
tcccagcatg aaatgtaatt tacttggaag taactttgga aaagaattcc ttcttaaaat   2520
caaaaacaaa acaaaaaaac acaaaaaaca cattctaaat actagagata actttactta   2580
aattcttcat tttagcagtg atgatatgcg taagtgctgt aaggcttgta actggggaaa   2640
tattccacct gataatagcc cagattctac tgtattccca aaaggcaata ttaaggtaga   2700
tagatgatta gtagtatatt gttacacact attttggaat tagagaacat acagaaggaa   2760
tttaggggct taaacattac gactgaatgc actttagtat aaagggcaca gtttgtatat   2820
ttttaaatga ataccaattt aattttttag tatttacctg ttaagagatt atttagtctt   2880
taaatttttt aggttaattt tcttgctgtg atatatatga ggaatttact actttatgtc   2940
ctgctctcta aactacatcc tgaactcgac gtcctgaggt ataatacaac agagcacttt   3000
ttgaggcaat tgaaaaacca acctacactc ttcggtgctt agagagatct gctgtctccc   3060
aaataagctt ttgtatctgc cagtgaattt actgtactcc aaatgattgc tttcttttct   3120
ggtgatatct gtgcttctca taattactga aagctgcaat attttagtaa taccttcggg   3180
atcactgtcc cccatcttcc gtgttagagc aaagtgaaga gtttaaagga ggaagaagaa   3240
agaactgtct tacaccactt gagctcagac ctctaaaccc tgtatttccc ttatgatgtc   3300
cccttttttga gacactaatt tttaaatact tactagctct gaaatatatt gatttttatc   3360
```

```
acagtattct cagggtgaaa ttaaaccaac tataggcctt tttcttggga tgattttcta   3420

gtcttaaggt ttggggacat tataaacttg agtacatttg ttgtacacag ttgatattcc   3480

aaattgtatg gatgggaggg agaggtgtct taagctgtag gcttttcttt gtactgcatt   3540

tatagagatt tagctttaat attttttaga gatgtaaaac attctgcttt cttagtctta   3600

cctagtctga aacattttta ttcaataaag attttaatta aaatttgaaa              3650


<210> SEQ ID NO 17
<211> LENGTH: 5703
<212> TYPE: DNA
<213> ORGANISM: Homo sapiens

<400> SEQUENCE: 17

gacagtcgcg gatcctgtga cacctccggg cagcccggca cttgttgctc ccacgacctg     60

ttgtcattcc cttaacccgg ctttccccgt ggcccccgc ctcctcccgg cttcgctcct     120

tttcatgtga gcatctggga cactgatctc tcagaccccg ctgctcgggc tggagaatag    180

atggttttgt gaaaaattaa acaccgccct gaagaggagc cccgctgggc agcggcagga    240

gcgcagagtg ctggcccagg tgctgcagag gtggcgcctc cccggcccgg gacggtagcc    300

ccgggcgcca acggcatgac agactcggcg acagctaacg gggacgacag ggaccccgag    360

atcgagctct ttgtgaaggc tggaatcgat ggagaaagca tcggcaactg tcctttctct    420

cagcgcctct tcatgatcct ctggctgaaa ggagtcgtgt tcaatgtcac cactgtggat    480

ctgaaaagaa agccagctga cctgcacaac ctagcccccg gcacgcaccc gcccttcctg    540

accttcaacg gggacgtgaa gacagacgtc aataagatcg aggagttcct ggaggagacc    600

ttgacccctg aaaagtaccc caaactggct gcaaaacacc gggaatccaa cacagcgggc    660

atcgacatct tttccaagtt ttctgcctac atcaaaaata ccaagcagca gaacaatgct    720

gctcttgaaa gaggcctaac caaggctcta aagaaattgg atgactacct gaacacccct    780

ctaccagagg agattgacgc caacacttgt ggggaagaca aggggtcccg gcgcaagttc    840

ctggatgggg atgagctgac cctggctgac tgcaatctgt tgcccaagct ccatgtggtc    900

aagattgtgg ccaagaaata ccgcaactat gatatcccgg ctgagatgac aggcctgtgg    960

cggtacctca agaacgccta tgcccgtgat gagttcacca acacctgtgc agctgacagt   1020

gagatcgagt tggcctacgc tgatgtcgcc aaacgcctca gccgatcctg agcacagcca   1080

ttttgcccca tccccgctgc agaaggactc aaccactccc ctaagactcc agcttcatag   1140

actcctctgt atcactgcct tgaggcgcac tttttataat caagcctcat cttgctggta   1200

tcatgggaac tccagcctgc tatctttcat gaaggtcagc accatccctg gcctcctcac   1260

ataggaatct agcagaaatg atagacacag tccacctttc ggccggccag cctgatctgg   1320

gctcagcatg tttggggtca gtcagtgttg gagagcccac atatgggatt gccactagct   1380

tcttctgcca atatcaaaat accttctcag atgctttaga aacatgcaac accaactcct   1440

tttctaccct cctctccgtc catacctaca aggccaagga caaacgccat cttcatcctt   1500

cttagaaaga gatctattac cccattaggg gagacagaga gagtgaatgg aggagtaccg   1560

agctggctat ggacttgggt gtctggcaaa cacagcttca gtctcactac ttctgacact   1620

ctggttattg ggcactaagg gccagactgg aaagtcactt gagacacatt ctcagtttgt   1680

tgcagtgcca ggaatgctgc gctgctgctg ctgcgcacct ggcccatgct gtccctggct   1740

tccatgccgt ccaggccctg ccagaaaagg aaattggcat gcaattctaa actgcagtga   1800
```

-continued

```
ctgggatggg aggggagggg agcagtgttg atgccaaaat acccacgggg tctaccagcc   1860
atggggtttg cttgcttagg agtagttgtt tcagaggtga ttacaggcct gggtttgact   1920
gtgcttacca atgagtggtt tttgagctat gagaaagtgg atgggagtgg gaggaggaga   1980
gatgggtgaa gacaaaagag ttctttatga gcctcgatgt tccctggtaa acttttaaaa   2040
aggccttctc tcatgatcta agtcttggac tggtggcatc atgtaactgc taaccttaca   2100
gtaaaaaccc aagaatgggt caaaaatgtc ttcccagttt ctccaagctg cttctggaat   2160
gcaggtctgt cggctgggtg ctctccagca gctgctcctg cctgattcaa ctgtagcctg   2220
taatgggtaa aagccacatt taggaggtgg tctgatcata gaacacctta ggaagaaagt   2280
ccatgagact ttctgactag gaaaccatgt ggtttgaact tgaagaaaaa tgtagaccca   2340
tctgggttaa ttttcctaca atctgactca actgccaggt gaaaaaaaaa aggaaaaatt   2400
tttaagctaa tatttcactc ttttgtcatt ctccttaagt ttcatctcct aaaaagctta   2460
cccagcctga gcttggggac ctgtgcagag gaaactaaga aaaatgcact catcaactcc   2520
ttctcccagt gaacgcccgg tgagaaaatc catttgccac aggcccttac cttcaacaat   2580
ccccccttcta tagtgttcgc tggtaaaggg tgaggctccc aagtgctgga aagcccctgg   2640
acttggctca tttctcagca agggcaggat agcacgggtc ctttccatag aaatatcaac   2700
aaattctaac ccaagcaatc cctggaccta cctgcctcca gggatctctg aagaaaaaaa   2760
gtaacccatt gatcaaatca gaggagagga agcaggaggt ctcctagagc ccattgagga   2820
agaggaactt tctcagtagg acactttata agcctgagaa agctttgaaa aggcggaatg   2880
agttgattca tttccacctc aaaaggaacc tttccaggtc cccctggaaa ttgtgccctg   2940
gagatgttta acaaggagaa ctggtgagga aagagtcctt ttttactgta gggaaaagcc   3000
ccaaactggc ctcctggggg atgagggctg aaatgatccc gaaggccttt taattagtgt   3060
gaaatcctgc tgtactcaga aatccttccc cgaatttaca gcacaggcag gatgacctaa   3120
gaggcagttt acttccctga gacccacagt tgggctgttc tggaaacaca tctgtgaatc   3180
atagccaatt gccacagaga aaacagaacc aagcctccgg tgaggccact ccaccccaga   3240
gaagtctgca gaattccaag gactcggatt ggatgttcag aattcagcaa ctggaaagtc   3300
cttaaaaaca aacaggccaa accaaatcaa tattgctgtt tctagatgtc ccttctgtgg   3360
ttgagctagt tttacagaga taaatatatt aagacaagga ggtgggggtg ttatatgatc   3420
aatgatagcc atttgaaaga gagggaggag tacagaagga aggcacttct gggtacttaa   3480
ttcagaaatt tctttatatt tcagcactgg attatcatat aatgcaagtg actatggact   3540
aagagttagt tatggtgtct tatgactaga tttattatgg tatattaaag taacaataat   3600
attaatatta ccttcctttt tttttttgtt tcaaaagaga tctttctcca gatgcttcag   3660
cctgtctggc cttcttatca tatgtgcagc acatcatgtc tcagcaacag tgtggtgagg   3720
tccttaggtg tcccaagaac aactcaggga gcacgggagg gtctgcagtt gggaccccac   3780
aactatacag ctatagggta ggaggcttcc ttttcattgg tcctgaatga atacaaatcg   3840
ctcagaaagc attttggtgg cacagaaagg ggatgtattt gtgttgagat cttattttat   3900
tttgtattta tttatcttct ttgacttgca cagcactatt gggggtgggg gaagcagggt   3960
agtgggagac gaaggcagaa gcaagagtca aactcagaat gactgagttg aattcactgt   4020
ctagtcagca atgcctgctt ctgagtttgg cccagagaga aggtattgag taagatttta   4080
ataactgtaa aaagtaagct ggataagtaa aatcatgatg gatccaaagc acagtttctt   4140
catctcctga taaagaaagt caaatgcttg ataaattcag agtcacagat gtgagcatag   4200
```

ctatattctt ttaaacgaga ggtagagtga cctagcacta agcaaatgag ctgaaatgtc 4260
ggaaacagag tccatcagct tatttggcca cacgatccca aactagtttt atcttgggaa 4320
atggccctgt cctcagcatt cccttcttgt gctggtgggg ccagtgaagt cttgatctta 4380
tcagaaaaag gccacaccaa gtgcgagttt tcccaggctg actttccagg cccttatcaa 4440
atgaaacaac agaagctctt cacagttctg tgccccatgg ccactccaca gacagacaat 4500
accaagcatc ttagaactgt cataagatag gtcatgcctg aaatagatct tgaccatatg 4560
agagtcccag aaatcagcaa ggcctggaca aatagaacta agagagaggc agaggcagga 4620
agctgcgggt ctatcttgta aagagtttag catcactgtg agagtgtgtg tctaaaatta 4680
aattaaacta gaagcagcag gtgagtattt ggtaagtact tctgtgactc gcctcaattc 4740
ccactggcca ggggccatct caactgcacg gtgaatcaag atgctggtgt catcctcctt 4800
ggaaaaagga aatgttaact catggttaaa actaagtaca atgattccca agggatcact 4860
ttcttatttt tttaaatgac attaaggaga atcttaagaa agcatcagag aaagacatgt 4920
gcatgtgaag caccctgatt ctgatgttag gaaaacttaa gcgaacagga cctgctgcac 4980
acagccccat tgtcttctat ccatttctct ttatcattca aatcaagcaa catgtgccct 5040
cctcatcaac acacattctt cccctttgtc agtatgcatc tcccagctta gtgtcaggat 5100
actttcgatt cataattatg tatgatccaa agtgtgcata atttcattta acgttaaaga 5160
aatagatcca attcctttct tgcaaccaaa aataaataaa atacgttgcc tcaatataag 5220
gtttgggcta ttctgtgttt ctatagaagc aatctgtttt tggtaaaatg tacttttaag 5280
gatccagtca tctgaagtat tttatgtaga gttagagatt tcacaatatt gactatacat 5340
atatttaaaa tataaattat ccagctgatg tttgaatttg tcttactttc ctggccacct 5400
cgttgtccta ttttataagc tggggagtta actagcttaa caaaagatgc ttagcttttg 5460
taaaagaaca agtgtttcat tttacaaaga cactccaaat gatagttact tgattttctc 5520
gagaccttta actatggtga tgaataacag gacttgcttt caagccttaa taaatgtaaa 5580
atgcctttta atgaagatac agctgagtgt tttcctcatg aatctgaacc aattaccaat 5640
ttgtgttcca gtcttgattg gtattgactg attcaaataa agttggttta ttttcaaata 5700
tta 5703

<210> SEQ ID NO 18
<211> LENGTH: 1941
<212> TYPE: DNA
<213> ORGANISM: Homo sapiens

<400> SEQUENCE: 18
gcttttgtgg cggcgcccgc gctcgcaggc cactctctgc tgtcgcccgt cccgcgcgct 60
cctccgaccc gctccgctcc gctccgctcg gccccgcgcc gcccgtcaac atgatccgct 120
gcggcctggc ctgcgagcgc tgccgctgga tcctgcccct gctcctactc agcgccatcg 180
ccttcgacat catcgcgctg gccggccgcg gctggttgca gtctagcgac cacggccaga 240
cgtcctcgct gtggtggaaa tgctcccaag agggcggcgg cagcgggtcc tacgaggagg 300
gctgtcagag cctcatggag tacgcgtggg gtagagcagc ggctgccatg ctcttctgtg 360
gcttcatcat cctggtgatc tgtttcatcc tctccttctt cgccctctgt ggaccccaga 420
tgcttgtctt cctgagagtg attggaggtc tccttgcctt ggctgctgtg ttccagatca 480
tctccctggt aatttacccc gtgaagtaca cccagacctt cacccttcat gccaaccctg 540

-continued

```
ctgtcactta catctataac tgggcctacg gctttgggtg ggcagccacg attatcctga    600
ttggctgtgc cttcttcttc tgctgcctcc ccaactacga agatgacctt ctgggcaatg    660
ccaagcccag gtacttctac acatctgcct aacttgggaa tgaatgtggg agaaaatcgc    720
tgctgctgag atggactcca gaagaagaaa ctgtttctcc aggcgacttt gaacccattt    780
tttggcagtg ttcatattat taaactagtc aaaaatgcta aaataatttg ggagaaaata    840
tttttaagt agtgttatag tttcatgttt atcttttatt atgttttgtg aagttgtgtc    900
ttttcactaa ttacctatac tatgccaata tttcctatct atccataaca tttatactac    960
atttgtaaga gaatatgcac gtgaaactta acactttata aggtaaaaat gaggtttcca   1020
agatttaata atctgatcaa gttcttgtta tttccaaata gaatggactc ggtctgttaa   1080
gggctaagga gaagaggaag ataaggttaa aagttgttaa tgaccaaaca ttctaaaaga   1140
aatgcaaaaa aaaagtttat tttcaagcct tcgaactatt taaggaaagc aaaatcattt   1200
cctaaatgca tatcatttgt gagaatttct cattaatatc ctgaatcatt cattttagct   1260
aaggcttcat gttgactcga tatgtcatct aggaaagtac tatttcatgg tccaaacctg   1320
ttgccatagt tggtaaggct ttcctttaag tgtgaaatat ttagatgaaa ttttctcttt   1380
taaagttctt tatagggtta gggtgtggga aaatgctata ttaataaatc tgtagtgttt   1440
tgtgtttata tgttcagaac cagagtagac tggattgaaa gatggactgg gtctaattta   1500
tcatgactga tagatctgtt aagttgtgta gtaaagcatt aggagggtca ttcttgtcac   1560
aaaagtgcca ctaaaacagc ctcaggagaa taaatgactt gcttttctaa atctcaggtt   1620
tatctgggct ctatcatata gacaggcttc tgatagtttg caactgtaag cagaaaccta   1680
catatagtta aaatcctggt ctttcttggt aaacagattt taaatgtctg atataaaaca   1740
tgccacagga gaattcgggg atttgagttt ctctgaatag catatatatg atgcatcgga   1800
taggtcatta tgatttttta ccatttcgac ttacataatg aaaaccaatt cattttaaat   1860
atcagattat tattttgtaa gttgtggaaa aagctaattg tagttttcat tatgaagttt   1920
tcccaataaa ccaggtattc t                                              1941
```

<210> SEQ ID NO 19
<211> LENGTH: 2660
<212> TYPE: DNA
<213> ORGANISM: Homo sapiens

<400> SEQUENCE: 19

```
aggaagagcc gcgggcccgg cggctgaggc cacccccggcg gcggctggag agcgaggagg     60
agcgggtggc cccgcgctgc gcccgccctc gcctcacctg gcgcaggtgg acacctgcgc    120
aggtgtgtgc cctccggccc ctgaagcatg gccagcagcg gcatggctga cagcgccaac    180
cacctgccct tctttttcgg caacatcacc cgggaggagg cagaagatta cctggtccag    240
gggggcatga gtgatgggct ttatttgctg cgccagagcc gcaactacct gggtggcttc    300
gccctgtccg tggcccacgg gaggaaggca caccactaca ccatcgagcg ggagctgaat    360
ggcacctacg ccatcgccgg tggcaggacc catgccagcc ccgccgacct ctgccactac    420
cactcccagg agtctgatgg cctggtctgc ctcctcaaga agcccttcaa ccggccccaa    480
ggggtgcagc ccaagactgg gcccctttgag gatttgaagg aaaacctcat cagggaatat    540
gtgaagcaga catggaacct gcagggtcag gctctggagc aggccatcat cagtcagaag    600
cctcagctgg agaagctgat cgctaccaca gcccatgaaa aatgccttgg gttccatgga    660
aaaatctctc gggaagaatc tgagcaaatt gtcctgatag gatcaaagac aaatggaaag    720
```

ttcctgatcc gagccagaga caacaacggc tcctacgccc tgtgcctgct gcacgaaggg 780
aaggtgctgc actatcgcat cgacaaagac aagacaggga agctctccat ccccgaggga 840
aagaagttcg acacgctctg gcagctagtc gagcattatt cttataaagc agatggtttg 900
ttaagagttc ttactgtccc atgtcaaaaa atcggcacac agggaaatgt taattttgga 960
ggccgtccac aacttccagg ttcccatcct gcgacttggt cagcgggtgg aataatctca 1020
agaatcaaat catactcctt cccaaagcct ggccacagaa agtcctcccc tgcccaaggg 1080
aaccggcaag agagtactgt gtcattcaat ccgtatgagc cagaacttgc accctgggct 1140
gcagacaaag gcccccagag agaagcccta cccatggaca cagaggtgta cgagagcccc 1200
tacgcggacc ctgaggagat caggcccaag gaggtttacc tggaccgaaa gctgctgacg 1260
ctggaagaca aagaactggg ctctggtaat tttggaactg tgaaaaaggg ctactaccaa 1320
atgaaaaaag ttgtgaaaac cgtggctgtg aaaatactga aaaacgaggc caatgacccc 1380
gctcttaaag atgagttatt agcagaagca aatgtcatgc agcagctgga caacccgtac 1440
atcgtgcgca tgatcgggat atgcgaggcc gagtcctgga tgctagttat ggagatggca 1500
gaacttggtc ccctcaataa gtatttgcag cagaacagac atgtcaagga taagaacatc 1560
atagaactgg ttcatcaggt ttccatgggc atgaagtact tggaggagag caattttgtg 1620
cacagagatc tggctgcaag aaatgtgttg ctagttaccc aacattatgc caagatcagt 1680
gatttcggac tctccaaagc actgcgtgct gatgaaaact actacaaggc ccagacccat 1740
ggaaagtggc ctgtcaagtg gtacgctccg gaatgcatca actactacaa gttctccagc 1800
aaaagcgatg tctggagctt tggagtgttg atgtgggaag cattctccta tgggcagaag 1860
ccatatcgag ggatgaaagg aagtgaagtc accgctatgt tagagaaagg agagcggatg 1920
gggtgccctg cagggtgtcc aagagagatg tacgatctca tgaatctgtg ctggacatac 1980
gatgtggaaa acaggcccgg attcgcagca gtggaactgc ggctgcgcaa ttactactat 2040
gacgtggtga actaaccgct cccgcacctg tcggtggctg cctttgatca caggagcaat 2100
cacaggaaaa tgtatccaga ggaattgatt gtcagccacc tccctctgcc agtcgggaga 2160
gccaggcttg gatggaacat gcccacaact tgtcacccaa agcctgtccc aggactcacc 2220
ctccacaaag caaaggcagt cccgggagaa aagacggatg gcaggatcca aggggctagc 2280
tggatttgtt tgttttcttg tctgtgtgat tttcatacag gttattttta cgatctgttt 2340
ccaaatccct ttcatgtctt tccacttctc tgggtcccgg ggtgcatttg ttactcatcg 2400
ggcccaggga cattgcagag tggcctagag cactctcacc ccaagcggcc ttttccaaat 2460
gcccaaggat gccttagcat gtgactcctg aagggaaggc aaaggcagag gaatttggct 2520
gcttctacgg ccatgagact gatccctggc cactgaaaag ctttcctgac aataaaaatg 2580
ttttgaggct ttaaaaagaa aatcaagttt gaccagtgca gtttctaagc atgtagccag 2640
ttaaggaaag aaagaaaaaa 2660

<210> SEQ ID NO 20
<211> LENGTH: 6860
<212> TYPE: DNA
<213> ORGANISM: Homo sapiens

<400> SEQUENCE: 20
ggtggcctct gtggccgtcc aggctagcgg cggcccgcag gcggcgggga gaaagactct 60
ctcacctggt cttgcggctg tggccaccgc cggccagggg tgtggagggc gtgctgccgg 120

-continued

```
agacgtccgc cgggctctgc agttccgccg ggggtcgggc agctatggag ccgcggccca    180
cggcgccctc ctccggcgcc ccgggactgg ccggggtcgg ggagacgccg tcagccgctg    240
cgctggccgc agccagggtg gaactgcccg gcacggctgt gccctcggtg ccggaggatg    300
ctgcgcccgc gagccgggac ggcggcgggg tccgcgatga gggcccccgcg gcggccgggg    360
acgggctggg cagacccttg gggcccaccc cgagccagag ccgtttccag gtggacctgg    420
tttccgagaa cgccgggcgg gccgctgctg cggcggcggc ggcggcggcg gcagcggcgg    480
cggctggtgc tggggcgggg gccaagcaga cccccgcgga cggggaagcc agcggcgaga    540
gcgagccggc taaaggcagc gaggaagcca agggccgctt ccgcgtgaac ttcgtggacc    600
cagctgcctc ctcgtcggct gaagacagcc tgtcagatgc tgccggggtc ggagtcgacg    660
ggcccaacgt gagcttccag aacggcgggg acacggtgct gagcgagggc agcagcctgc    720
actccggcgg cggcggcggc agtgggcacc accagcacta ctattatgat acccacacca    780
acacctacta cctgcgcacc ttcggccaca acaccatgga cgctgtgccc aggatcgatc    840
actaccggca cacagccgcg cagctgggcg agaagctgct ccggcctagc ctggcggagc    900
tccacgacga gctggaaaag gaaccttttg aggatggctt tgcaaatggg gaagaaagta    960
ctccaaccag agatgctgtg gtcacgtata ctgcagaaag taaaggagtc gtgaagtttg   1020
gctggatcaa gggtgtatta gtacgttgta tgttaaacat ttggggtgtg atgcttttca   1080
ttagattgtc atggattgtg ggtcaagctg gaataggtct atcagtcctt gtaataatga   1140
tggccactgt tgtgacaact atcacaggat tgtctacttc agcaatagca actaatggat   1200
ttgtaagagg aggaggagca tattatttaa tatctagaag tctagggcca gaatttggtg   1260
gtgcaattgg tctaatcttc gcctttgcca acgctgttgc agttgctatg tatgtggttg   1320
gatttgcaga aaccgtggtg gagttgctta aggaacattc catacttatg atagatgaaa   1380
tcaatgatat ccgaattatt ggagccatta cagtcgtgat tcttttaggt atctcagtag   1440
ctggaatgga gtgggaagca aaagctcaga ttgttctttt ggtgatccta cttcttgcta   1500
ttggtgattt cgtcatagga acatttatcc cactggagag caagaagcca aaagggtttt   1560
ttggttataa atctgaaata tttaatgaga actttgggcc cgattttcga gaggaagaga   1620
ctttcttttc tgtatttgcc atctttttc ctgctgcaac tggtattctg gctggagcaa   1680
atatctcagg tgatcttgca gatcctcagt cagccatacc caaaggaaca ctcctagcca   1740
ttttaattac tacattggtt tacgtaggaa ttgcagtatc tgtaggttct tgtgttgttc   1800
gagatgccac tggaaacgtt aatgacacta tcgtaacaga gctaacaaac tgtacttctg   1860
cagcctgcaa attaaacttt gatttttcat cttgtgaaag cagtccttgt tcctatggcc   1920
taatgaacaa cttccaggta atgagtatgg tgtcaggatt tacaccacta atttctgcag   1980
gtatattttc agccactctt tcttcagcat tagcatccct agtgagtgct cccaaaatat   2040
ttcaggctct atgtaaggac aacatctacc cagctttcca gatgtttgct aaaggttatg   2100
ggaaaaataa tgaacctctt cgtggctaca tcttaacatt cttaattgca cttggattca   2160
tcttaattgc tgaactgaat gttattgcac caattatctc aaacttcttc cttgcatcat   2220
atgcattgat caatttttca gtattccatg catcacttgc aaaatctcca ggatggcgtc   2280
ctgcattcaa atactacaac atgtggatat cacttcttgg agcaattctt tgttgcatag   2340
taatgttcgt cattaactgg tgggctgcat tgctaacata tgtgatagtc cttgggctgt   2400
atatttatgt tacctacaaa aaaccagatg tgaattgggg atcctctaca caagccctga   2460
cttacctgaa tgcactgcag cattcaattc gtctttctgg agtggaagac cacgtgaaaa   2520
```

-continued actttaggcc acagtgtctt gttatgacag gtgctccaaa ctcacgtcca gctttacttc 2580
atcttgttca tgatttcaca aaaaatgttg gtttgatgat ctgtggccat gtacatatgg 2640
gtcctcgaag acaagccatg aaagagatgt ccatcgatca agccaaatat cagcgatggc 2700
ttattaagaa caaaatgaag gcattttatg ctccagtaca tgcagatgac ttgagagaag 2760
gtgcacagta tttgatgcag gctgctggtc ttggtcgtat gaagccaaac acacttgtcc 2820
ttggatttaa gaaagattgg ttgcaagcag atatgaggga tgtggatatg tatataaact 2880
tatttcatga tgcttttgac atacaatatg gagtagtggt tattcgccta aaagaaggtc 2940
tggatatatc tcatcttcaa ggacaagaag aattattgtc atcacaagag aaatctcctg 3000
gcaccaagga tgtggtagta agtgtggaat atagtaaaaa gtccgattta gatacttcca 3060
aaccactcag tgaaaaacca attacacaca aagttgagga agaggatggc aagactgcaa 3120
ctcaaccact gttgaaaaaa gaatccaaag gccctattgt gcctttaaat gtagctgacc 3180
aaaagcttct tgaagctagt acacagtttc agaaaaaaca aggaaagaat actattgatg 3240
tctggtggct tttgatgat ggaggtttga ccttattgat accttacctt ctgacgacca 3300
agaaaaaatg gaaagactgt aagatcagag tattcattgg tggaaagata aacagaatag 3360
accatgaccg gagagcgatg gctactttgc ttagcaagtt ccggatagac ttttctgata 3420
tcatggttct aggagatatc aataccaaac caaagaaaga aaatattata gcttttgagg 3480
aaatcattga gccatacaga cttcatgaag atgataaaga gcaagatatt gcagataaaa 3540
tgaaagaaga tgaaccatgg cgaataacag ataatgagct tgaactttat aagaccaaga 3600
cataccggca gatcaggtta aatgagttat taaaggaaca ttcaagcaca gctaatatta 3660
ttgtcatgag tctcccagtt gcacgaaaag gtgctgtgtc tagtgctctc tacatggcat 3720
ggttagaagc tctatctaag gacctaccac caatcctcct agttcgtggg aatcatcaga 3780
gtgtccttac cttctattca taaatgttct atacagtgga cagccctcca gaatggtact 3840
tcagtgccta gtgtagtaac tgaaatcttc aatgacacat taacatcaca atggcgaatg 3900
gtgacttttc tttcacgatt tcattaattt gaaagcacac aggaaagttg ctccattgat 3960
aacgtgtatg gagacttcgg ttttagtcaa ttccatatct caatcttaat ggtgattctt 4020
ctctgttgaa ctgaagtttg tgagagtagt tttcctttgc tacttgaata gcaataaaag 4080
cgtgttaact ttttgattga tgaaagaagt acaaaaagcc tttagccttg aggtgccttc 4140
tgaaattaac caaatttcat ccatatatcc tcttttataa acttatagaa tgtcaaactt 4200
tgccttcaac tgtttttatt tctagtctct tccactttaa aacaaaatga acactgcttg 4260
tcttcttcca ttgaccattt agtgttgagt actgtatgtg ttttgttaat tctataaagg 4320
tatctgttag atattaaagg tgagaattag ggcaggttaa tcaaaaatgg ggaaggggaa 4380
atggtaacca aaaagtaacc ccatggtaag gtttatatga gtatatgtga atatagagct 4440
aggaaaaaaa gcccccccaa atacctttt aacccctctg attggctatt attactatat 4500
ttattattat ttattgaaac cttagggaag attgaagatt catcccatac ttctatatac 4560
catgcttaaa aatcacgtca ttctttaaac aaaaatactc aagatcattt atatttattt 4620
ggagagaaaa ctgtcctaat ttagaatttc cctcaaatct gagggacttt taagaaatgc 4680
taacagattt ttctggagga aatttagaca aaacaatgtc atttagtaga atatttcagt 4740
atttaagtgg aatttcagta tactgtacta tcctttataa gtcattaaaa taatgtttca 4800
tcaaatggtt aaatggacca ctggtttctt agagaaatgt ttttaggctt aattcattca 4860

-continued attgtcaagt acacttagtc ttaatacact caggtttgaa cagattattc tgaatattaa 4920
aatttaatcc attcttaata ttttaaaact tttgttaaga aaaactgcca gtttgtgctt 4980
ttgaaatgtc tgttttgaca tcatagtcta gtaaaatttt gacagtgcat atgtactgtt 5040
actaaaagct ttatatgaaa ttattaatgt gaagtttttc atttataatt caaggaagga 5100
tttcctgaaa acatttcaag ggatttatgt ctacatattt gtgtgtgtgt gtgtatatat 5160
atgtaatatg catacacaga tgcatatgtg tatatataat gaaatttatg ttgctggtat 5220
tttgcatttt aaagtgatca agattcatta ggcaaacttt ggtttaagta aacatatgtt 5280
caaaatcaga ttaacagata caggtttcat agagaacaaa ggtgatcatt tgaagggcat 5340
gctgtaattt cacacaattt tccagttcaa aaatggagaa tacttcgcct aaaatactgt 5400
taagtgggtt aattgataca agtttctgtg gtggaaaatt tatgcaggtt ttcacgaatc 5460
cttttttttt tttttttttt tttttgagac ggagtcttgc tctgttgcca cgctggaatg 5520
cagtaacgtg atcttggctc actgcgacct ccacctcccc agttcaagcg attctcctgc 5580
ctcagcctcc ctagtagctg ggactacggg tgcacgccac catgcccagc taatttttgt 5640
attttgagta gagacagggt ttcaccgtgt tggctaggat ggtgtctatc tcttgacctt 5700
gtgatccacc cgcctcagcc tcccagagtg ctgggattac aggtgcgagc cactgcgcct 5760
ggctggtttt catgaatctt gatagacatc tataacgtta ttattttcag tggtgtgcag 5820
catttttgct tcatgagtat gacctaggta tagagatctg ataacttgaa ttcagaatat 5880
taagaaaatg aagtaactga ttttctaaaa aaaaaaaaaa aaaaaatttc tacattataa 5940
ctcacagcat tgttccattg caggttttgc aatgtttggg ggtaaagaca gtagaaatat 6000
tattcagtaa acaataatgt gtgaactttt aagatggata atagggcatg gactgagtgc 6060
tgctatcttg aaatgtgcac aggtacactt accttttttt tttttttttt taagtttttc 6120
ccattcagga aaacaacatt gtgatctgta ctacaggaac caaatgtcat gcgtcataca 6180
tgtgggtata aagtacataa aatatatcta actattcata atgtggggtg ggtaatactg 6240
tctgtgaaat aatgtaagaa gcttttcact taaaaaaaat gcattacttt cacttaacac 6300
tagacaccag gtcgaaaatt ttcaaggtta tagtacttat ttcaacaatt cttagagatg 6360
ctagctagtg ttgaagctaa aaatagcttt atttatgctg aattgtgatt tttttatgcc 6420
aaattttttt tagttctaat cattgatgat agcttggaaa taaataatta tgccatggca 6480
tttgacagtt cattattcct ataagaatta aattgagttt agagagaatg gtggtgttga 6540
gctgattatt aacagttact gaaatcaaat atttatttgt tacattattc catttgtatt 6600
ttaggtttcc ttttacattc tttttatatg cattctgaca ttacatattt tttaagacta 6660
tggaaataat ttaaagattt aagctctggt ggatgattat ctgctaagta agtctgaaaa 6720
tgtaatattt tgataatact gtaatatacc tgtcacacaa atgcttttct aatgttttaa 6780
ccttgagtat tgcagttgct gctttgtaca gaggttactg caataaagga agtggattca 6840
ttaaacctat ttaatgtcca 6860

<210> SEQ ID NO 21
<211> LENGTH: 3745
<212> TYPE: DNA
<213> ORGANISM: Homo sapiens

<400> SEQUENCE: 21
cgcaaagcaa gtgggcacaa ggagtatggt tctaacgtga ttggggtcat gaagacgttg 60
ctgttggact tggctttgtg gtcactgctc ttccagcccg ggtggctgtc ctttagttcc 120

-continued

```
caggtgagtc agaactgcca caatggcagc tatgaaatca gcgtcctgat gatgggcaac    180
tcagcctttg cagagcccct gaaaaacttg gaagatgcgg tgaatgaggg gctggaaata    240
gtgagaggac gtctgcaaaa tgctggccta aatgtgactg tgaacgctac tttcatgtat    300
tcggatggtc tgattcataa ctcaggcgac tgccggagta gcacctgtga aggcctcgac    360
ctactcagga aaatttcaaa tgcacaacgg atgggctgtg tcctcatagg gccctcatgt    420
acatactcca ccttccagat gtaccttgac acagaattga gctaccccat gatctcagct    480
ggaagttttg gattgtcatg tgactataaa gaaaccttaa ccaggctgat gtctccagct    540
agaaagttga tgtacttctt ggttaacttt tggaaaacca acgatctgcc cttcaaaact    600
tattcctgga gcacttcgta tgtttacaag aatggtacag aaactgagga ctgtttctgg    660
taccttaatg ctctggaggc tagcgtttcc tatttctccc acgaactcgg ctttaaggtg    720
gtgttaagac aagataagga gtttcaggat atcttaatgg accacaacag gaaaagcaat    780
gtgattatta tgtgtggtgg tccagagttc ctctacaagc tgaagggtga ccgagcagtg    840
gctgaagaca ttgtcattat tctagtggat cttttcaatg accagtactt ggaggacaat    900
gtcacagccc ctgactatat gaaaaatgtc cttgttctga cgctgtctcc tgggaattcc    960
cttctaaata gctctttctc caggaatcta tcaccaacaa aacgagactt tgctcttgcc   1020
tatttgaatg gaatcctgct ctttggacat atgctgaaga tatttcttga aaatggagaa   1080
aatattacca cccccaaatt tgctcatgct ttcaggaatc tcacttttga agggtatgac   1140
ggtccagtga ccttggatga ctgggggat gttgacagta ccatggtgct tctgtatacc   1200
tctgtggaca ccaagaaata caaggttctt ttgacctatg atacccacgt aaataagacc   1260
tatcctgtgg atatgagccc cacattcact tggaagaact ctaaacttcc taatgatatt   1320
acaggccggg gccctcagat cctgatgatt gcagtcttca ccctcactgg agctgtggtg   1380
ctgctcctgc tcgtcgctct cctgatgctc agaaaatata gaaaagatta tgaacttcgt   1440
cagaaaaaat ggtcccacat tcctcctgaa aatatctttc ctctggagac caatgagacc   1500
aatcatgtta gcctcaagat cgatgatgac aaaagacgag atacaatcca gagactacga   1560
cagtgcaaat acgacaaaaa gcgagtgatt ctcaaagatc tcaagcacaa tgatggtaat   1620
ttcactgaaa aacagaagat agaattgaac aagttgcttc agattgacta ttacaacctg   1680
accaagttct acggcacagt gaaacttgat accatgatct tcggggtgat agaatactgt   1740
gagagaggat ccctccggga agttttaaat gacacaattt cctaccctga tggcacattc   1800
atggattggg agtttaagat ctctgtcttg tatgacattg ctaagggaat gtcatatctg   1860
cactccagta agacagaagt ccatggtcgt ctgaaatcta ccaactgcgt agtggacagt   1920
agaatggtgg tgaagatcac tgattttggc tgcaattcca ttttacctcc aaaaaaggac   1980
ctgtggacag ctccagagca cctccgccaa gccaacatct ctcagaaagg agatgtgtac   2040
agctatggga tcatcgcaca ggagatcatt ctgcggaaag aaaccttcta cactttgagc   2100
tgtcgggacc ggaatgagaa gattttcaga gtggaaaatt ccaatggaat gaaacccttc   2160
cgcccagatt tattcttgga aacagcagag gaaaaagagc tagaagtgta cctacttgta   2220
aaaaactgtt gggaggaaga tccagaaaag agaccagatt tcaaaaaaat tgagactaca   2280
cttgccaaga tatttggact tttcatgac caaaaaaatg aaagctatat ggataccttg   2340
atccgacgtc tacagctata ttctcgaaac ctggaacatc tggtagagga aaggacacag   2400
ctgtacaagg cagagaggga cagggctgac agacttaact ttatgttgct tccaaggcta   2460
```

```
gtggtaaagt ctctgaagga gaaaggcttt gtggagccgg aactatatga ggaagttaca   2520
atctacttca gtgacattgt aggtttcact actatctgca aatacagcac cccatggaa    2580
gtggtggaca tgcttaatga catctataag agttttgacc acattgttga tcatcatgat   2640
gtctacaagg tggaaaccat cggtgatgcg tacatggtgg ctagtggttt gcctaagaga   2700
aatggcaatc ggcatgcaat agacattgcc aagatggcct tggaaatcct cagcttcatg   2760
gggacctttg agctggagca tcttcctggc ctcccaatat ggattcgcat tggagttcac   2820
tctggtccct gtgctgctgg agttgtggga atcaagatgc ctcgttattg tctatttgga   2880
gatacggtca acacagcctc taggatggaa tccactggcc tccctttgag aattcacgtg   2940
agtggctcca ccatagccat cctgaagaga actgagtgcc agttccttta tgaagtgaga   3000
ggagaaacat acttaaaggg aagaggaaat gagactacct actggctgac tgggatgaag   3060
gaccagaaat tcaacctgcc aacccctcct actgtggaga atcaacagcg tttgcaagca   3120
gaattttcag acatgattgc caactcttta cagaaaagac aggcagcagg gataagaagc   3180
caaaaaccca gacgggtagc cagctataaa aaaggcactc tggaatactt gcagctgaat   3240
accacagaca aggagagcac ctatttttaa acctaaatga ggtataagga ctcacacaaa   3300
ttaaaataca gctgcactga ggcagcgacc tcaagtgtcc tgaaagctta cattttcctg   3360
agacctcaat gaagcagaaa tgtacttagg cttggctgcc ctgtctggaa catggacttt   3420
cttgcatgaa tcagatgtgt gttctcagtg aaataactac cttccactct ggaaccttat   3480
tccagcagtt gttccaggga gcttctacct ggaaaagaaa agaaatgaat agactatcta   3540
gaacttgaga agattttatt cttatttcat ttatttttg tttgtttatt tttatcgttt    3600
ttgtttactg gctttccttc tgtattcata agatttttta aattgtcata attatatttt   3660
aaataccat cttcattaaa gtatatttaa ctcataattt ttgcagaaaa tatgctatat    3720
attaggcaag aataaaagct aaagg                                         3745
```

<210> SEQ ID NO 22
<211> LENGTH: 1428
<212> TYPE: DNA
<213> ORGANISM: Homo sapiens

<400> SEQUENCE: 22

```
cttcaggtca gggagaatgt ataaatgtcc attgccatcg aggttctgct atttttgaga     60
agctgaagca actccaagga cacagttcac agaaatttgg ttctcagccc caaaatactg    120
attgaattgg agacaattac aaggactctc tggccaaaaa cccttgaaga ggccccgtga    180
aggaggcagt gaggagcttt tgattgctga cctgtgtcgt accaccccag aatgtgcact    240
gggggctgtg ccagatgcct ggggggggacc ctcattcccc ttgctttttt tggcttcctg   300
gctaacatcc tgttattttt tcctggagga aaagtgatag atgacaacga ccacctttcc    360
caagagatct ggtttttcgg aggaatatta ggaagcggtg tcttgatgat cttccctgcg    420
ctggtgttct tgggcctgaa gaacaatgac tgctgtgggt gctgcggcaa cgagggctgt    480
gggaagcgat ttgcgatgtt cacctccacg atatttgctg tggttggatt cttgggagct    540
ggatactcgt ttatcatctc agccatttca atcaacaagg gtcctaaatg cctcatggcc    600
aatagtacat ggggctaccc cttccacgac ggggattatc tcaatgatga ggccttatgg    660
aacaagtgcc gagagcctct caatgtggtt ccctggaatc tgaccctctt ctccatcctg    720
ctggtcgtag gaggaatcca gatggttctc tgcgccatcc aggtggtcaa tggcctcctg    780
gggaccctct gtggggactg ccagtgttgt ggctgctgtg gggagatgg acccgtttaa     840
```

-continued acctccgaga tgagctgctc agactctaca gcatgacgac tacaatttct tttcataaaa 900
cttcttctct tcttggaatt attaattcct atctgcttcc tagctgataa agcttagaaa 960
aggcagttat tccttctttc caaccagctt tgctcgagtt agaattttgt tattttcaaa 1020
taaaaaatag tttggccact taacaaattt gatttataaa tctttcaaat tagttccttt 1080
ttagaattta ccaacaggtt caaagcatac ttttcatgat ttttttatta caaatgtaaa 1140
atgtataaag tcacatgtac tgccatacta cttctttgta tataaagatg tttatatctt 1200
tggaagtttt acataaatca aaggaagaaa gcacatttaa aatgagaaac taagaccaat 1260
ttctgttttt aagaggaaaa agaatgattg atgtatccta agtattgtta tttgttgtct 1320
ttttttgctg ccttgcttga gttgcttgtg actgatcttt tgaggctgtc atcatggcta 1380
gggttctttt atgtatgtta aattaaaacc tgaattcaga ggtaacgt 1428

<210> SEQ ID NO 23
<211> LENGTH: 4090
<212> TYPE: DNA
<213> ORGANISM: Homo sapiens

<400> SEQUENCE: 23
ctggagagcc tgctgcccgc ccgcccgtaa aatggtcccc tcggctggac agctcgccct 60
gttcgctctg ggtattgtgt tggctgcgtg ccaggccttg gagaacagca cgtccccgct 120
gagtgcagac ccgcccgtgg ctgcagcagt ggtgtcccat tttaatgact gcccagattc 180
ccacactcag ttctgcttcc atggaacctg caggtttttg gtgcaggagg acaagccagc 240
atgtgtctgc cattctgggt acgttggtgc acgctgtgag catgcggacc tcctggccgt 300
ggtggctgcc agccagaaga agcaggccat caccgccttg gtggtggtct ccatcgtggc 360
cctggctgtc cttatcatca catgtgtgct gatacactgc tgccaggtcc gaaaacactg 420
tgagtggtgc cgggccctca tctgccggca cgagaagccc agcgccctcc tgaagggaag 480
aaccgcttgc tgccactcag aaacagtggt ctgaagagcc cagaggagga gtttggccag 540
gtggactgtg gcagatcaat aaagaaaggc ttcttcagga cagcactgcc agagatgcct 600
gggtgtgcca cagaccttcc tacttggcct gtaatcacct gtgcagcctt ttgtgggcct 660
tcaaaactct gtcaagaact ccgtctgctt ggggttattc agtgtgacct agagaagaaa 720
tcagcggacc acgatttcaa gacttgttaa aaaagaactg caaagagacg gactcctgtt 780
cacctaggtg aggtgtgtgc agcagttggt gtctgagtcc acatgtgtgc agttgtcttc 840
tgccagccat ggattccagg ctatatattt ctttttaatg ggccacctcc ccacaacaga 900
attctgccca acacaggaga tttctatagt tattgttttc tgtcatttgc ctactgggga 960
agaaagtgaa ggaggggaaa ctgtttaata tcacatgaag accctagctt taagagaagc 1020
tgtatcctct aaccacgaga ctctcaacca gcccaacatc ttccatggac acatgacatt 1080
gaagaccatc ccaagctatc gccacccttg gagatgatgt cttatttatt agatggataa 1140
tggttttatt tttaatctct taagtcaatg taaaaagtat aaaacccctt cagacttcta 1200
cattaatgat gtatgtgttg ctgactgaaa agctatactg attagaaatg tctggcctct 1260
tcaagacagc taaggcttgg gaaaagtctt ccagggtgcg gagatggaac cagaggctgg 1320
gttactggta ggaataaagg taggggttca gaaatggtgc cattgaagcc acaaagccgg 1380
taaatgcctc aatacgttct gggagaaaac ttagcaaatc catcagcagg gatctgtccc 1440
ctctgttggg gagagaggaa gagtgtgtgt gtctacacag gataaaccca atacatattg 1500

-continued

```
tactgctcag tgattaaatg ggttcacttc ctcgtgagcc ctcggtaagt atgtttagaa   1560
atagaacatt agccacgagc cataggcatt tcaggccaaa tccatgaaag gggaccagt    1620
catttatttt ccattttgtt gcttggttgg tttgttgctt tatttttaaa aggagaagtt   1680
taactttgct atttattttc gagcactagg aaaactattc cagtaatttt tttttcctca   1740
tttccattca ggatgccggc tttattaaca aaaactctaa caagtcacct ccactatgtg   1800
ggtcttcctt tcccctcaag agaaggagca attgttcccc tgacatctgg gtccatctga   1860
cccatggggc ctgcctgtga gaaacagtgg gtcccttcaa atacatagtg gatagctcat   1920
ccctaggaat tttcattaaa atttggaaac agagtaatga agaaataata tataaactcc   1980
ttatgtgagg aaatgctact aatatctgaa aagtgaaaga tttctatgta ttaactctta   2040
agtgcaccta gcttattaca tcgtgaaagg tacatttaaa atatgttaaa ttggcttgaa   2100
attttcagag aattttgtct tcccctaatt cttcttcctt ggtctggaag aacaatttct   2160
atgaatttc tctttatttt ttttttataa ttcagacaat tctatgaccc gtgtcttcat    2220
ttttggcact cttatttaac aatgccacac ctgaagcact tggatctgtt cagagctgac   2280
cccctagcaa cgtagttgac acagctccag gtttttaaat tactaaaata agttcaagtt   2340
tacatccctt gggccagata tgtgggttga ggcttgactg tagcatcctg cttagagacc   2400
aatcaatgga cactggtttt tagacctcta tcaatcagta gttagcatcc aagagacttt   2460
gcagaggcgt aggaatgagg ctggacagat ggcggaacga gaggttccct gcgaagactt   2520
gagatttagt gtctgtgaat gttctagttc ctaggtccag caagtcacac ctgccagtgc   2580
cctcatcctt atgcctgtaa cacacatgca gtgagaggcc tcacatatac gcctccctag   2640
aagtgccttc caagtcagtc ctttggaaac cagcaggtct gaaaaagagg ctgcatcaat   2700
gcaagcctgg ttggaccatt gtccatgcct caggatagaa cagcctggct tatttgggga   2760
tttttcttct agaaatcaaa tgactgataa gcattggctc cctctgccat ttaatggcaa   2820
tggtagtctt tggttagctg caaaaatact ccatttcaag ttaaaaatgc atcttctaat   2880
ccatctctgc aagctccctg tgtttccttg ccctttagaa aatgaattgt tcactacaat   2940
tagagaatca tttaacatcc tgacctggta agctgccaca cacctggcag tggggagcat   3000
cgctgtttcc aatggctcag gagacaatga aaagccccca tttaaaaaaa taacaaacat   3060
tttttaaaag gcctccaata ctcttatgga gcctggattt ttcccactgc tctacaggct   3120
gtgacttttt ttaagcatcc tgacaggaaa tgttttcttc tacatggaaa gatagacagc   3180
agccaaccct gatctggaag acagggcccc ggctggacac acgtggaacc aagccaggga   3240
tgggctggcc attgtgtccc cgcaggagag atgggcagaa tggccctaga gttcttttcc   3300
ctgagaaagg agaaaaagat gggattgcca ctcacccacc cacactggta agggaggaga   3360
atttgtgctt ctggagcttc tcaagggatt gtgttttgca ggtacagaaa actgcctgtt   3420
atcttcaagc caggttttcg agggcacatg ggtcaccagt tgctttttca gtcaatttgg   3480
ccgggatgga ctaatgaggc tctaacactg ctcaggagac ccctgccctc tagttggttc   3540
tgggctttga tctcttccaa cctgcccagt cacagaagga ggaatgactc aaatgcccaa   3600
aaccaagaac acattgcaga agtaagacaa acatgtatat ttttaaatgt tctaacataa   3660
gacctgttct ctctagccat tgatttacca ggctttctga aagatctagt ggttcacaca   3720
gagagagaga gagtactgaa aaagcaactc ctcttcttag tcttaataat ttactaaaat   3780
ggtcaacttt tcattatctt tattataata aacctgatgc tttttttag aactccttac    3840
tctgatgtct gtatatgttg cactgaaaag gttaatattt aatgttttaa tttattttgt   3900
```

gtggtaagtt aattttgatt tctgtaatgt gttaatgtga ttagcagtta ttttccttaa 3960
tatctgaatt atacttaaag agtagtgagc aatataagac gcaattgtgt ttttcagtaa 4020
tgtgcattgt tattgagttg tactgtacct tatttggaag gatgaaggaa tgaacctttt 4080
tttcctaaaa 4090

<210> SEQ ID NO 24
<211> LENGTH: 1180
<212> TYPE: DNA
<213> ORGANISM: Homo sapiens

<400> SEQUENCE: 24
gaatagtcta cccccc ttgc actctacctg acacagctgc agcctgcaat tcactcgcac 60
tgcctgggat tgcactggat ccgtgtgctc agaacaaggt gaacgcccag ctgcagccat 120
gaagatctgt agcctcaccc tgctctcctt cctcctactg gctgctcagg tgctcctggt 180
ggaggggaaa aaaaaagtga agaatggact tcacagcaaa gtggtctcag aacaaaagga 240
cactctgggc aacacccaga ttaagcagaa aagcaggccc gggaacaaag gcaagtttgt 300
caccaaagac caagccaact gcagatgggc tgctactgag caggaggagg gcatctctct 360
caaggttgag tgcactcaat tggaccatga attttcctgt gtctttgctg gcaatccaac 420
ctcatgccta aagctcaagg atgagagagt ctattggaaa caagttgccc ggaatctgcg 480
ctcacagaaa gacatctgta gatattccaa gacagctgtg aaaaccagag tgtgcagaaa 540
ggattttcca gaatccagtc ttaagctagt cagctccact ctatttggga acacaaagcc 600
caggaaggag aaaacagaga tgtcccccag ggagcacatc aaaggcaaag agaccacccc 660
ctctagccta gcagtgaccc agaccatggc caccaaagct cccgagtgtg tggaggaccc 720
agatatggca aaccagagga agactgccct ggagttctgt ggagagactt ggagctctct 780
ctgcacattc ttcctcagca tagtgcagga cacgtcatgc taatgaggtc aaaagagaac 840
gggttccctt aagagatgtc atgtcgtaag tccctctgta tactttaaag ctctctacag 900
tccccccaaa atatgaactt ttgtgcttag tgagtgcaac gaaatattta aacaagtttt 960
gtattttttg cttttgtgtt ttggaatttg ccttattttt cttggatgcg atgttcagag 1020
gctgtttcct gcagcatgta tttccatggc ccacacagct atgtgtttga gcagcgaaga 1080
gtctttgagc tgaatgagcc agagtgataa tttcagtgca acgaactttc tgctgaatta 1140
atggtaataa aactctgggt gtttttcaga aatacattca 1180

<210> SEQ ID NO 25
<211> LENGTH: 2510
<212> TYPE: DNA
<213> ORGANISM: Homo sapiens

<400> SEQUENCE: 25
gctgggccac agcctggtcc tgccgctgcg cccgcccgcc atggtgtccc gggaccaggc 60
tcacctgggc cccaagtatg tgggcctctg ggacttcaag tcccggacgg acgaggagct 120
gagcttccgc gcgggggacg tcttccacgt ggccaggaag gaggagcagt ggtggtgggc 180
cacgctgctg gacgaggcgg gtggggccgt ggcccagggc tatgtgcccc acaactacct 240
ggccgagagg gagacggtgg agtcggaacc gtggttcttt ggctgcatct cccgctcgga 300
agctgtgcgt cggctgcagg ccgagggcaa cgccacgggc gccttcctga tcagggtcag 360
cgagaagccg agtgccgact acgtcctgtc ggtgcgggac acgcaggctg tgcggcacta 420
caagatctgg cggcgtgccg ggggccggct gcacctgaac gaggcggtgt ccttcctcag 480
cctgcccgag cttgtgaact accacagggc ccagagcctg tcccacggcc tgcggctggc 540
cgcgccctgc cggaagcacg agcctgagcc cctgccccat tgggatgact gggagaggcc 600
gagggaggag ttcacgctct gcaggaagct ggggtccggc tactttgggg aggtcttcga 660
ggggctctgg aaagaccggg tccaggtggc cattaaggtg atttctcgag acaacctcct 720
gcaccagcag atgctgcagt cggagatcca ggccatgaag aagctgcggc acaaacacat 780
cctggcgctg tacgccgtgg tgtccgtggg ggaccccgtg tacatcatca cggagctcat 840
ggccaagggc agcctgctgg agctgctccg cgactctgat gagaaagtcc tgcccgtttc 900
ggagctgctg gacatcgcct ggcaggtggc tgagggcatg tgttacctgg agtcgcagaa 960
ttacatccac cgggacctgg ccgccaggaa catcctcgtc ggggaaaaca ccctctgcaa 1020
agttggggac ttcgggttag ccaggcttat caaggaggac gtctacctct cccatgacca 1080
caatatcccc tacaagtgga cggcccctga agcgctctcc cgaggccatt actccaccaa 1140
atccgacgtc tggtcctttg ggattctcct gcatgagatg ttcagcaggg gtcaggtgcc 1200
ctacccaggc atgtccaacc atgaggcctt cctgagggtg gacgccggct accgcatgcc 1260
ctgccctctg gagtgcccgc ccagcgtgca caagctgatg ctgacatgct ggtgcaggga 1320
ccccgagcag agaccctgct tcaaggccct gcgggagagg ctctccagct tcaccagcta 1380
cgagaacccg acctgagctg ctgtggagcg ggcatggccg ggccctgctg aggaggggcc 1440
tgggcagagg gcctggacct gggatcaagg cccacgcgct tccctggggt ttactgaggt 1500
gatgggtgca ggaaaggttc acaaatgtgg agtgtctgcg tccaatacac gcgtgtgctc 1560
ctctccttac tccatcgtgt gtgccttggg tctcagctgc tgacacgcag cctgctctgg 1620
agcctgcaga tgagatccgg gagactgaca cgaagccagc agaggtcaga ggggactctg 1680
accacagccc gctctctggc tgtctgtctg cagtgcccgg ctgagggtgg gaggcaaaca 1740
cgccttgttc ctgctcttcc cagttcagct tggtgggaga aagtcattcg cgtggctcgg 1800
gacgctcatg taaatttggt tttggtgctc aagggttctt tcctcccagg ggcaggtgtt 1860
tctttcctgt ttgtcttgtg tcttgagagc ttggccttat gaccagtgag aactctctcc 1920
ctggtctctg ccagcccaag catcactgcc cgaggcgcca gctcagtttc accgtccacg 1980
tccacaaggg gcttttccca ccttcacctt tgtcgctggg tcagtgctgg aaagcgcccc 2040
tcactcctgc gctgacaagg gcccttctct actgtctgtg gggtggttcc gggctggggg 2100
ggctgcctcc tttgcacctg attttgaagg tgtctctttc atccatggtt aagtcataaa 2160
aagcttattg gttttggttt tgactcacct gaaagttttt ttggtttaaa agaagaatag 2220
gcggggcacg gtggctcatg cctgtaatcc cagcactttg ggaggctgag gcaggtggat 2280
cacgaggtca ggagatcgac accatcctgg ctaacacggt gaaaccccgt ctctactaaa 2340
aaatacaaaa aattagctgg gtgtggtggt gggggtgggc gcctgtagtc ccagctacgt 2400
gggaggctga ggcagcagac tggtgtgaac ccgggaggtg gagcttgcag tgagccgaga 2460
tcgcgccact gcactccagc ctgggcgaca gagcgagact ccatctcaaa 2510

<210> SEQ ID NO 26
<211> LENGTH: 2620
<212> TYPE: DNA
<213> ORGANISM: Homo sapiens

<400> SEQUENCE: 26
acaggcacag gtgaggaact caactcaaac tcctctctct gggaaaacgc ggtgcttgct 60

-continued cctcccggag tggccttggc agggtgttgg agccctcggt ctgccccgtc cggtctctgg 120
ggccaaggct gggtttccct catgtatggc aagagctcta ctcgtgcggt gcttcttctc 180
cttggcatac agctcacagc tctttggcct atagcagctg tggaaattta tacctcccgg 240
gtgctggagg ctgttaatgg gacagatgct cggttaaaat gcactttctc cagctttgcc 300
cctgtgggtg atgctctaac agtgacctgg aattttcgtc ctctagacgg gggacctgag 360
cagtttgtat tctactacca catagatccc ttccaaccca tgagtgggcg gtttaaggac 420
cgggtgtctt gggatgggaa tcctgagcgg tacgatgcct ccatccttct ctggaaactg 480
cagttcgacg acaatgggac atacacctgc caggtgaaga acccacctga tgttgatggg 540
gtgatagggg agatccggct cagcgtcgtg cacactgtac gcttctctga gatccacttc 600
ctggctctgg ccattggctc tgcctgtgca ctgatgatca taatagtaat tgtagtggtc 660
ctcttccagc attaccggaa aaagcgatgg gccgaaagag ctcataaagt ggtggagata 720
aaatcaaaag aagaggaaag gctcaaccaa gagaaaaagg tctctgttta tttagaagac 780
acagactaac aattttagat ggaagctgag atgatttcca agaacaagaa ccctagtatt 840
tcttgaagtt aatggaaact tttctttggc ttttccagtt gtgacccgtt ttccaaccag 900
ttctgcagca tattagattc tagacaagca acacccctct ggagccagca cagtgctcct 960
ccatatcacc agtcatacac agcctcatta ttaaggtctt atttaatttc agagtgtaaa 1020
ttttttcaag tgctcattag gttttataaa caagaagcta catttttgcc cttaagacac 1080
tacttacagt gttatgactt gtatacacat atattggtat caaaagggat aaaagccaat 1140
ttgtctgtta catttccttt cacgtatttc ttttagcagc acttctgcta ctaaagttaa 1200
tgtgtttact ctctttcctt cccacattct caattaaaag gtgagctaag cctcctcggt 1260
gtttctgatt aacagtaaat cctaaattca aactgttaaa tgacattttt atttttatgt 1320
ctctccttaa ctatgagaca catcttgttt tactgaattt ctttcaatat tccaggtgat 1380
agatttttgt tgttttgtta attaatccaa gatttacaat agcacaacgc taaatcacac 1440
agtaactaca aaaggttaca tagatatgaa aagattggca gaggccattg caggatgaat 1500
cacttgtcac ttttcttctg tgctgggaaa aataatcaac aatgtgggtc tttcatgagc 1560
agtgacggat agtttagctt actatgtttc ccccccaatt caatgatcta taacaacaga 1620
gcaaagtcta tgctcatttg cagactggaa tcattaagta atttaataaa aaaattgtga 1680
aacagcatat tacaagtttg aaaattcagg gctggtgaaa aaaatcaact ctaaatgatg 1740
ataattttgt acagttttat ataaaactct gagaactaga agaaattatt aacttttttt 1800 ctttttttaat tctaattcac ttgtttattt tgggggagga agactttggt atggagcaaa 1860
gaaataccaa aactacttta aatggaataa aaccaacttt attctttttt tcccccatac 1920
tggtagataa agcaaacttt ataagtgggc tattgaaaga aaagttacaa gcttaagata 1980
cagaagcatt tgttcaaagg atagaaagca tctaaaagtt taggctcaag atcaatcttt 2040
acagattgat attttcagtt tttaatcgac tggactgcag atgtttttttc ttttaacaaa 2100 ctggaatttt caaacagatt atctgtattt aaatgtatag accttgatat ttttccaata 2160 ctattttttta aaaaattgta tgatttacat atgaacctca gttctgaaat tcattacata 2220
tctgtctcat tctgcctttt atactgtcta aaaaagcaaa gttttaaagt gcaattttaa 2280
aactgtaaat tacatctgaa ggctatatat cctttaatca cattttatat tttttcttca 2340
caattctaac ctttgaaaat attataactg gatatttctt caaacagatg tcctggatga 2400

```
tggtccataa gaataatgaa gaagtagtta aaaatgtatg gacagttttt ccggcaaaat   2460

ttgtagctta tgtcttggct aaatagtcaa ggggtaatat gggcctgttg tttagtgtct   2520

ccttcctaaa gagcactttt gtattgtaat ttatttttta ttatgcttta aacactatgt   2580

aaataaacct ttagtaataa agaattatca gttataaaaa                        2620


<210> SEQ ID NO 27
<211> LENGTH: 3950
<212> TYPE: DNA
<213> ORGANISM: Homo sapiens

<400> SEQUENCE: 27

attaaggact cggggcagga ggggcagaag ttgcgcgcag gccggcgggc gggagcggac     60

accgaggccg gcgtgcaggc gtgcgggtgt gcgggagccg ggctcggggg gatcggaccg    120

agagcgagaa gcgcggcatg gagctccagg cagcccgcgc ctgcttcgcc ctgctgtggg    180

gctgtgcgct ggccgcggcc gcggcggcgc agggcaagga agtggtactg ctggactttg    240

ctgcagctgg aggggagctc ggctggctca cacacccgta tggcaaaggg tgggacctga    300

tgcagaacat catgaatgac atgccgatct acatgtactc cgtgtgcaac gtgatgtctg    360

gcgaccagga caactggctc cgcaccaact gggtgtaccg aggagaggct gagcgtatct    420

tcattgagct caagtttact gtacgtgact gcaacagctt ccctggtggc gccagctcct    480

gcaaggagac tttcaacctc tactatgccg agtcggacct ggactacggc accaacttcc    540

agaagcgcct gttcaccaag attgacacca ttgcgcccga tgagatcacc gtcagcagcg    600

acttcgaggc acgccacgtg aagctgaacg tggaggagcg ctccgtgggg ccgctcaccc    660

gcaaaggctt ctacctggcc ttccaggata tcggtgcctg tgtggcgctg ctctccgtcc    720

gtgtctacta caagaagtgc cccgagctgc tgcagggcct ggcccacttc cctgagacca    780

tcgccggctc tgatgcacct tccctggcca ctgtggccgg cacctgtgtg gaccatgccg    840

tggtgccacc gggggggtgaa gagccccgta tgcactgtgc agtggatggc gagtggctgg    900

tgcccattgg gcagtgcctg tgccaggcag gctacgagaa ggtggaggat gcctgccagg    960

cctgctcgcc tggatttttt aagtttgagg catctgagag cccctgcttg gagtgccctg   1020

agcacacgct gccatcccct gagggtgcca cctcctgcga gtgtgaggaa ggcttcttcc   1080

gggcacctca ggacccagcg tcgatgcctt gcacacgacc cccctccgcc ccacactacc   1140

tcacagccgt gggcatgggt gccaaggtgg agctgcgctg gacgcccccct caggacagcg   1200

ggggccgcga ggacattgtc tacagcgtca cctgcgaaca gtgctggccc gagtctgggg   1260

aatgcgggcc gtgtgaggcc agtgtgcgct actcggagcc tcctcacgga ctgacccgca   1320

ccagtgtgac agtgagcgac ctggagcccc acatgaacta caccttcacc gtggaggccc   1380

gcaatggcgt ctcaggcctg gtaaccagcc gcagcttccg tactgccagt gtcagcatca   1440

accagacaga gccccccaag gtgaggctgg agggccgcag caccacctcg cttagcgtct   1500

cctggagcat ccccccgccg cagcagagcc gagtgtggaa gtacgaggtc acttaccgca   1560

agaagggaga ctccaacagc tacaatgtgc gccgcaccga gggtttctcc gtgaccctgg   1620

acgacctggc cccagacacc acctacctgg tccaggtgca ggcactgacg caggagggcc   1680

agggggccgg cagcaaggtg cacgaattcc agacgctgtc ccccggaggga tctggcaact   1740

tggcggtgat tggcggcgtg gctgtcggtg tggtcctgct tctggtgctg gcaggagttg   1800

gcttctttat ccaccgcagg aggaagaacc agcgtgcccg ccagtccccg gaggacgttt   1860

acttctccaa gtcagaacaa ctgaagcccc tgaagacata cgtggacccc cacacatatg   1920
```

aggaccccaa ccaggctgtg ttgaagttca ctaccgagat ccatccatcc tgtgtcactc 1980
ggcagaaggt gatcggagca ggagagtttg gggaggtgta caagggcatg ctgaagacat 2040
cctcggggaa gaaggaggtg ccggtggcca tcaagacgct gaaagccggc tacacagaga 2100
agcagcgagt ggacttcctc ggcgaggccg gcatcatggg ccagttcagc caccacaaca 2160
tcatccgcct agagggcgtc atctccaaat acaagcccat gatgatcatc actgagtaca 2220
tggagaatgg ggccctggac aagttccttc gggagaagga tggcgagttc agcgtgctgc 2280
agctggtggg catgctgcgg ggcatcgcag ctggcatgaa gtacctggcc aacatgaact 2340
atgtgcaccg tgacctggct gcccgcaaca tcctcgtcaa cagcaacctg gtctgcaagg 2400
tgtctgactt tggcctgtcc cgcgtgctgg aggacgaccc cgaggccacc tacaccacca 2460
gtggcggcaa gatccccatc cgctggaccg ccccggaggc catttcctac cggaagttca 2520
cctctgccag cgacgtgtgg agctttggca ttgtcatgtg ggaggtgatg acctatggcg 2580
agcggcccta ctgggagttg tccaaccacg aggtgatgaa agccatcaat gatggcttcc 2640
ggctccccac acccatggac tgcccctccg ccatctacca gctcatgatg cagtgctggc 2700
agcaggagcg tgcccgccgc cccaagttcg ctgacatcgt cagcatcctg gacaagctca 2760
ttcgtgcccc tgactccctc aagaccctgg ctgactttga cccccgcgtg tctatccggc 2820
tccccagcac gagcggctcg gagggggtgc ccttccgcac ggtgtccgag tggctggagt 2880
ccatcaagat gcagcagtat acggagcact tcatggcggc cggctacact gccatcgaga 2940
aggtggtgca gatgaccaac gacgacatca agaggattgg ggtgcggctg cccggccacc 3000
agaagcgcat cgcctacagc ctgctgggac tcaaggacca ggtgaacact gtggggatcc 3060
ccatctgagc ctcgacaggg cctggagccc catcggccaa gaatacttga agaaacagag 3120
tggcctccct gctgtgccat gctgggccac tggggacttt atttatttct agttctttcc 3180
tccccctgca acttccgctg aggggtctcg gatgacaccc tggcctgaac tgaggagatg 3240
accagggatg ctgggctggg ccctctttcc ctgcgagacg cacacagctg agcacttagc 3300
aggcaccgcc acgtcccagc atccctggag caggagcccc gccacagcct tcggacagac 3360
atataggata ttcccaagcc gaccttccct ccgccttctc ccacatgagg ccatctcagg 3420
agatggaggg cttggcccag cgccaagtaa acagggtacc tcaagcccca tttcctcaca 3480
ctaagagggc agactgtgaa cttgactggg tgagacccaa agcggtccct gtccctctag 3540
tgccttcttt agaccctcgg gccccatcct catccctgac tggccaaacc cttgctttcc 3600
tgggcctttg caagatgctt ggttgtgttg aggtttttaa atatatattt tgtactttgt 3660
ggagagaatg tgtgtgtgtg gcagggggcc ccgccagggc tggggacaga gggtgtcaaa 3720
cattcgtgag ctggggactc agggaccggt gctgcaggag tgtcctgccc atgccccagt 3780
cggccccatc tctcatcctt ttggataagt ttctattctg tcagtgttaa agattttgtt 3840
ttgttggaca tttttttcga atcttaattt attatttttt ttatatttat tgttagaaaa 3900
tgacttattt ctgctctgga ataaagttgc agatgattca aaccgaaaaa 3950

<210> SEQ ID NO 28
<211> LENGTH: 5810
<212> TYPE: DNA
<213> ORGANISM: Homo sapiens

<400> SEQUENCE: 28
aacgggctca ttcagcggtc gcgagctgcc cgcgaggggg agcggccgga cggagagcgc 60

-continued

```
gacccgtccc gggggtgggg ccgggcgcag cggcgagagg aggcgaaggt ggctgcggta    120
gcagcagcgc ggcagcctcg gacccagccc ggagcgcagg gcggccgctg caggtccccg    180
ctcccctccc cgtgcgtccg cccatggccg ccgccgggca gctgtgcttg ctctacctgt    240
cggcggggct cctgtcccgg ctcggcgcag ccttcaactt ggacactcgg gaggacaacg    300
tgatccggaa atatggagac cccgggagcc tcttcggctt ctcgctggcc atgcactggc    360
aactgcagcc cgaggacaag cggctgttgc tcgtgggggc cccgcgggca gaagcgcttc    420
cactgcagag agccaacaga acgggagggc tgtacagctg cgacatcacc gcccgggggc    480
catgcacgcg gatcgagttt gataacgatg ctgaccccac gtcagaaagc aaggaagatc    540
agtggatggg ggtcaccgtc cagagccaag gtccaggggg caaggtcgtg acatgtgctc    600
accgatatga aaaaaggcag catgttaata cgaagcagga atcccgagac atctttgggc    660
ggtgttatgt cctgagtcag aatctcagga ttgaagacga tatggatggg ggagattgga    720
gcttttgtga tgggcgattg agaggccatg agaaatttgg ctcttgccag caaggtgtag    780
cagctacttt tactaaagac tttcattaca ttgtatttgg agccccgggt acttataact    840
ggaaagggat tgttcgtgta gagcaaaaga ataacacttt ttttgacatg aacatctttg    900
aagatgggcc ttatgaagtt ggtggagaga ctgagcatga tgaaagtctc gttcctgttc    960
ctgctaacag ttacttaggt ttttctttgg actcagggaa aggtattgtt tctaaagatg   1020
agatcacttt tgtatctggt gctcccagag ccaatcacag tggagccgtg gttttgctga   1080
agagagacat gaagtctgca catctcctcc ctgagcacat attcgatgga gaaggtctgg   1140
cctcttcatt tggctatgat gtggcggtgg tggacctcaa caaggatggg tggcaagata   1200
tagttattgg agccccacag tattttgata gagatggaga agttggaggt gcagtgtatg   1260
tctacatgaa ccagcaaggc agatggaata atgtgaagcc aattcgtctt aatggaacca   1320
aagattctat gtttggcatt gcagtaaaaa atattggaga tattaatcaa gatggctacc   1380
cagatattgc agttggagct ccgtatgatg acttgggaaa ggtttttatc tatcatggat   1440
ctgcaaatgg aataaatacc aaaccaacac aggttctcaa gggtatatca ccttattttg   1500
gatattcaat tgctggaaac atggaccttg atcgaaattc ctaccctgat gttgctgttg   1560
gttccctctc agattcagta actattttca gatcccggcc tgtgattaat attcagaaaa   1620
ccatcacagt aactcctaac agaattgacc tccgccagaa aacagcgtgt ggggcgccta   1680
gtgggatatg cctccaggtt aaatcctgtt ttgaatatac tgctaacccc gctggttata   1740
atccttcaat atcaattgtg ggcacacttg aagctgaaaa agaaagaaga aaatctgggc   1800
tatcctcaag agttcagttt cgaaaccaag gttctgagcc caaatatact caagaactaa   1860
ctctgaagag gcagaaacag aaagtgtgca tggaggaaac cctgtggcta caggataata   1920
tcagagataa actgcgtccc attcccataa ctgcctcagt ggagatccaa gagccaagct   1980
ctcgtaggcg agtgaattca cttccagaag ttcttccaat tctgaattca gatgaaccca   2040
agacagctca tattgatgtt cacttcttaa aagagggatg tggagacgac aatgtatgta   2100
acagcaacct taaactagaa tataaatttt gcacccgaga aggaaatcaa gacaaatttt   2160
cttatttacc aattcaaaaa ggtgtaccag aactagttct aaaagatcag aaggatattg   2220
ctttagaaat aacagtgaca aacagccctt ccaacccaag gaatcccaca aaagatggcg   2280
atgacgccca tgaggctaaa ctgattgcaa cgtttccaga cactttaacc tattctgcat   2340
atagagaact gagggctttc cctgagaaac agttgagttg tgttgccaac cagaatggct   2400
cgcaagctga ctgtgagctc ggaaatcctt ttaaaagaaa ttcaaatgtc actttttatt   2460
```

-continued

```
tggttttaag tacaactgaa gtcacctttg acaccccaga tctggatatt aatctgaagt   2520
tagaaacaac aagcaatcaa gataatttgg ctccaattac agctaaagca aaagtggtta   2580
ttgaactgct tttatcggtc tcgggagttg ctaaaccttc ccaggtgtat tttggaggta   2640
cagttgttgg cgagcaagct atgaaatctg aagatgaagt gggaagttta atagagtatg   2700
aattcagggt aataaactta ggtaaacctc ttacaaacct cggcacagca accttgaaca   2760
ttcagtggcc aaaagaaatt agcaatggga aatggttgct ttatttggtg aaagtagaat   2820
ccaaaggatt ggaaaaggta acttgtgagc cacaaaagga gataaactcc ctgaacctaa   2880
cggagtctca caactcaaga aagaaacggg aaattactga aaaacagata gatgataaca   2940
gaaaattttc tttatttgct gaaagaaaat accagactct taactgtagc gtgaacgtga   3000
actgtgtgaa catcagatgc ccgctgcggg ggctggacag caaggcgtct cttattttgc   3060
gctcgaggtt atggaacagc acatttctag aggaatattc caaactgaac tacttggaca   3120
ttctcatgcg agccttcatt gatgtgactg ctgctgccga aaatatcagg ctgccaaatg   3180
caggcactca ggttcgagtg actgtgtttc cctcaaagac tgtagctcag tattcgggag   3240
taccttggtg gatcatccta gtggctattc tcgctgggat cttgatgctt gctttattag   3300
tgtttatact atggaagtgt ggtttcttca agagaaataa gaaagatcat tatgatgcca   3360
catatcacaa ggctgagatc catgctcagc catctgataa agagaggctt acttctgatg   3420
catagtattg atctacttct gtaattgtgt ggattcttta aacgctctag gtacgatgac   3480
agtgttcccc gataccatgc tgtaaggatc cggaaagaag agcgagagat caaagatgaa   3540
aagtatattg ataaccttga aaaaaaacag tggatcacaa agtggaacga aaatgaaagc   3600
tactcatagc gggggcctaa aaaaaaaaag cttcacagta cccaaactgc tttttccaac   3660
tcagaaattc aatttggatt taaaagcctg ctcaatccct gaggactgat ttcagagtga   3720
ctacacacag tacgaaccta cagttttaac tgtggatatt gttacgtagc ctaaggctcc   3780
tgttttgcac agccaaattt aaaactgttg gaatggattt ttctttaact gccgtaattt   3840
aactttctgg gttgccttta tttttggcgt ggctgactta catcatgtgt tggggaaggg   3900
cctgcccagt tgcactcagg tgacatcctc cagatagtgt agctgaggag gcacctacac   3960
tcacctgcac taacagagtg gccgtcctaa cctcgggcct gctgcgcaga cgtccatcac   4020
gttagctgtc ccacatcaca agactatgcc attggggtag ttgtgtttca acggaaagtg   4080
ctgtcttaaa ctaaatgtgc aatagaaggt gatgttgcca tcctaccgtc ttttcctgtt   4140
tcctagctgt gtgaatacct gctcacgtca aatgcataca agtttcattc tccctttcac   4200
taaaacacac aggtgcaaca gacttgaatg ctagttatac ttatttgtat atggtattta   4260
tttttcttt tctttacaaa ccattttgtt attgactaac aggccaaaga gtctccagtt   4320
tacccttcag gttggtttaa tcaatcagaa ttagagcatg ggaggtcatc actttgacct   4380
aaattattta ctgcaaaaag aaaatcttta taaatgtacc agagagagtt gttttaataa   4440
cttatctata aactataacc tctccttcat gacagcctcc accccacaac ccaaaaggtt   4500
taagaaatag aattataact gtaaagatgt ttatttcagg cattggatat tttttacttt   4560
agaagcctgc ataatgtttc tggatttcat actgtaacat tcaggaattc ttggagaaaa   4620
tgggtttatt cactgaactc tagtgcggtt tactcactgc tgcaaatact gtatattcag   4680
gacttgaaag aaatggtgaa tgcctatggt ggatccaaac tgatccagta taagactact   4740
gaatctgcta ccaaaacagt taatcagtga gtcgatgttc tattttttgt tttgtttcct   4800
```

```
cccctatctg tattcccaaa aattactttg gggctaattt aacaagaact ttaaattgtg   4860
ttttaattgt aaaaatggca gggggtggaa ttattactct atacattcaa cagagactga   4920
atagatatga aagctgattt tttttaatta ccatgcttca caatgttaag ttatatgggg   4980
agcaacagca aacaggtgct aatttgtttt ggatatagta taagcagtgt ctgtgttttg   5040
aaagaataga acacagtttg tagtgccact gttgttttgg gggggctttt ttcttttcgg   5100
aaatcttaaa ccttaagata ctaaggacgt tgttttggtt gtactttgga attcttagtc   5160
acaaaatata ttttgtttac aaaaatttct gtaaaacagg ttataacagt gtttaaagtc   5220
tcagtttctt gcttggggaa cttgtgtccc taatgtgttt agattgctag attgctaagg   5280
agctgatact ttgacagtgt ttttagacct gtgttactaa aaaaaagatg aatgtcctga   5340
aaagggtgtt gggagggtgg ttcaacaaag aaacaaagat gttatggtgt ttagatttat   5400
ggttgttaaa aatgtcatct caagtcaagt cactggtctg tttgcatttg atacattttt   5460
gtactaacta gcattgtaaa attatttcat gattagaaat tacctgtgga tatttgtata   5520
aaagtgtgaa ataaattttt tataaaagtg ttcattgttt cgtaacacag cattgtatat   5580
gtgaagcaaa ctctaaaatt ataaatgaca acctgaatta tctatttcat caaaccaaag   5640
ttcagtgttt ttatttttgg tgtctcatgt aatctcagat cagccaaaga tactagtgcc   5700
aaagcaatgg gattcggggt ttttttctgt tttcgctcta tgtaggtgat cctcaagtct   5760
ttcattttcc ttctttatga ttaaaagaaa cctacaggta tttaacaacc              5810
```

<210> SEQ ID NO 29
<211> LENGTH: 3640
<212> TYPE: DNA
<213> ORGANISM: Homo sapiens

<400> SEQUENCE: 29

```
gccaccacgt gtgtccctgc gcccggtggc caccgactca gtccctcgcc gaccagtctg     60
ggcagcggag gagggtggtt ggcagtggct ggaagcttcg ctatgggaag ttgttccttt    120
gctctctcgc gcccagtcct cctccctggt tctcctcagc cgctgtcgga ggagagcacc    180
cggagacgcg ggctgcagtc gcggcggctt ctccccgcct gggcggccgc gccgctgggc    240
aggtgctgag cgcccctaga gcctcccttg ccgcctccct cctctgcccg gccgcagcag    300
tgcacatggg gtgttggagg tagatgggct cccggcccgg gaggcggcgg tggatgcggc    360
gctgggcaga agcagccgcc gattccagct gccccgcgcg ccccgggcgc ccctgcgagt    420
ccccggttca gccatgggga cctctccgag cagcagcacc gccctcgcct cctgcagccg    480
catcgcccgc cgagccacag ccacgatgat cgcgggctcc cttctcctgc ttggattcct    540
tagcaccacc acagctcagc cagaacagaa ggcctcgaat ctcattggca cataccgcca    600
tgttgaccgt gccaccggcc aggtgctaac ctgtgacaag tgtccagcag gaacctatgt    660
ctctgagcat tgtaccaaca caagcctgcg cgtctgcagc agttgccctg tggggacctt    720
taccaggcat gagaatggca tagagaaatg ccatgactgt agtcagccat gcccatggcc    780
aatgattgag aaattacctt gtgctgcctt gactgaccga gaatgcactt gcccacctgg    840
catgttccag tctaacgcta cctgtgcccc ccatacggtg tgtcctgtgg gttggggtgt    900
gcggaagaaa gggacagaga ctgaggatgt gcggtgtaag cagtgtgctc ggggtacctt    960
ctcagatgtg ccttctagtg tgatgaaatg caaagcatac acagactgtc tgagtcagaa   1020
cctggtggtg atcaagccgg ggaccaagga gacagacaac gtctgtggca cactcccgtc   1080
cttctccagc tccacctcac cttcccctgg cacagccatc tttccacgcc ctgagcacat   1140
```

-continued

```
ggaaacccat gaagtccctt cctccactta tgttcccaaa ggcatgaact caacagaatc   1200
caactcttct gcctctgtta gaccaaaggt actgagtagc atccaggaag ggacagtccc   1260
tgacaacaca agctcagcaa gggggaagga agacgtgaac aagaccctcc caaaccttca   1320
ggtagtcaac caccagcaag gcccccacca cagacacatc ctgaagctgc tgccgtccat   1380
ggaggccact gggggcgaga agtccagcac gcccatcaag ggccccaaga ggggacatcc   1440
tagacagaac ctacacaagc attttgacat caatgagcat ttgccctgga tgattgtgct   1500
tttcctgctg ctggtgcttg tggtgattgt ggtgtgcagt atccggaaaa gctcgaggac   1560
tctgaaaaag gggccccggc aggatcccag tgccattgtg gaaaaggcag ggctgaagaa   1620
atccatgact ccaacccaga accgggagaa atggatctac tactgcaatg gccatggtat   1680
cgatatcctg aagcttgtag cagcccaagt gggaagccag tggaaagata tctatcagtt   1740
tctttgcaat gccagtgaga gggaggttgc tgctttctcc aatgggtaca cagccgacca   1800
cgagcgggcc tacgcagctc tgcagcactg gaccatccgg ggccccgagg ccagcctcgc   1860
ccagctaatt agcgccctgc gccagcaccg gagaaacgat gttgtggaga agattcgtgg   1920
gctgatggaa gacaccaccc agctggaaac tgacaaacta gctctcccga tgagccccag   1980
cccgcttagc ccgagcccca tccccagccc caacgcgaaa cttgagaatt ccgctctcct   2040
gacggtggag ccttccccac aggacaagaa caagggcttc ttcgtggatg agtcggagcc   2100
ccttctccgc tgtgactcta catccagcgg ctcctccgcg ctgagcagga acggttcctt   2160
tattaccaaa gaaaagaagg acacagtgtt gcggcaggta cgcctggacc cctgtgactt   2220
gcagcctatc tttgatgaca tgctccactt tctaaatcct gaggagctgc gggtgattga   2280
agagattccc caggctgagg acaaactaga ccggctattc gaaattattg gagtcaagag   2340
ccaggaagcc agccagaccc tcctggactc tgtttatagc catcttcctg acctgctgta   2400
gaacataggg atactgcatt ctggaaatta ctcaatttag tggcagggtg gttttttaat   2460
tttcttctgt ttctgatttt tgttgtttgg ggtgtgtgtg tgtgtttgtg tgtgtgtgtg   2520
tgtgtgtgtg tgtgtgtgtg tttaacagag aatatggcca gtgcttgagt tctttctcct   2580
tctctctctc tcttttttttt ttaaataact cttctgggaa gttggtttat aagcctttgc   2640
caggtgtaac tgttgtgaaa tacccaccac taaagttttt taagttccat attttctcca   2700
ttttgccttc ttatgtattt tcaagattat tctgtgcact ttaaatttac ttaacttacc   2760
ataaatgcag tgtgactttt cccacacact ggattgtgag gctcttaact tcttaaaagt   2820
ataatggcat cttgtgaatc ctataagcag tctttatgtc tcttaacatt cacacctact   2880
ttttaaaaac aaatattatt actattttta ttattgtttg tcctttataa attttcttaa   2940
agattaagaa aatttaagac cccattgagt tactgtaatg caattcaact ttgagttatc   3000
ttttaaatat gtcttgtata gttcatattc atggctgaaa cttgaccaca ctattgctga   3060
ttgtatggtt ttcacctgga caccgtgtag aatgcttgat tacttgtact cttcttatgc   3120
taatatgctc tgggctggag aaatgaaatc ctcaagccat caggatttgc tatttaagtg   3180
gcttgacaac tgggccacca aagaacttga acttcacctt ttaggatttg agctgttctg   3240
gaacacattg ctgcactttg gaaagtcaaa atcaagtgcc agtggcgccc tttccataga   3300
gaatttgccc agctttgctt taaaagatgt cttgtttttt atatacacat aatcaatagg   3360
tccaatctgc tctcaaggcc ttggtcctgg tgggattcct tcaccaatta ctttaattaa   3420
aaatggctgc aactgtaaga acccttgtct gatatatttg caactatgct cccatttaca   3480
```

aatgtacctt ctaatgctca gttgccaggt tccaatgcaa aggtggcgtg gactcccttt 3540
gtgtgggtgg ggtttgtggg tagtggtgaa ggaccgatat cagaaaaatg ccttcaagtg 3600
tactaattta ttaataaaca ttaggtgttt gttaaaaaaa 3640

<210> SEQ ID NO 30
<211> LENGTH: 1130
<212> TYPE: DNA
<213> ORGANISM: Homo sapiens

<400> SEQUENCE: 30
agtgccccag gagctatgac aagcaaagga acatacttgc ctggagatag cctttgcgat 60
atttaaatgt ccgtggatac agaaatctct gcaggcaagt tgctccagag catattgcag 120
gacaagcctg taacgaatag ttaaattcac ggcatctgga ttcctaatcc ttttccgaaa 180
tggcaggtgt gagtgcctgt ataaaatatt ctatgtttac cttcaacttc ttgttctggc 240
tatgtggtat cttgatccta gcattagcaa tatgggtacg agtaagcaat gactctcaag 300
caatttttgg ttctgaagat gtaggctcta gctcctacgt tgctgtggac atattgattg 360
ctgtaggtgc catcatcatg attctgggct tcctgggatg ctgcggtgct ataaaagaaa 420
gtcgctgcat gcttctgttg tttttcatag gcttgcttct gatcctgctc ctgcaggtgg 480
cgacaggtat cctaggagct gttttcaaat ctaagtctga tcgcattgtg aatgaaactc 540
tctatgaaaa cacaaagctt ttgagcgcca caggggaaag tgaaaaacaa ttccaggaag 600
ccataattgt gtttcaagaa gagtttaaat gctgcggttt ggtcaatgga gctgctgatt 660
ggggaaataa ttttcaacac tatcctgaat tatgtgcctg tctagataag cagagaccat 720
gccaaagcta taatggaaaa caagtttaca aagagacctg tatttctttc ataaaagact 780
tcttggcaaa aaatttgatt atagttattg gaatatcatt tggactggca gttattgaga 840
tactgggttt ggtgttttct atggtcctgt attgccagat cgggaacaaa tgaatctgtg 900
gatgcatcaa cctatcgtca gtcaaacccc tttaaaatgt tgctttggct ttgtaaattt 960
aaatatgtaa gtgctatata agtcaggagc agctgtcttt ttaaaatgtc tcggctagct 1020
agaccacaga tatcttctag acatattgaa cacatttaag atttgaggga tataagggaa 1080
aatgatatga atgtgtattt ttactcaaaa taaaagtaac tgtttacgtt 1130

<210> SEQ ID NO 31
<211> LENGTH: 1145
<212> TYPE: DNA
<213> ORGANISM: Homo sapiens

<400> SEQUENCE: 31
attctctccc cagcttgctg agccctttgc tcccctggcg actgcctgga cagtcagcaa 60
ggaattgtct cccagtgcat tttgccctcc tggctgccaa ctctggctgc taaagcggct 120
gccacctgct gcagtctaca cagcttcggg aagaggaaag gaacctcaga ccttccagat 180
cgcttcctct cgcaacaaac tatttgtcgc aggaataaag atggctgctg aaccagtaga 240
agacaattgc atcaactttg tggcaatgaa atttattgac aatacgcttt actttatagc 300
tgaagatgat gaaaacctgg aatcagatta ctttggcaag cttgaatcta aattatcagt 360
cataagaaat ttgaatgacc aagttctctt cattgaccaa ggaaatcggc ctctatttga 420
agatatgact gattctgact gtagagataa tgcaccccgg accatattta ttataagtat 480
gtataaagat agccagccta gaggtatggc tgtaactatc tctgtgaagt gtgagaaaat 540
ttcaactctc tcctgtgaga acaaaattat ttcctttaag gaaatgaatc ctcctgataa 600

-continued

```
catcaaggat acaaaaagtg acatcatatt ctttcagaga agtgtcccag gacatgataa    660

taagatgcaa tttgaatctt catcatacga aggatacttt ctagcttgtg aaaaagagag    720

agaccttttt aaactcattt tgaaaaaaga ggatgaattg gggatagat ctataatgtt     780

cactgttcaa aacgaagact agctattaaa atttcatgcc gggcgcagtg gctcacgcct    840

gtaatcccag ccctttggga ggctgaggcg ggcagatcac cagaggtcag gtgttcaaga    900

ccagcctgac caacatggtg aaacctcatc tctactaaaa atacaaaaaa ttagctgagt    960

gtagtgacgc atgccctcaa tcccagctac tcaagaggct gaggcaggag aatcacttgc   1020

actccggagg tagaggttgt ggtgagccga gattgcacca ttgcgctcta gcctgggcaa   1080

caacagcaaa actccatctc aaaaaataaa ataaataaat aaacaaataa aaaattcata   1140

atgtg                                                               1145
```

<210> SEQ ID NO 32
<211> LENGTH: 1790
<212> TYPE: DNA
<213> ORGANISM: Homo sapiens

<400> SEQUENCE: 32

```
gagggagggg ccgccgggga agaggaggag gaaggaaaga aagaaagcga gggagggaaa     60

gaggaggaag gaagatgcga gaaggcagag gaggagggag ggagggaagg agcgcggagc    120

ccggcccgga agctaggagc cattccgtag tgccatcccg agcaacgcac tgctgcagct    180

tccctgagcc tttccagcaa gtttgttcaa gattggctgt caagaatcat ggactgttat    240

tatatgcctt gttttctgtc aagacaccat gattcctggt aaccgaatgc tgatggtcgt    300

tttattatgc caagtcctgc taggaggcgc gagccatgct agtttgatac ctgagacggg    360

gaagaaaaaa gtcgccgaga ttcagggcca cgcgggagga cgccgctcag ggcagagcca    420

tgagctcctg cgggacttcg aggcgacact tctgcagatg tttgggctgc gccgccgccc    480

gcagcctagc aagagtgccg tcattccgga ctacatgcgg gatctttacc ggcttcagtc    540

tggggaggag gaggaagagc agatccacag cactggtctt gagtatcctg agcgcccggc    600

cagccgggcc aacaccgtga ggagcttcca ccacgaagaa catctggaga acatcccagg    660

gaccagtgaa aactctgctt ttcgtttcct ctttaacctc agcagcatcc ctgagaacga    720

ggcgatctcc tctgcagagc ttcggctctt ccgggagcag gtggaccagg gccctgattg    780

ggaaaggggc ttccaccgta taaacattta tgaggttatg aagcccccag cagaagtggt    840

gcctgggcac ctcatcacac gactactgga cacgagactg gtccaccaca atgtgacacg    900

gtgggaaact tttgatgtga gccctgcggt ccttcgctgg acccgggaga agcagccaaa    960

ctatgggcta gccattgagg tgactcacct ccatcagact cggacccacc agggccagca   1020

tgtcaggatt agccgatcgt tacctcaagg gagtgggaat tgggcccagc tccggcccct   1080

cctggtcacc tttggccatg atggccgggg ccatgccttg acccgacgcc ggagggccaa   1140

gcgtagccct aagcatcact cacagcgggc caggaagaag aataagaact gccggcgcca   1200

ctcgctctat gtggacttca gcgatgtggg ctggaatgac tggattgtgg ccccaccagg   1260

ctaccaggcc ttctactgcc atggggactg cccctttcca ctggctgacc acctcaactc   1320

aaccaaccat gccattgtgc agaccctggt caattctgtc aattccagta tccccaaagc   1380

ctgttgtgtg cccactgaac tgagtgccat ctccatgctg tacctggatg agtatgataa   1440

ggtggtactg aaaaattatc aggagatggt agtagaggga tgtgggtgcc gctgagatca   1500
```

ggcagtcctt gaggatagac agatatacac accacacaca cacaccacat acaccacaca 1560
cacacgttcc catccactca cccacacact acacagactg cttccttata gctggacttt 1620
tatttaaaaa aaaaaaaaaa aaaatggaaa aaatccctaa acattcacct tgaccttatt 1680
tatgacttta cgtgcaaatg ttttgaccat attgatcata tattttgaca aaatatattt 1740
ataactacgt attaaaagaa aaaaataaaa tgagtcatta ttttaaaggt 1790

<210> SEQ ID NO 33
<211> LENGTH: 1880
<212> TYPE: DNA
<213> ORGANISM: Homo sapiens

<400> SEQUENCE: 33
ccagatcata ccctgctggg caaaggagga agagccagag gatccagacg ccttggagga 60
cttggaacac ctgtaacagg acaaggagtt ctgctcaggc acgtggccac agaaaactac 120
ttaggaagcc tgtggtgaga acaacaacag tgcctgagaa tcccacggct ctggggaagt 180
gagccccgag gatgaggctg ctcgcctggc tgattttcct ggctaactgg ggaggtgcca 240
gggctgaacc agggaagttc tggcacatcg ctgacctgca ccttgaccct gactacaagg 300
tatccaaaga ccccttccag gtgtgcccat cagctggatc ccagccagtg cccgacgcag 360
gcccctgggg tgactacctc tgtgattctc cctgggccct catcaactcc tccatctatg 420
ccatgaagga gattgagcca gagccagact tcattctctg gactggtgat gacacgcctc 480
atgtgcccga tgagaaactg ggagaggcag ctgtactgga aattgtggaa cgcctgacca 540
agctcatcag agaggtcttt ccagatacta aagtctatgc tgctttggga aatcatgatt 600
ttcaccccaa aaaccagttc ccagctggaa gtaacaacat ctacaatcag atagcagaac 660
tatggaaacc ctggcttagt aatgagtcca tcgctctctt caaaaaaggt gccttctact 720
gtgagaagct gccgggtccc agcggggctg ggcgaattgt ggtcctcaac accaatctgt 780
actataccag caatgcgctg acagcagaca tggcggaccc tggccagcag ttccagtggc 840
tggaagatgt gctgaccgat gcatccaaag ctggggacat ggtgtacatt gtcggccacg 900
tgcccccggg gttctttgag aagacgcaaa acaaggcatg gttccgggag ggcttcaatg 960
aaaaatacct gaaggtggtc cggaagcatc atcgcgtcat agcagggcag ttcttcgggc 1020
accaccacac cgacagcttt cggatgctct atgatgatgc aggtgtcccc ataagcgcca 1080
tgttcatcac acctggagtc accccatgga aaaccacatt acctggagtg gtcaatgggg 1140
ccaacaatcc agccatccgg gtgttcgaat atgaccgagc cacactgagc ctgaaggaca 1200
tggtgaccta cttcatgaac ctgagccagg cgaatgctca ggggacgccg cgctgggagc 1260
tcgagtacca gctgaccgag gcctatgggg tgccggacgc cagcgcccac tccatgcaca 1320
cagtgctgga ccgcatcgct ggcgaccaga gcacactgca gcgctactac gtctataact 1380
cagtcagcta ctctgctggg gtctgcgacg aggcctgcag catgcagcac gtgtgtgcca 1440
tgcgccaggt ggacattgac gcttacacca cctgtctgta tgcctctggc accacgcccg 1500
tgccccagct cccgctgctg ctgatggccc tgctgggcct gtgcacgctc gtgctgtgac 1560
ctgccaggct caccttcttc ctggtaacgg gtaacggggg cagcgcccag gatcacccag 1620
agctgggcct tccaccattt cctccgcgcc tgaggagtga actgaaatag gacaaccgaa 1680
tcaggaagcg aagccccagg agctgcagcc atccgtgatc gcgccactgc actccagcct 1740
gggcgacaaa gccagactct ctccaaaaac aaaccagaaa cagaaaagaa atgacgaccc 1800
aagacccccc tacaagcata cttcttttgc gtattatgtt ttactcacaa aacaaagctc 1860
atcatgcgtt tgaaaaaaaa 1880

<210> SEQ ID NO 34
<211> LENGTH: 3200
<212> TYPE: DNA
<213> ORGANISM: Homo sapiens

<400> SEQUENCE: 34
cgcgagctaa gcaggaggcg gaggcggagg cggagggcga ggggcgggga gcgccgcctg 60
gagcgcggca ggtcatattg aacattccag atacctatca ttactcgatg ctgttgataa 120
cagcaagatg gctttgaact cagggtcacc accagctatt ggaccttact atgaaaacca 180
tggataccaa ccggaaaacc cctatcccgc acagcccact gtggtcccca ctgtctacga 240
ggtgcatccg gctcagtact acccgtcccc cgtgccccag tacgccccga gggtcctgac 300
gcaggcttcc aaccccgtcg tctgcacgca gcccaaatcc ccatccggga cagtgtgcac 360
ctcaaagact aagaaagcac tgtgcatcac cttgaccctg ggaccttcc tcgtgggagc 420 tgcgctggcc gctggcctac tctggaagtt catgggcagc aagtgctcca actctgggat 480
agagtgcgac tcctcaggta cctgcatcaa cccctctaac tggtgtgatg gcgtgtcaca 540
ctgccccggc ggggaggacg agaatcggtg tgttcgcctc tacggaccaa acttcatcct 600
tcagatgtac tcatctcaga ggaagtcctg gcaccctgtg tgccaagacg actggaacga 660
gaactacggg cgggcggcct gcagggacat gggctataag aataattttt actctagcca 720
aggaatagtg gatgacagcg gatccaccag ctttatgaaa ctgaacacaa gtgccggcaa 780
tgtcgatatc tataaaaaac tgtaccacag tgatgcctgt tcttcaaaag cagtggtttc 840
tttacgctgt atagcctgcg ggtcaactt gaactcaagc cgccagagca ggatcgtggg 900
cggtgagagc gcgctcccgg gggcctggcc ctggcaggtc agcctgcacg tccagaacgt 960
ccacgtgtgc ggaggctcca tcatcacccc cgagtggatc gtgacagccg cccactgcgt 1020
ggaaaaacct cttaacaatc catggcattg gacggcattt gcggggattt tgagacaatc 1080
tttcatgttc tatggagccg gataccaagt agaaaaagtg atttctcatc caaattatga 1140
ctccaagacc aagaacaatg acattgcgct gatgaagctg cagaagcctc tgactttcaa 1200
cgacctagtg aaaccagtgt gtctgcccaa cccaggcatg atgctgcagc cagaacagct 1260
ctgctggatt tccgggtggg gggccaccga ggagaaaggg aagacctcag aagtgctgaa 1320
cgctgccaag gtgcttctca ttgagacaca gagatgcaac agcagatatg tctatgacaa 1380
cctgatcaca ccagccatga tctgtgccgg cttcctgcag gggaacgtcg attcttgcca 1440
gggtgacagt ggagggcctc tggtcacttc gaagaacaat atctggtggc tgatagggga 1500
tacaagctgg ggttctggct gtgccaaagc ttacagacca ggagtgtacg ggaatgtgat 1560
ggtattcacg gactggattt atcgacaaat gagggcagac ggctaatcca catggtcttc 1620
gtccttgacg tcgttttaca agaaaacaat ggggctggtt ttgcttcccc gtgcatgatt 1680
tactcttaga gatgattcag aggtcacttc atttttatta aacagtgaac ttgtctggct 1740
ttggcactct ctgccattct gtgcaggctg cagtggctcc cctgcccagc ctgctctccc 1800
taaccccttg tccgcaaggg gtgatggccg gctggttgtg ggcactggcg gtcaagtgtg 1860
gaggagaggg gtggaggctg ccccattgag atcttcctgc tgagtccttt ccaggggcca 1920
attttggatg agcatggagc tgtcacctct cagctgctgg atgacttgag atgaaaaagg 1980
agagacatgg aaagggagac agccaggtgg cacctgcagc ggctgccctc tggggccact 2040

-continued

```
tggtagtgtc cccagcctac ctctccacaa ggggattttg ctgatgggtt cttagagcct   2100

tagcagccct ggatggtggc cagaaataaa gggaccagcc cttcatgggt ggtgacgtgg   2160

tagtcacttg taaggggaac agaaacattt ttgttcttat ggggtgagaa tatagacagt   2220

gcccttggtg cgagggaagc aattgaaaag gaacttgccc tgagcactcc tggtgcaggt   2280

ctccacctgc acattgggtg gggctcctgg gagggagact cagccttcct cctcatcctc   2340

cctgaccctg ctcctagcac cctggagagt gcacatgccc cttggtcctg gcagggcgcc   2400

aagtctggca ccatgttggc ctcttcaggc ctgctagtca ctggaaattg aggtccatgg   2460

gggaaatcaa ggatgctcag tttaaggtac actgtttcca tgttatgttt ctacacattg   2520

ctacctcagt gctcctggaa acttagcttt tgatgtctcc aagtagtcca ccttcattta   2580

actctttgaa actgtatcac ctttgccaag taagagtggt ggcctatttc agctgctttg   2640

acaaaatgac tggctcctga cttaacgttc tataaatgaa tgtgctgaag caaagtgccc   2700

atggtggcgg cgaagaagag aaagatgtgt tttgttttgg actctctgtg gtcccttcca   2760

atgctgtggg tttccaacca ggggaagggt cccttttgca ttgccaagtg ccataaccat   2820

gagcactact ctaccatggt tctgcctcct ggccaagcag gctggtttgc aagaatgaaa   2880

tgaatgattc tacagctagg acttaacctt gaaatggaaa gtcttgcaat cccatttgca   2940

ggatccgtct gtgcacatgc ctctgtagag agcagcattc ccagggacct tggaaacagt   3000

tggcactgta aggtgcttgc tccccaagac acatcctaaa aggtgttgta atggtgaaaa   3060

cgtcttcctt ctttattgcc ccttcttatt tatgtgaaca actgtttgtc tttttttgta   3120

tctttttaa actgtaaagt tcaattgtga aaatgaatat catgcaaata aattatgcga   3180

ttttttttc aaagcaaaaa                                                3200
```

```
<210> SEQ ID NO 35
<211> LENGTH: 5430
<212> TYPE: DNA
<213> ORGANISM: Homo sapiens

<400> SEQUENCE: 35

gtagggagcc agcccctggg cgcggcctgc agggtaccgg caaccgcccg ggtaagcggg     60

ggcaggacaa ggccggagcc tgtgtccgcc cggcagccgc ccgcagctgc agagagtccc    120

gctgcgtctc cgccgcgtgc gccctcctcg accagcagac ccgcgctgcg ctccgccgct    180

gacatgtgtg ccgctcagat gccgcccctg gcgcacatct tccgagggac gttcgtccac    240

tccacctgga cctgccccat ggaggtgctg cgggatcacc tcctcggcgt gagcgacagc    300

ggcaaaatag tgtttttaga agaagcatct caacaggaaa aactggccaa agaatggtgc    360

ttcaagccgt gtgaaataag agaactgagc caccatgagt tcttcatgcc tgggctggtt    420

gatacacaca tccatgcctc tcagtattcc tttgctggaa gtagcataga cctgccactc    480

ttggagtggc tgaccaagta cacatttcct gcagaacaca gattccagaa catcgacttt    540

gcagaagaag tatataccag agttgtcagg agaacactaa agaatggaac aaccacagct    600

tgttactttg caacaattca cactgactca tctctgctcc ttgccgacat tacagataaa    660

tttggacagc gggcatttgt gggcaaagtt tgcatggatt tgaatgacac ttttccagaa    720

tacaaggaga ccactgagga atcgatcaag gaaactgaga gatttgtgtc agaaatgctc    780

caaaagaact attctagagt gaagcccata gtgacaccac gtttttccct ctcctgctct    840

gagactttga tgggtgaact gggcaacatt gctaaaaccc gtgatttgca cattcagagc    900

catataagtg aaaatcgtga tgaagttgaa gctgtgaaaa acttataccc cagttataaa    960
```

-continued

```
aactacacat ctgtgtatga taaaaacaat cttttgacaa ataagacagt gatggcacac   1020
ggctgctacc tctctgcaga agaactgaac gtattccatg aacgaggagc atccatcgca   1080
cactgtccca attctaattt atcgctcagc agtggatttc taaatgtgct agaagtcctg   1140
aaacatgaag tcaagatagg gctgggtaca gacgtggctg gtggctattc atattccatg   1200
cttgatgcaa tcagaagagc agtgatggtt tccaatatcc ttttaattaa taaggtaaat   1260
gagaaaagcc tcaccctcaa agaagtcttc agactagcta ctcttggagg aagccaagcc   1320
ctggggctgg atggtgagat tggaaacttt gaagtgggca aggaatttga tgccatcctg   1380
atcaacccca aagcatccga ctctcccatt gacctgtttt atggggactt ttttggtgat   1440
atttctgagg ctgttatcca gaagttcctc tatctaggag atgatcgaaa tattgaagag   1500
gtttatgtgg gcggaaagca ggtggttccg ttttccagct cagtgtaaga ccctcgggcg   1560
tctacaaagt tctcctggga ttagcgtggt tctgcatctc ccttgtgccc aggtggagtt   1620
agaaagtcaa aaaatagtac cttgttcttg ggatgactat ccctttctgt gtctagttac   1680
agtattcact tgacaaatag ttcgaaggaa gttgcactaa ttctcaactc tggttgagag   1740
ggttcataaa tttcatgaaa atatctccct ttggagctgc tcagacttac tttaagctca   1800
aacagaaggg aatgctatta ctggtggtgt tcctacggta agacttaagc aaagcctttt   1860
tcatatttga aaatgtggaa agaaaagatg ttcctaaaag gttagatatt ttgagctaat   1920
aattgcaaaa attagaagac tgaaaatgga cccatgagag tatattttta tgagggagca   1980
aaagttagac tgagaacaaa cgttagaaaa tcacttcaga ttgtgtttga aaattatata   2040
ctgagcatac taatttaaaa agagaacttg ttgaaattta aaacgtgttt ctaggttgac   2100
cttgtgtttt agaaatttgc acttaatgga atttgcattt cagagatgtg ttagtgttgt   2160
gctttgcctt ctttggcgat gaatgtcaga aattgaatgc cacatgcttt cataatatag   2220
ttttgtgctt caaagtgttt gacagaagtt gggtattaaa gatttaaagt ctcttaggaa   2280
tattattcat gtaactccat ggcataaata gttgtatttt tgtgtacttt aaaatcaact   2340
tataactgtg agatgttatt gcttccattt tattagaaga gaaacaaatt ccatgcttta   2400
tggaatttat gtagactgga gtcttcgtga actggggcaa atgctggcat ccaggagccg   2460
ccaatactaa caggacaggt tccattgcca tggcctattc cacccaaaca atatgttgta   2520
gtttctggaa attccatact cagatatcag tctgctagaa ctttaaaatg aaggacaaat   2580
cctgttaaag aaatattgtt aaaaatcttt aaaccctgtg tattgaaagc actctatttt   2640
ctaattttat ccagttttct gtttaactcc ttataatgtt taggatatta aaattttagg   2700
ataatgaaga gtacataatg tcctacttaa tatttatgtt aataggactt aattcttact   2760
agacatctag gaacattaca aagcaaagac tatttttatg cttccataac ctagaattaa   2820
aaccaaatta tgaccttatg ataaatcttt aagtattggt gtgaatgtta tttaaattct   2880
atatttttct tatttaatta caaatactat aaatgagcaa ggaaaaggaa tagactttct   2940
taatatatta taacactcat tcctagagct taggggtgac tctttaatat taccttatag   3000
tagaaacttt atgtaatata gctaactccg tatttacaga acaaaaaaac acagttcccc   3060
ctcctgtagt ataaatttta ttttcacata cttagctaat ttagcagtaa ttggcccagt   3120
tttttcccta atagaaatac ttttagattt gattatgtat acatgacacc taaagaggga   3180
acaaaagtta gttttatttt tttaataaac aacagagttt gttttgtgag ataagtatct   3240
tagtaaaccc aatttccagt cttagtctgt atttccaata tttctaattc ctgagccacg   3300
```

-continued tcaaagatgc cttgccaaat ttctccccat ttctctacgg ggctagcaaa aatcttcagc 3360
tttatcactc aacccctgcc aaaggaactt gattacatgg tgtctaacca aatgagcagg 3420
cttaggaatt tagatgagat gtgtaagatt cacttacagg cagtagctgc ttctagcatt 3480
tgcaagatcc tacactttta ccttctttaa gggtgtacat tttgatgttg aacatcagtt 3540
ttcatgtaga cttaggactc atgtgcagta aatataaata agtgtagcat cagaagcagt 3600
aggaatggcc gtatacaacc atcctgttaa acatttaaat ttagctctga tagtgtgtta 3660
agacctgaat atctttccta gtaaaaatag gatgtgttga aatatttata tgtactttga 3720
tctctccaca tcacttataa cttatgtgtt ttatttctcc aagtgcggtg ttcctgaatg 3780
ttatgtatgc tttttttct gtaccacagg cattatctat acctggggcc agattttctg 3840
cactttgaaa tgttgccttt gcctaatgta ggttgacttt ctgaattgtg gagaggcact 3900
tttccaagcc aatcttattt gtcacttttt gttttaatat cttgctctct gacaggaaag 3960
aaacaattca cttaccagcc tcctcacccc atcctccacc atttccttaa tgttccatgg 4020
tattttcaac ggaatacact ttgaaaggta aaaacaattc aaaagtatcg attatcataa 4080
attcacaaaa tatttttgca accagaacac aaaagcaggc tagtcagcta aggtaaattt 4140
cattttcaaa cgagagggaa acatgggaag taaaagatta ggatgtgaaa ggttgtccta 4200
aacagaccaa ggagactgtt ccctaattta ttctcttggc tggttctctc attgaattat 4260
cagaccccaa gaggagatat tggaacaggc tcccttcatg ccaagggtct ttctaagtta 4320
atactgtgag cattgagccc ccattaaaac tctttttac ttcagaaaga attttacagg 4380
ttaaagggaa agaaatggtg ggaaactctc cccgtaatgc ttagccaact ttaaagtgta 4440
cccttcaata tccccattgg caactgcagc tgagatctta gagaggaaat ataaccggtg 4500
tgagatctag caatgcattt tgaatcttca ctccctacca ggctcttcct atttttaatc 4560
tcttcacctc agaactagac atatggagag ctttaaaggc aagctggaag gcacattgta 4620
tcaattctac cttgtgctat acgtaggaga gatccaaaat ttggatgctt ctggagactc 4680
ttagacatct tttcattgtt gtccattttt aaagttgatg attgctggaa acattcacac 4740
gcttaaaagc aatggtgtga gttattaatg ggtaaactaa gaagtgttat aggcaatgac 4800
ttgaaatggt ttttaaattg tatggattgt taagaattgt tgaaaaaaaa ttttttttt 4860 ttggacagct tcaaggagat gttagcaatt tcagatatac tagccagttt aggtatgact 4920
ttggaagtgc agaaacagaa ggatactgtt agaaaatcct aacattggtc tccgtgcatg 4980
tgttcacacc tggtctcact gcctttcctt cccacagacc tgagtgtgaa agactgagag 5040
ttgaggagtt actttgtgga tcttgtccaa atttagtgaa atgtggaagt caaccagacc 5100
aatgatggaa ttaaatgtaa attccaagag ggctttcaca gtccacaggg ttcaaatgac 5160
ttgggtaaca gaagttattc ttagcttacc tgttatgtga cagtgattta cctgtccatt 5220
tccaacccaa aagcctgtca gaaagcattc tttagagaaa accactttac atttgttgtt 5280
aaactcctga tcgctactct taagaatata catgtatgta ttcataggaa catttttct 5340 caatatttgt atgattcgct tactgttatt gtgctgagtg agctcctgtg tgcttcagac 5400
aaaaataaat gagactttgt gtttacgtta 5430

<210> SEQ ID NO 36
<211> LENGTH: 4541
<212> TYPE: DNA
<213> ORGANISM: Homo sapiens

<400> SEQUENCE: 36

-continued

```
ggatcctcta gggtcccagc tcgcctcgat ggagctcctc ccgccgctgc ctcagtcctt     60
cctgttgctg ctgctgttgc ctgccaagcc cgcggcgggc gaggactggc agtgcccgcg    120
cacccccctac gcggcctctc gcgactttga cgtgaagtac gtggtgccca gcttctccgc    180
cggaggcctg gtacaggcca tggtgaccta cgagggcgac agaaatgaga gtgctgtgtt    240
tgtagccata cgcaatcgcc tgcatgtgct tgggcctgac ctgaagtctg tccagagcct    300
ggccacgggc cctgctggag accctggctg ccagacgtgt gcagcctgtg gcccaggacc    360
ccacggccct cccggtgaca cagacacaaa ggtgctggtg ctggatcccg cgctgcctgc    420
gctggtcagt tgtggctcca gcctgcaggg ccgctgcttc ctgcatgacc tagagcccca    480
agggacagcc gtgcatctgg cagcgccagc ctgcctcttc tcagcccacc ataaccggcc    540
cgatgactgc cccgactgtg tggccagccc attgggcacc cgtgtaactg tggttgagca    600
aggccaggcc tcctatttct acgtggcatc ctcactggac gcagccgtgg ctggcagctt    660
cagcccacgc tcagtgtcta tcaggcgtct caaggctgac gcctcgggat tcgcaccggg    720
ctttgtggcg ttgtcagtgc tgcccaagca tcttgtctcc tacagtattg aatacgtgca    780
cagcttccac acgggagcct tcgtatactt cctgactgta cagccggcca gcgtgacaga    840
tgatcctagt gccctgcaca cacgcctggc acggcttagc gccactgagc cagagttggg    900
tgactatcgg gagctggtcc tcgactgcag atttgctcca aaacgcaggc gccgggggc    960
cccagaaggc ggacagccct accctgtgct gcaggtggcc cactccgctc cagtgggtgc   1020
ccaacttgcc actgagctga gcatcgccga gggccaggaa gtactatttg ggtctttgt    1080
gactggcaag gatggtggtc ctggcgtggg ccccaactct gtcgtctgtg ccttccccat   1140
tgacctgctg gacacactaa ttgatgaggg tgtggagcgc tgttgtgaat ccccagtcca   1200
tccaggcctc cggcgaggcc tcgacttctt ccagtcgccc agtttttgcc ccaacccgcc   1260
tggcctggaa gccctcagcc ccaacaccag ctgccgccac ttccctctgc tggtcagtag   1320
cagcttctca cgtgtggacc tattcaatgg gctgttggga ccagtacagg tcactgcatt   1380
gtatgtgaca cgccttgaca acgtcacagt ggcacacatg ggcacaatgg atgggcgtat   1440
cctgcaggtg gagctggtca ggtcactaaa ctacttgctg tatgtgtcca acttctcact   1500
gggtgacagt gggcagcccg tgcagcggga tgtcagtcgt cttggggacc acctactctt   1560
tgcctctggg gaccaggttt tccaggtacc tatccgaggc cctggctgcc gccacttcct   1620
gacctgtggg cgttgcctaa gggcatggca tttcatgggc tgtggctggt gtgggaacat   1680
gtgcggccag cagaaggagt gtcctggctc ctggcaacag gaccactgcc cacctaagct   1740
tactgagttc cacccccaca gtggacctct aaggggcagt acaaggctga ccctgtgtgg   1800
ctccaacttc taccttcacc cttctggtct ggtgcctgag ggaacccatc aggtcactgt   1860
gggccaaagt ccctgccggc cactgcccaa ggacagctca aaactcagac cagtgccccg   1920
gaaagacttt gtagaggagt ttgagtgtga actggagccc ttgggcaccc aggcagtggg   1980
gcctaccaac gtcagcctca ccgtgactaa catgccaccg ggcaagcact tccgggtaga   2040
cggcacctcc gtgctgagag gcttctcttt catggagcca gtgctgatag cagtgcaacc   2100
cctctttggc ccacgggcag gaggcacctg tctcactctt gaaggccaga gtctgtctgt   2160
aggcaccagc cgggctgtgc tggtcaatgg gactgagtgt ctgctagcac gggtcagtga   2220
ggggcagctt ttatgtgcca cacccccctgg ggccacggtg gccagtgtcc cccttagcct   2280
gcaggtgggg ggtgcccagg tacctggttc ctggaccttc cagtacagag aagaccctgt   2340
```

-continued

```
cgtgctaagc atcagcccca actgtggcta catcaactcc cacatcacca tctgtggcca   2400
gcatctaact tcagcatggc acttagtgct gtcattccat gacgggctta gggcagtgga   2460
aagcaggtgt gagaggcagc ttccagagca gcagctgtgc cgccttcctg aatatgtggt   2520
ccgagacccc cagggatggg tggcagggaa tctgagtgcc cgaggggatg gagctgctgg   2580
ctttacactg cctggctttc gcttcctacc cccaccccat ccacccagtg ccaacctagt   2640
tccactgaag cctgaggagc atgccattaa gtttgagtat attgggctgg gcgctgtggc   2700
tgactgtgtg ggtatcaacg tgaccgtggg tggtgagagc tgccagcacg agttccgggg   2760
ggacatggtt gtctgccccc tgcccccatc cctgcagctt ggccaggatg gtgccccatt   2820
gcaggtctgc gtagatggtg aatgtcatat cctgggtaga gtggtgcggc cagggccaga   2880
tggggtccca cagagcacgc tccttggtat cctgctgcct ttgctgctgc ttgtggctgc   2940
actggcgact gcactggtct tcagctactg gtggcggagg aagcagctag ttcttcctcc   3000
caacctgaat gacctggcat ccctggacca gactgctgga gccacacccc tgcctattct   3060
gtactcgggc tctgactaca gaagtggcct tgcactccct gccattgatg gtctggattc   3120
caccacttgt gtccatggag catccttctc cgatagtgaa gatgaatcct gtgtgccact   3180
gctgcggaaa gagtccatcc agctaaggga cctggactct gcgctcttgg ctgaggtcaa   3240
ggatgtgctg attccccatg agcgggtggt cacccacagt gaccgagtca ttggcaaagg   3300
ccactttgga gttgtctacc acggagaata catagaccag gcccagaatc gaatccaatg   3360
tgccatcaag tcactaagtc gcatcacaga gatgcagcag gtggaggcct tcctgcgaga   3420
ggggctgctc atgcgtggcc tgaaccaccc gaatgtgctg gctctcattg gtatcatgtt   3480
gccacctgag ggcctgcccc atgtgctgct gccctatatg tgccacggtg acctgctcca   3540
gttcatccgc tcacctcagc ggaaccccac cgtgaaggac ctcatcagct ttggcctgca   3600
ggtagcccgc ggcatggagt acctggcaga gcagaagttt gtgcacaggg acctggctgc   3660
gcggaactgc atgctggacg agtcattcac agtcaaggtg gctgactttg gtttggcccg   3720
cgacatcctg gacagggagt actatagtgt tcaacagcat cgccacgctc gcctacctgt   3780
gaagtggatg gcgctggaga gcctgcagac ctatagattt accaccaagt ctgatgtgtg   3840
gtcatttggt gtgctgctgt gggaactgct gacacggggt gccccaccat accgccacat   3900
tgaccctttt gaccttaccc acttcctggc ccagggtcgg cgcctgcccc agcctgagta   3960
ttgccctgat tctctgtacc aagtgatgca gcaatgctgg gaggcagacc cagcagtgcg   4020
acccaccttc agagtactag tgggggaggt ggagcagata gtgtctgcac tgcttgggga   4080
ccattatgtg cagctgccag caacctacat gaacttgggc cccagcacct cgcatgagat   4140
gaatgtgcgt ccagaacagc cgcagttctc acccatgcca gggaatgtac gccggccccg   4200
gccactctca gagcctcctc ggcccacttg acttagttct tgggctggac ctgcttagct   4260
gccttgagct aaccccaagg ctgcctctgg gccatgccag gccagagcag tggccctcca   4320
ccttgttcct gccctttaac tttcagaggc aataggtaaa tgggcccatt aggtccctca   4380
ctccacagag tgagccagtg agggcagtcc tgcaacatgt atttatggag tgcctgctgt   4440
ggaccctgtc ttctgggcac agtggactca gcagtgacca caccaacact gacccttgaa   4500
ccaataaagg aacaaatgac tattaaagca caaaaaaaaa a                        4541
```

<210> SEQ ID NO 37
<211> LENGTH: 5920
<212> TYPE: DNA
<213> ORGANISM: Homo sapiens

<400> SEQUENCE: 37
gcgctgcccg cctcgtcccc acccccccaa cccccgcgcc cgccctcgga cagtccctgc 60
tcgcccgcgc gctgcagccc catctcctag cggcagccca ggcgcggagg gagcgagtcc 120
gccccgaggt aggtccagga cgggcgcaca gcagcagccg aggctggccg ggagagggag 180
gaagaggatg gcagggccac gccccagccc atgggccagg ctgctcctgg cagccttgat 240
cagcgtcagc ctctctggga ccttggcaaa ccgctgcaag aaggccccag tgaagagctg 300
cacggagtgt gtccgtgtgg ataaggactg cgcctactgc acagacgaga tgttcaggga 360
ccggcgctgc aacacccagg cggagctgct ggccgcgggc tgccagcggg agagcatcgt 420
ggtcatggag agcagcttcc aaatcacaga ggagacccag attgacacca ccctgcggcg 480
cagccagatg tccccccaag gcctgcgggt ccgtctgcgg cccggtgagg agcggcattt 540
tgagctggag gtgtttgagc cactggagag ccccgtggac ctgtacatcc tcatggactt 600
ctccaactcc atgtccgatg atctggacaa cctcaagaag atggggcaga acctggctcg 660
ggtcctgagc cagctcacca gcgactacac tattggattt ggcaagtttg tggacaaagt 720
cagcgtcccg cagacggaca tgaggcctga gaagctgaag gagccctggc ccaacagtga 780
cccccccttc tccttcaaga acgtcatcag cctgacagaa gatgtggatg agttccggaa 840
taaactgcag ggagagcgga tctcaggcaa cctggatgct cctgagggcg gcttcgatgc 900
catcctgcag acagctgtgt gcacgaggga cattggctgg cgcccggaca gcacccacct 960
gctggtcttc tccaccgagt cagccttcca ctatgaggct gatggcgcca acgtgctggc 1020
tggcatcatg agccgcaacg atgaacggtg ccacctggac accacgggca cctacaccca 1080
gtacaggaca caggactacc cgtcggtgcc caccctggtg cgcctgctcg ccaagcacaa 1140
catcatcccc atctttgctg tcaccaacta ctcctatagc tactacgaga agcttcacac 1200
ctatttccct gtctcctcac tgggggtgct gcaggaggac tcgtccaaca tcgtggagct 1260
gctggaggag gccttcaatc ggatccgctc caacctggac atccgggccc tagacagccc 1320
ccgaggcctt cggacagagg tcacctccaa gatgttccag aagacgagga ctgggtcctt 1380
tcacatccgg cggggggaag tgggtatata ccaggtgcag ctgcgggccc ttgagcacgt 1440
ggatgggacg cacgtgtgcc agctgccgga ggaccagaag ggcaacatcc atctgaaacc 1500
ttccttctcc gacggcctca agatggacgc gggcatcatc tgtgatgtgt gcacctgcga 1560
gctgcaaaaa gaggtgcggt cagctcgctg cagcttcaac ggagacttcg tgtgcggaca 1620
gtgtgtgtgc agcgagggct ggagtggcca gacctgcaac tgctccaccg gctctctgag 1680
tgacattcag ccctgcctgc gggagggcga ggacaagccg tgctccggcc gtggggagtg 1740
ccagtgcggg cactgtgtgt gctacggcga aggccgctac gagggtcagt tctgcgagta 1800
tgacaacttc cagtgtcccc gcacttccgg gttcctctgc aatgaccgag gacgctgctc 1860
catgggccag tgtgtgtgtg agcctggttg gacaggccca agctgtgact gtcccctcag 1920
caatgccacc tgcatcgaca gcaatggggg catctgtaat ggacgtggcc actgtgagtg 1980
tggccgctgc cactgccacc agcagtcgct ctacacggac accatctgcg agatcaacta 2040
ctcggcgatc cacccgggcc tctgcgagga cctacgctcc tgcgtgcagt gccaggcgtg 2100
gggcaccggc gagaagaagg ggcgcacgtg tgaggaatgc aacttcaagg tcaagatggt 2160
ggacgagctt aagagagccg aggaggtggt ggtgcgctgc tccttccggg acgaggatga 2220
cgactgcacc tacagctaca ccatggaagg tgacggcgcc cctgggccca acagcactgt 2280

-continued

```
cctggtgcac aagaagaagg actgccctcc gggctccttc tggtggctca tccccctgct   2340
cctcctcctc ctgccgctcc tggccctgct actgctgcta tgctggaagt actgtgcctg   2400
ctgcaaggcc tgcctggcac ttctcccgtg ctgcaaccga ggtcacatgg tgggctttaa   2460
ggaagaccac tacatgctgc gggagaacct gatggcctct gaccacttgg acacgcccat   2520
gctgcgcagc gggaacctca agggccgtga cgtggtccgc tggaaggtca ccaacaacat   2580
gcagcggcct ggctttgcca ctcatgccgc cagcatcaac cccacagagc tggtgcccta   2640
cgggctgtcc ttgcgcctgg cccgcctttg caccgagaac ctgctgaagc ctgacactcg   2700
ggagtgcgcc cagctgcgcc aggaggtgga ggagaacctg aacgaggtct acaggcagat   2760
ctccggtgta cacaagctcc agcagaccaa gttccggcag cagcccaatg ccgggaaaaa   2820
gcaagaccac accattgtgg acacagtgct gatggcgccc cgctcggcca agccggccct   2880
gctgaagctt acagagaagc aggtggaaca gagggccttc cacgacctca aggtggcccc   2940
cggctactac accctcactg cagaccagga cgcccggggc atggtggagt tccaggaggg   3000
cgtggagctg gtggacgtac gggtgcccct ctttatccgg cctgaggatg acgacgagaa   3060
gcagctgctg gtggaggcca tcgacgtgcc cgcaggcact gccaccctcg gccgccgcct   3120
ggtaaacatc accatcatca aggagcaagc cagagacgtg gtgtcctttg agcagcctga   3180
gttctcggtc agccgcgggg accaggtggc ccgcatccct gtcatccggc gtgtcctgga   3240
cggcgggaag tcccaggtct cctaccgcac acaggatggc accgcgcagg gcaaccggga   3300
ctacatcccc gtggagggtg agctgctgtt ccagcctggg gaggcctgga aagagctgca   3360
ggtgaagctc ctggagctgc aagaagttga ctccctcctg cggggccgcc aggtccgccg   3420
tttccacgtc cagctcagca accctaagtt tggggcccac ctgggccagc cccactccac   3480
caccatcatc atcagggacc cagatgaact ggaccggagc ttcacgagtc agatgttgtc   3540
atcacagcca ccccctcacg gcgacctggg cgccccgcag aaccccaatg ctaaggccgc   3600
tgggtccagg aagatccatt tcaactggct gccccccttct ggcaagccaa tggggtacag   3660
ggtaaagtac tggattcagg gtgactccga atccgaagcc cacctgctcg acagcaaggt   3720
gccctcagtg gagctcacca acctgtaccc gtattgcgac tatgagatga aggtgtgcgc   3780
ctacggggct cagggcgagg gaccctacag ctccctggtg tcctgccgca cccaccagga   3840
agtgcccagc gagccagggc gtctggcctt caatgtcgtc tcctccacgg tgacccagct   3900
gagctgggct gagccggctg agaccaacgg tgagatcaca gcctacgagg tctgctatgg   3960
cctggtcaac gatgacaacc gacctattgg gcccatgaag aaagtgctgg ttgacaaccc   4020
taagaaccgg atgctgctta ttgagaacct tcgggagtcc cagccctacc gctacacggt   4080
gaaggcgcgc aacggggccg gctgggggcc tgagcgggag gccatcatca acctggccac   4140
ccagcccaag aggcccatgt ccatccccat catccctgac atccctatcg tggacgccca   4200
gagcggggag gactacgaca gcttccttat gtacagcgat gacgttctac gctctccatc   4260
gggcagccag aggcccagcg tctccgatga cactggctgc ggctggaagt tcgagcccct   4320
gctgggggag gagctggacc tgcggcgcgt cacgtggcgg ctgcccccgg agctcatccc   4380
gcgcctgtcg gccagcagcg ggcgctcctc cgacgccgag gcgccccacg ggcccccgga   4440
cgacggcggc gcgggcggga agggcggcag cctgccccgc agtgcgacac ccgggccccc   4500
cggagagcac ctggtgaatg gccggatgga ctttgccttc ccgggcagca ccaactccct   4560
gcacaggatg accacgacca gtgctgctgc ctatggcacc cacctgagcc cacacgtgcc   4620
ccaccgcgtg ctaagcacat cctccaccct cacacgggac tacaactcac tgacccgctc   4680
```

agaacactca cactcgacca cactgcccag ggactactcc accctcacct ccgtctcctc 4740
ccacgactct cgcctgactg ctggtgtgcc cgacacgccc acccgcctgg tgttctctgc 4800
cctggggccc acatctctca gagtgagctg gcaggagccg cggtgcgagc ggccgctgca 4860
gggctacagt gtggagtacc agctgctgaa cggcggtgag ctgcatcggc tcaacatccc 4920
caaccctgcc cagacctcgg tggtggtgga agacctcctg cccaaccact cctacgtgtt 4980
ccgcgtgcgg gcccagagcc aggaaggctg gggccgagag cgtgagggtg tcatcaccat 5040
tgaatcccag gtgcacccgc agagcccact gtgtcccctg ccaggctccg ccttcacttt 5100
gagcactccc agtgccccag gcccgctggt gttcactgcc ctgagcccag actcgctgca 5160
gctgagctgg gagcggccac ggaggcccaa tggggatatc gtcggctacc tggtgacctg 5220
tgagatggcc caaggaggag ggccagccac cgcattccgg gtggatggag acagccccga 5280
gagccggctg accgtgccgg gcctcagcga gaacgtgccc tacaagttca aggtgcaggc 5340
caggaccact gagggcttcg ggccagagcg cgagggcatc atcaccatag agtcccagga 5400
tggaggaccc ttcccgcagc tgggcagccg tgccgggctc ttccagcacc cgctgcaaag 5460
cgagtacagc agcatcacca ccacccacac cagcgccacc gagcccttcc tagtggatgg 5520
gctgaccctg gggcccagc acctggaggc aggcggctcc ctcacccggc atgtgaccca 5580
ggagtttgtg agccggacac tgaccaccag cggaaccctt agcacccaca tggaccaaca 5640
gttcttccaa acttgaccgc accctgcccc accccgcca cgtcccacta ggcgtcctcc 5700
cgactcctct cccggagcct cctcagctac tccatccttg cacccctggg ggcccagccc 5760
acccgcatgc acagagcagg ggctaggtgt ctcctgggag gcatgaaggg ggcaaggtcc 5820
gtcctctgtg ggcccaaacc tatttgtaac caaagagctg ggagcagcac aaggacccag 5880
cctttgttct gcacttaata aatggttttg ctactgctaa 5920

<210> SEQ ID NO 38
<211> LENGTH: 1620
<212> TYPE: DNA
<213> ORGANISM: Homo sapiens

<400> SEQUENCE: 38
gggtggggaa gcttagagac cggtgaggga gcagagctgg ggcgcctgtg tacagggata 60
gagcccggcg gcagcagggc gcggcttccc tttcccgggg cctggggccg caatcaggtg 120
gagtcgagag gccggaggag gggcaggagg aaggggtgcg gtcgcgatcc ggacccggag 180
ccagcgcgga gcacctgcgc ccgcggctga caccttcgct cgcagtttgt tcgcagttta 240
ctcgcacacc agtttccccc accgcgcttt ggattagtgt gatctcagct caaggcaaag 300
gtgggatatc atggcatcta tctgggttgg acaccgagga acagtaagag attatccaga 360
ctttagccca tcagtggatg ctgaagctat tcagaaagca atcagaggaa ttggaactga 420
tgagaaaatg ctcatcagca ttctgactga gaggtcaaat gcacagcggc agctgattgt 480
taaggaatat caagcagcat atggaaagga gctgaaagat gacttgaagg gtgatctctc 540
tggccacttt gagcatctca tggtggccct agtgactcca ccagcagtct ttgatgcaaa 600
gcagctaaag aaatccatga agggcgcggg aacaaacgaa gatgccttga ttgaaatctt 660
aactaccagg acaagcaggc aaatgaagga tatctctcaa gcctattata cagtatacaa 720
gaagagtctt ggagatgaca ttagttccga aacatctggt gacttccgga aagctctgtt 780
gactttggca gatggcagaa gagatgaaag tctgaaagtg gatgagcatc tggccaaaca 840
agatgcccag attctctata aagctggtga gaacagatgg ggcacggatg aagacaaatt 900
cactgagatc ctgtgtttaa ggagctttcc tcaattaaaa ctaacatttg atgaatacag 960
aaatatcagc caaaaggaca ttgtggacag cataaaagga gaattatctg ggcattttga 1020
agacttactg ttggccatag ttaattgtgt gaggaacacg ccggcctttt tagccgaaag 1080
actgcatcga gccttgaagg gtattggaac tgatgagttt actctgaacc gaataatggt 1140
gtccagatca gaaattgacc ttttggacat tcgaacagag ttcaagaagc attatggcta 1200
ttccctatat tcagcaatta aatcggatac ttctggagac tatgaaatca cactcttaaa 1260
aatctgtggt ggagatgact gaaccaagaa gataatctcc aaaggtccac gatgggcttt 1320
cccaacagct ccaccttact tcttctcata ctatttaaga gaacaagcaa atataaacag 1380
caacttgtgt tcctaacagg aattttcatt gttctataac aacaacaaca aaagcgatta 1440
ttattttaga gcatctcatt tataatgtag cagctcataa atgaaattga aaatggtatt 1500
aaagatctgc aactactatc caacttatat ttctgctttc aaagttaaga atctttatag 1560
ttctactcca ttaaatataa agcaagataa taaaaattgt tgcttttgtt aaaagtaaaa 1620

<210> SEQ ID NO 39
<211> LENGTH: 955
<212> TYPE: DNA
<213> ORGANISM: Homo sapiens

<400> SEQUENCE: 39
tgcagactga tatggattca ccactgctaa cacctcctgg ttggaactac aggaatagaa 60
ctggaaaggg aaaaaaggca gcattcacca catcccaatc ctgaatccaa gagtctaaga 120
tagtccccca ctcctatctc aggcttagag gattagatta atctcctgga gggaagactc 180
ttccttgaaa cattttttt tatctgcctg tagctattgg gataattcgg gaaatccaca 240
gggacagttc aagtcatctt tgtcctctac tttctgttgc actctcagcc ttgttctctt 300
tttagaaact gcatggtaac tattatatag ctaaagaaga gcattctgac ctctgccctg 360
ggacttcctg gatcctcctc ttcttataaa tacaagggca gagctggtat cccggggagc 420
caggaagcag tgagcccagg agtcctcggc cagccctgcc tgcccaccag gaggatgaag 480
gtctccgtgg ctgccctctc ctgcctcatg cttgttgctg tccttggatc ccaggcccag 540
ttcataaatg atgcagagac agagttaatg atgtcaaagc ttccactgga aaatccagta 600
gttctgaaca gctttcactt tgctgctgac tgctgcacct cctacatctc acaaagcatc 660
ccgtgttcac tcatgaaaag ttattttgaa acgagcagcg agtgctccaa gccaggtgtc 720
atattcctca ccaagaaggg gcggcaagtc tgtgccaaac ccagtggtcc gggagttcag 780
gattgcatga aaaagctgaa gccctactca atataataat aaagagacaa aagaggccag 840
ccacccacct ccaacacctc ctgtgagttt cttggtctga aatacttaaa aaatatatat 900
attgttgtgt ctggtaatga aagtaatgca tctaataaag agtattcaat ttttt 955

<210> SEQ ID NO 40
<211> LENGTH: 1738
<212> TYPE: DNA
<213> ORGANISM: Homo sapiens

<400> SEQUENCE: 40 cggggggta ctgtgcgagc cctcaaggag gtggctgttc tgtagctgga gagctccgtg 60
ggtggcagga ctgaacttga acaccagaaa caaccccaa gccttgtgac ctgggaggca 120
ggaggcgggt ctgtctccct gggacttggg tggctgagcc gaggtactcg ggaccctgtc 180
ccgcgcatgg cagagtggct cctcacagcc tgaagctcat ccttctgcac gggccagcca 240
ggccagcaca gaggcaccag ggcagcagtg cacacaggtc cccggggacc ccaccatgtg 300
gagcggatgg tggctgtggc cccttgtggc cgtctgcact gcagacttct ttcgggacga 360
ggcagagagg atcatgaggg actcccctgt cattgatggg cacaatgacc tcccctggca 420
gctgctggat atgttcaaca accggctgca ggacgagagg gccaacctga ccaccttggc 480
cggcacacac accaacatcc ccaagctgag ggccggcttt gtgggaggcc agttctggtc 540
cgtgtacacg ccctgcgaca cccagaacaa agacgccgtg cggaggacgc tggagcagat 600
ggacgtggtc caccgcatgt gccggatgta cccggagacc ttcctgtatg tcaccagcag 660
tgcaggcatt cggcaggcct tccgggaagg gaaggtggcc agcctgatcg gcgtggaggg 720
cggccactcc attgacagca gtttgggcgt cctgcgggca ctctatcagc tgggcatgcg 780
gtacctgacc ctcacccaca gctgcaacac gccctgggct gacaactggc tggtggacac 840
gggagacagc gagccccaga gccaaggctt gtcacccttt gggcagcgtg tggtgaagga 900
gctgaaccgt ctgggggtcc tcatcgactt ggctcacgtg tctgtggcca ccatgaaggc 960
caccctgcag ctgtccagag ccccggtcat cttcagccac tcctcggcct acagcgtgtg 1020
cgcaagccgg cgcaacgtgc ctgacgacgt cctgaggctg gtgaaacaga cagacagcct 1080
ggtgatggtg aacttctaca acaattacat ttcctgcacc aacaaggcca acctgtccca 1140
agtggccgac catctggatc acatcaagga ggtggcagga gccagagccg tgggttttgg 1200
tggggacttt gatggtgttc caagggtccc tgaggggctg gaggacgtct ccaagtatcc 1260
agacctgatc gctgagctgc tcaggaggaa ctggacggag gcggaggtca agggcgcact 1320
ggctgacaac ctgctgaggg tcttcgaggc tgtggaacag gccagcaacc tcacacaggc 1380
tcccgaggag gagcccatcc cgctggacca gctgggtggc tcctgcagga cccattacgg 1440
ctactcctct ggggcttcca gcctccatcg ccactggggg ctcctgctgg cctccctcgc 1500
tcccctggtc ctctgtctgt ctctcctgtg aaacctggga gaccagagtc ccctttaggg 1560
ttcccggagc tccgggaaga cccgcccatc ccaggactcc agatgccagg agccctgctg 1620
cccacatgca aggaccagca tctcctgaga ggacgcctgg gcttacctgg ggggcaggat 1680
gcctggggac agttcaggac acacacacag taggcccgca ataaaagcaa caccccctt 1738

<210> SEQ ID NO 41
<211> LENGTH: 1132
<212> TYPE: DNA
<213> ORGANISM: Homo sapiens

<400> SEQUENCE: 41
agccatggca ggcccccgat acccagtttc agtgcaaggg gcagccctgg tgcagatcaa 60
gaggctccaa acgtttgcct tctctgtgcg ctggtcagac ggcagcgaca ccttcgtgcg 120
caggagttgg gacgaattca ggcagctcaa gaagaccctc aaggagacct tcccggtgga 180
ggcgggcctg ctgcggagat ctgaccgcgt tctcccaaag cttctcgatg caccactgtt 240
gggacgcgtg gggcgcacga gccgcggcct ggcgcgcctg cagctgttgg aaacctattc 300
tcggaggctg ctggcgactg cagagcgcgt ggcacggagc ccgacgatca ctggcttctt 360
cgcaccgcaa cccctggacc tggagcccgc gctgccaccc ggcagccggg tgatcctgcc 420
caccccagag gagcagcctc tttctcgcgc tgcgggccgc ctctccatcc acagtctgga 480
ggctcagagc ctgcgctgcc tgcagccctt ctgtacccag gacacgcggg ataggccttt 540
tcaggcgcag gcccaggaga gcctggacgt gctgctgcgg cacccctcag gctggtggct 600
ggtggagaac gaagaccggc agaccgcctg gtttccagcg ccctacctgg aggaggcggc 660
cccgggccaa ggccgggagg gaggcccgtc cctagggagc agcggtcccc agttctgtgc 720
ttcccgcgcc tacgagagca gccgcgcaga tgagctgtcc gtgcccgcgg gggcgcgcgt 780
gcgcgtgttg gaaacgtcag accgcggctg gtggctatgc aggtacggcg accgggcggg 840
cctactcccc gcggtgctgc tgcggccgga agggctgggc gctctcctga gcgggacggg 900
gttccgtgga ggagacgacc cggcgggtga ggcccggggc ttccctgaac cctcccaggc 960
caccgcccct ccccccaccg tgcccacccg accttcgccg ggcgccatcc agagccgctg 1020
ctgcaccgtc acacgcaggg ccctggagcg gcgcccacgg cgccagggcc gccctcgagg 1080
gtgcgtggac tctgtgccgc accccacgac ggagcagtga gcgcgaggat cc 1132

<210> SEQ ID NO 42
<211> LENGTH: 656
<212> TYPE: DNA
<213> ORGANISM: Homo sapiens

<400> SEQUENCE: 42
gggaacacat ccaagcttaa gacggtgagg tcagcttcac attctcagga actctccttc 60
tttgggtctg gctgaagttg aggatctctt actctctagg ccacggaatt aacccgagca 120
ggcatggagg cctctgctct cacctcatca gcagtgacca gtgtggccaa agtggtcagg 180
gtggcctctg gctctgccgt agttttgccc ctggccagga ttgctacagt tgtgattgga 240
ggagttgtgg ctgtgcccat ggtgctcagt gccatgggct tcactgcggc gggaatcgcc 300
tcgtcctcca tagcagccaa gatgatgtcc gcggcggcca ttgccaatgg gggtggagtt 360
gcctcgggca gccttgtggc tactctgcag tcactgggag caactggact ctccggattg 420
accaagttca tcctgggctc cattgggtct gccattgcgg ctgtcattgc gaggttctac 480
tagctccctg cccctcgccc tgcagagaag agaaccatgc caggggagaa ggcacccagc 540
catcctgacc cagcgaggag ccaactatcc caaatatacc tggggtgaaa tataccaaat 600
tctgcatctc cagaggaaaa taagaaataa agatgaattg ttgcaactct tcaaaa 656

<210> SEQ ID NO 43
<211> LENGTH: 2164
<212> TYPE: DNA
<213> ORGANISM: Homo sapiens

<400> SEQUENCE: 43
acctctgggc agagaaacaa agctctatat gcacagccca gcaaagagca gcacacagct 60
gaaagaaaaa ctcagaagac agagctgaaa aagaaaactg gtgatggatc tcattccaaa 120
ctttgccatg gaaacatggg ttcttgtggc taccagcctg gtactcctct atatttatgg 180
gacccattca cataaacttt ttaagaagct gggaattcct gggccaaccc ctctgccttt 240
tctgggaact attttgttct accttagggg tctttggaat tttgacagag aatgtaatga 300
aaaatacgga gaaatgtggg ggctgtatga ggggcaacag cccatgctgg tcatcatgga 360
tcccgacatg atcaaaacag tgttagtgaa agaatgttac tctgtcttca caaaccagat 420
gcctttaggt ccaatgggat ttctgaaaag tgccttaagt tttgctgaag atgaagaatg 480
gaagagaata cgaacattgc tatctccagc tttcaccagt gtaaaattca aggaaatggt 540
ccccatcatt tcccaatgtg gagatatgtt ggtgagaagc ctgaggcagg aagcagagaa 600
cagcaagtcc atcaacttga aagatttctt tggggcctac accatggatg taatcactgg 660
cacattattt ggagtgaact tggattctct caacaatcca caagatccct ttctgaaaaa 720
tatgaagaag cttttaaaat tggatttttt ggatcccttt ttactcttaa tatcactctt 780
tccatttctt accccagttt ttgaagccct aaatatcggt ttgtttccaa aagatgttac 840
ccattttta aaaaattcca ttgaaaggat gaaagaaagt cgcctcaaag ataaacaaaa 900
gcatcgagta gatttctttc aacagatgat cgactcccag aattccaaag aaacaaagtc 960
ccataaagct ctgtctgatc tggagcttgt ggcccagtca attatcatca tttttgctgc 1020
ctatgacaca actagcacca ctctcccctt cattatgtat gaactggcca ctcaccctga 1080
tgtccagcag aaactgcagg aggagattga cgcagtttta cccaataagg cacctgtcac 1140
ctacgatgcc ctggtacaga tggagtacct tgacatggtg gtgaatgaaa cgctcagatt 1200
attcccagtt gttagtagag ttacgagagt ctgcaagaaa gatattgaaa tcaatggagt 1260
gttcattccc aaagggttag cagtgatggt tccaatctat gctcttcacc atgacccaaa 1320
gtactggaca gagcctgaga agttctgccc tgaaaggttc agtaagaaga acaaggacag 1380
catagatctt tacagataca taccttttgg agctggaccc cgaaactgca ttggcatgag 1440
gtttgctctc acaaacataa aacttgctgt cattagagca ctgcagaact tctccttcaa 1500
accttgtaaa gagactcaga tcccactgaa attagacaat ctaccaattc ttcaaccaga 1560
aaaacctatt gttctaaaag tgcacttaag agatgggatt acaagtggac cctgactttc 1620
cctaaggact tccactttgt tcaagaaagc tgtatcccag aacactagac acttcaaatt 1680
gttttgtgaa taaaactcag aaatgaagat gagcttaatt aacctagtat actgggtgaa 1740
taattagaaa ttctctacat tcattgagct ctcattgtct gggtagagta ttacacgttg 1800
catactacaa agcaggtgac aaatcaatgc caaataagta cagtcatctt ctctagttct 1860
cataagacta tctccccgcc acctatagtt agtaccctca agtcctcctg agctgtgatc 1920
agagaataaa catttctcaa caattttacc aacaattttt aatgaaaagg aaaattatac 1980
ttgtgattct cgtagtgaca tttatattac atgttccatt tgtgatattc tataataagt 2040
attatattga gaaagtcaac aagcacctct ttacaaaact gttatctgat gtcttcctgc 2100
atattaagga tgaatctaca gaattagatc aataaggatc aacaaataaa tatttttggt 2160
catt 2164

<210> SEQ ID NO 44
<211> LENGTH: 4380
<212> TYPE: DNA
<213> ORGANISM: Homo sapiens

<400> SEQUENCE: 44
gtggcggctt cgcccgcgag tccagaggca ggcgagcagc tcggtcgccc ccaccggccc 60
catggcagcc cccggcgccc cagctgagta cggctacatc cggaccgtcc tgggccagca 120
gatcctggga caactggaca gctccagcct ggcgctgccc tccgaggcca agctgaagct 180
ggcggggagc agcggccgcg gcggccagac agtcaagagc ctgcggatcc aggagcaggt 240
gcagcagacc ctcgcccgga agggccgcag ctccgtgggc aacggaaatc ttcaccgaac 300
cagcagtgtt cctgagtatg tctacaacct acacttggtt gaaaatgatt ttgttggagg 360
ccgttcccct gttcctaaaa cctatgacat gctaaaggct ggcacaactg ccacttatga 420
aggtcgctgg ggaagaggaa cagcacagta cagctcccag aagtccgtgg aagaaaggtc 480
cttgaggcat cctctgagga gactggagat ttctcctgac agcagcccgg agagggctca 540

-continued

```
ctacacgcac agcgattacc agtacagcca gagaagccag gctgggcaca ccctgcacca    600
ccaagaaagc aggcgggccg ccctcctagt gccaccgaga tatgctcgtt ccgagatcgt    660
gggggtcagc cgtgctggca ccacaagcag gcagcgccac tttgacacat accacagaca    720
gtaccagcat ggctctgtta gcgacaccgt tttgacagc atccctgcca acccggccct    780
gctcacgtac cccaggccag ggaccagccg cagcatgggc aacctcttgg agaaggagaa    840
ctacctgacg gcagggctca ctgtcgggca ggtcaggccg ctggtgcccc tgcagcccgt    900
cactcagaac agggcttcca ggtcctcctg gcatcagagc tccttccaca gcacccgcac    960
gctgagggaa gctgggccca gtgtcgccgt ggattccagc gggaggagag cgcacttgac   1020
tgtcggccag gcggccgcag ggggaagtgg gaatctgctc actgagagaa gcactttcac   1080
tgactcccag ctggggaatg cagacatgga gatgactctg gagcgagcag tgagtatgct   1140
cgaggcagac cacatgccgc catccaggat ttctgctgca gctactttca tacagcacga   1200
gtgcttccag aaatctgaag ctcggaagag ggttaaccag cttcgtggca tcctcaagct   1260
tctgcagctc ctaaaagttc agaatgaaga cgttcagcga gctgtgtgtg ggccttgag   1320
aaacttagta tttgaagaca atgacaacaa attggaggtg gctgaactaa atggggtacc   1380
tcggctgctc caggtgctga agcaaaccag agacttggag actaaaaaac aaataacaga   1440
ccatacagtc aatttaagaa gtaggaatgg ctggccgggc gcggtggctc acgcctgtaa   1500
tcccagcact ttgggaggcc aaggcgggcg gatcacgagg tcaggagttc gagaccagcc   1560
tgaccaacat ggtttgctgt ggaatttgtc atctaatgac aaactcaaga atctcatgat   1620
aacagaagca ttgcttacgc tgacggagaa tatcatcatc ccctttttctg ggtggcctga   1680
aggagactac ccaaaagcaa atggtttgct cgattttgac atattctaca acgtcactgg   1740
atgcctaaga aacatgagtt ctgctggcgc tgatgggaga aaagcgatga gaagatgtga   1800
cggactcatt gactcactgg tccattatgt cagaggaacc attgcagatt accagccaga   1860
tgacaaggcc acggagaatt gtgtgtgcat tcttcataac ctctcctacc agctggaggc   1920
agagctccca gagaaatatt cccagaatat ctatattcaa aaccggaata tccagactga   1980
caacaacaaa agtattggat gttttggcag tcgaagcagg aaagtaaaag agcaatacca   2040
ggacgtgccg atgccggagg aaaagagcaa ccccaagggc gtggagtggc tgtggcattc   2100
cattgttata aggatgtatc tgtccttgat cgccaaaagt gtccgcaact acacacaaga   2160
agcatcctta ggagctctgc agaacctcac ggccggaagt ggaccaatgc cgacatcagt   2220
ggctcagaca gttgtccaga aggaaagtgg cctgcagcac acccgaaaga tgctgcatgt   2280
tggtgaccca agtgtgaaaa agacagccat ctcgctgctg aggaatctgt cccggaatct   2340
ttctctgcag aatgaaattg ccaaagaaac tctccctgat ttggtttcca tcattcctga   2400
cacagtcccg agtactgacc ttctcattga aactacagcc tctgcctgtt acacattgaa   2460
caacataatc caaaacagtt accagaatgc acgcgacctt ctaaacaccg gggcatcca   2520
gaaaattatg gccattagtg caggcgatgc ctatgcctcc aacaaagcaa gtaaagctgc   2580
ttccgtcctt ctgtattctc tgtgggcaca cacggaactg catcatgcct acaagaaggc   2640
tcagtttaag aagacagatt ttgtcaacag ccggactgcc aaagcctacc actcccttaa   2700
agactgagga aaatgacaaa gtattctcgg ctgcaaaaat ccccaaagga aaacacctat   2760
ttttctacta cccagcccaa gaaacctcaa aagcatgcct tgtttctatc cttctctatt   2820
tccgtggtcc cctgaatcca gaaaacaaat agaacataat tttatgagtc ttccagaaga   2880
cctttgcaag tttgccacca gtagataccg gccacaggct cgacaaatag tggtctttgt   2940
```

-continued

```
tattagggct tatggtacat ggcttcctgg aatcaaaatg tgaattcatg tggaagggac   3000

attaatccaa taaataagga aagaagctgt tgcattactg ggattttaaa agtttgattt   3060

acatttatat tccttttctg gttcccatgt tttgtcactc atgtgcacat tgcttcgcca   3120

ttgggcctcc agtgtattgt tctgcagtgt tgaaacagaa tggaaatgac aagaaatatc   3180

tgcagttatc caggagaaag tataatggca aaattattgg tttctttctt tactttgtgc   3240

ttgtttttat ccccttgggt tgtttttctc tgatttttaa ataaacttaa gaaatttaga   3300

ttacagagta tgcatgactg taagaaaaag aaattgagag gaagtgatca tagcaaatta   3360

aagaagtctt ttcctcccag aacttaaagt aaaataaaaa ataaataaat aaataaaatc   3420

ttttccacag agaaaggcaa ctgtgatgat aaaatttaac gttcccccaa acactgagtc   3480

aatgagattt ttctcaggag atactttacc tataacaacg ccgttaaatc caaatctctt   3540

ctaaacgatg gcattctatg taatgccttt cctggacttt tttggccact gccctggact   3600

agtgaaagaa tggactctat ctttatctgc aagaggaact aaggccttct atcagactgc   3660

ctggccagcc tggggcactg aaaatacggc tcatgttaat gagttacatt atcagccagc   3720

ccagccttgc ccaccattta agaaatatca cagagccact agatctcata tgatcttctt   3780

caagccatta ttttaactca agaaaactct agagaagaaa agtgaagaag tcatgttgaa   3840

gaagatgtaa gaatgtgtca agaccatcca gaaatgatat gagaaatact gatattttaa   3900

atggttgaca tcatccagcg aaatgaatct acattaaatg ttgttttaac tgcgctatga   3960

ttaaaaccat tcatatagag ttagtcttta caactactat tctgttattt tttttttaa   4020

tctgacaaca tttgtcctaa gtaagataag caaaaaaatt cttcaactcc ttttggcaag   4080

aaaactgtaa cagaaaataa attttgaatg tgtacttaag tctttattat atttgaagca   4140

atttttttc aattttaaaa gctgaatgaa gacaacttag gttgctaacc tagttcaaaa   4200

tgaaattatt tagataccaa tttttaaaat actggagaga atttatatgt ctttttccag   4260

agttctgatg ataagcattt ggagtgcatt tattcctcca gataataaat gtgtgttcag   4320

aactttttgt gtttttaag gcattaataa agccttcgat aatattaaat acaaaatgaa   4380
```

METHODS FOR DETERMINING CANCER RESISTANCE TO HISTONE DEACETYLASE INHIBITORS

RELATED APPLICATIONS

This application is a continuation of U.S. Ser. No. 12/022,977, filed Jan. 30, 2008, now U.S. Pat. No. 7,838,234, which claims the benefit of U.S. Provisional Patent Application No. 60/887,318, entitled "Methods for determining cancer resistance to histone deacetylase inhibitors," filed Jan. 30, 2007, and U.S. Provisional Patent Application No. 60/911,855 entitled "Methods for determining cancer resistance to histone deacetylase inhibitors," filed Apr. 13, 2007, all of which are incorporated by reference in their entirety.

BACKGROUND OF THE INVENTION

The highly heterogeneous response of the same type of cancer (e.g., colon cancer) to a given anti-cancer compound in different patients is one of the most vexing and tragic problems of modern medicine. It is widely thought that human genetic and epigenetic diversity underlies much of the variation in response to chemotherapy. Thus, there is an ongoing effort to identify in the human population the molecular genetic correlates (i.e., molecular signatures) of cancer resistance and sensitivity to specific therapeutic agents. It is hoped that such efforts will ultimately enable physicians to predetermine the likelihood that a patient's cancer can be effectively treated with a particular anti-cancer compound.

SUMMARY OF THE INVENTION

Described herein are methods and compositions for classifying a cancer in a patient as resistant or sensitive to a histone deacetylase inhibitor (HDACi) compound by (i) comparing the expression levels of at least four biomarker genes to a first set of biomarker gene expression level values, which was determined in cancer cells known to be resistant to the HDACi compound, or by comparing the expression levels to a second set of biomarker gene expression level values, which was determined in cancer cells known to be sensitive to the HDACi compound, and (ii) indicating that the cancer is sensitive to the HDACi compound if the biomarker gene expression levels are significantly lower than the first set of expression level values, or indicating that the cancer is resistant to the HDACi compound if the biomarker gene expression levels are greater than the second set of expression level values. The referred-to biomarker genes include PTPN3, ABCC3, SARG, PPAP2C, NPDC1, CTEN, RAB25, HEPH, TPMT, PKP3, GALNT5, CALML4, GALNT12, TPK1, DEFA6, EPLIN, CLIC5, PERP, SYK, SLC12A2, GUCY2C, TM4SF4, TGFA, FGFBP1, PTK6, EVA1, EPHA2, ITGA6, TNFRSF21, TM4SF3, IL18, BMP4, SMPDL3B, TMPRSS2, GDA, MST1R, ITGB4, ANXA3, CCL15, DPEP1, NOXO1, IF127, CYP3A43, and PKP2.

Accordingly, in one aspect provided herein is a method for classifying a cancer in a patient, comprising comparing the expression levels of at least four biomarker genes in the cancer to expression level to a first or second set of expression level threshold values for the biomarker genes, and indicating that the cancer is sensitive to a HDAC inhibitor if the expression levels of the biomarker genes are lower than the first set of expression level threshold values, or indicating that the cancer is resistant to a HDAC inhibitor if the expression levels are greater than the second set of expression level threshold values, wherein the at least four biomarker genes are selected from PTPN3, ABCC3, SARG, PPAP2C, NPDC1, CTEN, RAB25, HEPH, TPMT, PKP3, GALNT5, CALML4, GALNT12, TPK1, DEFA6, EPLIN, CLIC5, PERP, SYK, SLC12A2, GUCY2C, TM4SF4, TGFA, FGFBP1, PTK6, EVA1, EPHA2, ITGA6, TNFRSF21, TM4SF3, IL18, BMP4, SMPDL3B, TMPRSS2, GDA, MST1R, ITGB4, ANXA3, CCL15, DPEP1, NOXO1, IF127, CYP3A43, and PKP2. In some embodiments, the at least four marker genes are selected from DEFA6, ITGB4, TM4SF4, SYK, PPAP2C, RAB25, HEPH, NOXO1, TM4SF4, PTPN3, EPHA2, FGFBP1, ABCC3, TPMT, IL18, and DPEP1. In some embodiments, the at least four biomarker genes include at least one of DEFA6, RAB25, TM4SF4, or IL18. In some embodiments, the at least four biomarker genes include DEFA6, ITGB4, TM4SF3, SYK, PPAP2C, and RAB25. In some embodiments, the at least four biomarker genes include DEFA6, ITGB4, TM4SF4, SYK, PPAP2C, RAB25, HEPH, NOXO1, TM4SF4, PTPN3, EPHA2, FGFBP1, ABCC3, TPMT, IL18, and DPEP1. In some embodiments, one or more of the above-mentioned expression levels is an mRNA expression level. In some embodiments, one or more of the expression levels is a polypeptide expression level. In some embodiments, the patient's cancer is a colon cancer. In some embodiments, the method for classifying the cancer further comprises determining the level of expression of the at least four biomarker genes in the cancer prior to the step of comparing. In some embodiments, the referred-to HDAC inhibitor is PCI-24781. In some embodiments, the expression levels of the at least four biomarker genes are compared to the first set and the second set of biomarker gene expression level threshold level values.

In another aspect provided herein is a method for classifying a cancer in a patient, comprising determining the expression levels of at least four biomarker genes in the cancer, comparing the expression levels of the at least four biomarker genes in the cancer to expression level to a first or second set of expression level threshold values for the biomarker genes, and indicating that the cancer is sensitive to a HDAC inhibitor if the expression levels of the biomarker genes are lower than the first set of expression level threshold values, or indicating that the cancer is resistant to a HDAC inhibitor if the expression levels are greater than the second set of expression level threshold values, wherein the at least four biomarker genes are selected from PTPN3, ABCC3, SARG, PPAP2C, NPDC1, CTEN, RAB25, HEPH, TPMT, PKP3, GALNT5, CALML4, GALNT12, TPK1, DEFA6, EPLIN, CLIC5, PERP, SYK, SLC12A2, GUCY2C, TM4SF4, TGFA, FGFBP1, PTK6, EVA1, EPHA2, ITGA6, TNFRSF21, TM4SF3, IL18, BMP4, SMPDL3B, TMPRSS2, GDA, MST1R, ITGB4, ANXA3, CCL15, DPEP1, NOXO1, IF127, CYP3A43, and PKP2.

In some embodiments, at least one of the at least four marker genes are selected from DEFA6, ITGB4, TM4SF4, SYK, PPAP2C, RAB25, HEPH, NOXO1, TM4SF4, PTPN3, EPHA2, FGFBP1, ABCC3, TPMT, IL18, and DPEP1. In some embodiments, the at least four biomarker genes include at least one of DEFA6, RAB25, TM4SF4, or IL18. In some embodiments, the at least four biomarker genes include DEFA6, ITGB4, TM4SF3, SYK, PPAP2C, and RAB25. In some embodiments, the at least four biomarker genes include DEFA6, ITGB4, TM4SF4, SYK, PPAP2C, RAB25, HEPH, NOXO1, TM4SF4, PTPN3, EPHA2, FGFBP1, ABCC3, TPMT, IL18, and DPEP1. In some embodiments, wherein one or more of the expression levels of the referred-to biomarker genes is an mRNA expression level. In some embodiments, one or more of the expression levels is a polypeptide expression level. In some embodiments, the patient's cancer is a colon cancer. In some embodiments, the HDAC inhibitor is PCI-24781. In some embodiments, the method further comprises prescribing or administering an HDAC inhibitor to the patient based on the comparison of the biomarker gene expression levels. In some embodiments, the expression levels of the at least four biomarker genes are compared to the first set and the second set of biomarker gene expression level threshold level values.

In a further aspect provided herein is an isolated population of nucleic acids comprising a plurality of nucleic acids derived from a cancer cell, wherein the cancer cell is a type of cancer cell that is sensitive to an HDAC inhibitor compound. In some embodiments, the isolated population contains RNAs. In some embodiments, the isolated population contains cDNAs. In some embodiments, the referred-to HDAC inhibitor is PCI-24781. In some embodiments, the referred-to cancer cell was isolated from a population of cells grown in vitro. In some embodiments, the cancer cell is a colon carcinoma cell. In some embodiments, the colon carcinoma cell is derived from colon carcinoma 81059261097, R4498160614, R5456781761, R7424107588, or R0948311023. In some embodiments, the nucleotide sequences of at least four of DEFA6, ITGB4, TM4SF4, SYK, PPAP2C, RAB25, HEPH, NOXO1, TM4SF4, PTPN3, EPHA2, FGFBP1, ABCC3, TPMT, IL18, or DPEP1 are represented in the isolated population of nucleic acids.

In a related aspect provided herein is an isolated population of nucleic acids comprising a plurality of nucleic acids derived from a cancer cell, wherein the cancer cell is a type of cancer cell that is resistant to an HDAC inhibitor compound. In some embodiments, the isolated population contains RNAs. In some embodiments, the isolated population contains cDNAs. In some embodiments, the referred-to HDAC inhibitor is PCI-24781. In some embodiments, the referred-to cancer cell was isolated from a population of cells grown in vitro. In some embodiments, the cancer cell is a colon carcinoma cell. In some embodiments, the colon carcinoma cell is derived from colon carcinoma R1059261097, R4498160614, R5456781761, R7424107588, or R0948311023. In some embodiments, the nucleotide sequences of at least four of DEFA6, ITGB4, TM4SF4, SYK, PPAP2C, RAB25, HEPH, NOXO1, TM4SF4, PTPN3, EPHA2, FGFBP1, ABCC3, TPMT, IL18, or DPEP1 are represented in the isolated population of nucleic acids.

In some embodiments provided herein is a kit comprising the above referred-to isolated population of nucleic acids and an insert indicating the ratio of a biomarker gene nucleic acid level in the population to an internal expression control gene nucleic acid level in the population.

In some embodiments provided herein is a kit comprising the above referred-to isolated population of nucleic acids and an insert indicating the ratio of a biomarker gene nucleic acid level in the population to a nucleic acid level of the biomarker gene in a population of nucleic acids derived from a cancer cell, wherein the cancer cell is a type of cancer cell that is sensitive to the HDAC inhibitor compound.

In another aspect provided herein is a method for generating an expression level reference population of nucleic acids for expression profiling, comprising deriving an isolated population of nucleic acids from a cancer cell, wherein the cancer cell is a type of cancer cell that is sensitive to an HDAC inhibitor compound. In some embodiments, the isolated population contains RNAs. In some embodiments, the isolated population contains cDNAs. In some embodiments, the just-referred to HDAC inhibitor compound is PCI-24781. In some embodiments, the cancer cell is present in a biopsy sample. In some embodiments, the cancer cell is present in a population of cells grown in vitro. In some embodiments, the cancer cell is a colon carcinoma cell. In some embodiments, the carcinoma cell is derived from colon carcinoma R1059261097, 84498160614, R5456781761, R7424107588, or R0948311023. In some embodiments, the nucleotide sequences of at least four of DEFA6, ITGB4, TM4SF4, SYK, PPAP2C, RAB25, HEPH, NOXO1, TM4SF4, PTPN3, EPHA2, FGFBP1, ABCC3, TPMT, IL18, or DPEP1 are represented in the above referred-to isolated population of nucleic acids. In some embodiments, the method further comprises determining, prior to the isolating step, that the type of cancer cell is sensitive to an HDAC inhibitor compound. In some embodiments, the type of cancer cell determined to be sensitive to an HDAC inhibitor compound HDAC inhibitor compound in vitro. In some embodiments, the HDAC inhibitor compound is PCI-24781.

In a related aspect provided herein is a method for generating an expression level reference sample for expression profiling, comprising deriving an isolated population of nucleic acids from a cancer cell, wherein the cancer cell is a type of cancer cell that is resistant to an HDAC inhibitor compound. In some embodiments, the isolated population contains RNAs. In some embodiments, the isolated population contains cDNAs. In some embodiments, the just-referred to HDAC inhibitor compound is PCI-24781. In some embodiments, the cancer cell is present in a biopsy sample. In some embodiments, the cancer cell is present in a population of cells grown in vitro. In some embodiments, the cancer cell is a colon carcinoma cell. In some embodiments, the carcinoma cell is derived from colon carcinoma R1059261097, R4498160614, R5456781761, R7424107588, or R0948311023. In some embodiments, the nucleotide sequences of at least four of DEFA6, ITGB4, TM4SF4, SYK, PPAP2C, RAB25, HEPH, NOXO1, TM4SF4, PTPN3, EPHA2, FGFBP1, ABCC3, TPMT, IL18, or DPEP1 are represented in the above referred-to isolated population of nucleic acids. In some embodiments, the method further comprises determining, prior to the isolating step, that the type of cancer cell is resistant to an HDAC inhibitor compound. In some embodiments, the type of cancer cell determined to be resistant to an HDAC inhibitor compound HDAC inhibitor compound in vitro. In some embodiments, the HDAC inhibitor compound is PCI-24781.

In another aspect provided herein is a human cancer cell line that is resistant to an HDAC inhibitor compound in vitro. In some embodiments, the human cell line expresses DEFA6, ITGB4, TM4SF4, SYK, PPAP2C, RAB25, HEPH, NOXO1, TM4SF4, PTPN3, EPHA2, FGFBP1, ABCC3, TPMT, IL18, and DPEP1. In some embodiments, the HDAC inhibitor compound to which the referred-to human cancer cell line is resistant is PCI-24781. In some embodiments, the PCI-24781-resistant human cancer cell line is resistant to a PCI-24781 concentration of at least about 1 μM. In some embodiments, the human cancer cell line is a colon carcinoma cell line. In some embodiments, the colon carcinoma cell line is 85247682266, R9866135153, R1078103114, or R4712781606.

In a further aspect provided herein is a method for increasing the likelihood of therapeutically effective treatment of a cancer with an HDAC inhibitor, comprising providing an indication that a cancer in a patient is sensitive to treatment with an HDAC inhibitor if expression levels of at least four biomarker genes in a sample from the patient's cancer are lower than expression level threshold values for the four biomarker genes, or providing an indication that the cancer is resistant to treatment with the HDAC inhibitor if the expression levels of the biomarker genes are higher than the expression level threshold values, wherein the at least four biomarker genes are selected from PTPN3, ABCC3, SARG, PPAP2C, NPDC1, CTEN, RAB25, HEPH, TPMT, PKP3, GALNT5, CALML4, GALNT12, TPK1, DEFA6, EPLIN, CLIC5, PERP, SYK, SLC12A2, GUCY2C, TM4SF4, TGFA, FGFBP1, PTK6, EVA1, EPHA2, ITGA6, TNFRSF21, TM4SF3, IL18, BMP4, SMPDL3B, TMPRSS2, GDA, MST1R, ITGB4, ANXA3, CCL15, DPEP1, NOXO1, IFI27, CYP3A43, and PKP2, whereby the likelihood of therapeutically effective treatment of the cancer with the HDAC inhibitor is increased. In some embodiments, the indication is provided in a digital medium. In some embodiments, the indication is provided in a hardcopy medium. In some embodiments, the indication is a biomedical publication reference. In some embodiments, the indication refers to expression levels of at least two of the biomarker genes. In some embodiments, the at least four biomarker genes include DEFA6, RAB25, TM4SF4, or IL18. In some embodiments, the at least four biomarker genes include DEFA6, ITGB4, TM4SF3, SYK, PPAP2C, and RAB25. In some embodiments, the at least four biomarker genes include DEFA6, ITGB4, TM4SF4, SYK, PPAP2C, RAB25, HEPH, NOXO1, TM4SF4, PTPN3, EPHA2, FGFBP1, ABCC3, TPMT, IL18, and DPEP1. In some embodiments, the cancer is colon cancer. In some embodiments, the HDAC inhibitor is PCI-24781.

In yet another aspect provided herein is a method for optimizing selection of an anti-cancer agent for treating a cancer in combination with an HDAC inhibitor compound, by: (i) comparing a first set of biomarker genes the expression of which is correlated to resistance or sensitivity of the cancer to the anti-cancer agent to a second set of biomarker genes the expression of which is correlated with resistance to the HDAC inhibitor compound; and (ii) selecting the anti-cancer agent for treatment of the cancer in combination with the HDAC inhibitor if the biomarker genes in the first set are different from the biomarker genes in the second set, where the biomarker genes in the second set are DEFA6, ITGB4, TM4SF4, SYK, PPAP2C, RAB25, HEPH, NOXO1, TM4SF4, PTPN3, EPHA2, FGFBP1, ABCC3, TPMT, IL18, and DPEP1. In some embodiments, the method further comprises comparing the expression level of the second set of biomarker genes in a plurality of cancer cells treated with the HDAC inhibitor together with a second anti-cancer agent.

In a further aspect provided herein is an indication of the likelihood of a therapeutically effective treatment of a cancer with an HDAC inhibitor compound, comprising a means of communicating an interpretation of expression levels of at least four biomarker genes selected from DEFA6, ITGB4, TM4SF4, SYK, PPAP2C, RAB25, HEPH, NOXO1, TM4SF4, PTPN3, EPHA2, FGFBP1, ABCC3, TPMT, IL18, and DPEP. In some embodiments, the indication further comprises the expression levels of the at least four biomarker genes. In some embodiments, the means of communicating is a paper document or an electronic document. In some embodiments, the interpretation includes a biomedical publication reference. In some embodiments, the interpretation includes a graph. In some embodiments, the interpretation includes information that indicates that a cancer in a patient is sensitive to treatment with an HDAC inhibitor if expression levels of the biomarker genes in a sample from the patient's cancer are lower than expression level threshold values for the four biomarker genes, or information that indicates that the cancer is resistant to treatment with the HDAC inhibitor if the expression levels of the biomarker genes are higher than the expression level threshold values.

In another aspect provided herein is a method for determining the likelihood of effectively treating a cancer in a patient with an HDAC inhibitor compound, comprising: (i) determining in the cancer the expression levels of at least four biomarker genes selected from DEFA6, ITGB4, TM4SF4, SYK, PPAP2C, RAB25, HEPH, NOXO1, TM4SF4, PTPN3, EPHA2, FGFBP1, ABCC3, TPMT, IL18, and DPEP; and (ii) comparing the expression levels of that at least four biomarker genes in the cancer to expression levels of the at least four biomarker genes in an expression level reference sample derived from cancer cells previously determined to be resistant to the HDAC inhibitor compound, wherein the likelihood of effectively treating the cancer is higher if the expression level of the at least four biomarkers in the cancer from the patient is lower than the expression levels of the biomarker genes in the expression level reference sample. In some embodiments, the method further comprises selecting an anti-cancer agent other than an HDAC inhibitor compound for treating the cancer.

In yet another aspect provided herein is a method for classifying a cancer in a patient, comprising comparing the expression levels of at least four biomarker genes in the cancer to a first or second set of expression level values for the biomarker genes, and for each comparison assigning a probability to the biomarker gene expression level that the cancer in the patient is resistant to a histone deacetylase inhibitor compound, where: (i) the first set of expression level values were measured in cancer cells determined to be resistant to the histone deacetylase inhibitor compound; (ii) the second set of expression level values were measured in cancer cells determined to be sensitive to the histone deacetylase inhibitor compound; (iii) the assigned probability is inversely proportional to a negative deviation of the biomarker gene expression level from the first set of expression level values and directly proportional to a positive deviation of the biomarker gene expression level from the second set of expression level values; and (iv) the at least four biomarker genes are selected from PTPN3, ABCC3, SARG, PPAP2C, NPDC1, CTEN, RAB25, HEPH, TPMT, PKP3, GALNT5, CALML4, GALNT12, TPK1, DEFA6, EPLIN, CLIC5, PERP, SYK, SLC12A2, GUCY2C, TM4SF4, TGFA, FGFBP1, PTK6, EVA1, EPHA2, ITGA6, TNFRSF21, TM4SF3, IL18, BMP4, SMPDL3B, TMPRSS2, GDA, MST1R, ITGB4, ANXA3; CCL15, DPEP1, NOXO1, IF127, CYP3A43, and PKP2.

In another aspect provided herein is a method for classifying a population of cells, comprising comparing the expression levels of at least four biomarker genes in the population of cells to a first or second set of expression level threshold values for the biomarker genes, and indicating that the population of cells is sensitive to a HDAC inhibitor if the expression levels of the biomarker genes are lower than the first set of expression level threshold values, or indicating that the population of cells is resistant to a HDAC inhibitor if the expression levels are greater than the second set of expression level threshold values, wherein the at least four biomarker genes are selected from PTPN3, ABCC3, SARG, PPAP2C, NPDC1, CTEN, RAB25, HEPH, TPMT, PKP3, GALNT5, CALML4, GALNT12, TPK1, DEFA6, EPLIN, CLIC5, PERP, SYK, SLC12A2, GUCY2C, TM4SF4, TGFA, FGFBP1, PTK6, EVA1, EPHA2, ITGA6, TNFRSF21, TM4SF3, IL18, BMP4, SMPDL3B, TMPRSS2, GDA, MST1R, ITGB4, ANXA3, CCL15, DPEP1, NOXO1, IF127, CYP3A43, and PKP2.

In another aspect provided herein is a method for determining HDAC inhibition in vivo, comprising determining the expression level of an HDAC inhibitor-responsive biomarker gene in a biological sample obtained from a subject after the subject had been administered an HDAC inhibitor compound, wherein the HDAC inhibitor-responsive biomarker genes are any of the genes listed in Table 5.

In another aspect provided herein is a method for determining the most responsive tissues and the tumors derived therefrom to an HDAC inhibitor, comprising: (i) providing a first tissue of the tissue type (including blood) at a first time point and administration of HDAC inhibitor compound to the first tissue by any applicable route at a first time point, (ii) providing a second tissue of the tissue type (including blood) at a second time point and administration of HDAC inhibitor compound to the second tissue by any applicable route at a second time point, and (iii) determining expression profiles in the first and second tissues for any of the genes listed in Table 5.

In a further aspect provided herein is a method for classifying one or more cells, comprising determining the expression levels of no more than four to fifty biomarker genes in the one or more cells, wherein at least four of the biomarker genes are selected from PTPN3, ABCC3, SARG, PPAP2C, NPDC1, CTEN, RAB25, HEPH, TPMT, PKP3, GALNT5, CALML4, GALNT12, TPK1, DEFA6, EPLIN, CLIC5, PERP, SYK, SLC12A2, GUCY2C, TM4SF4, TGFA, FGFBP1, PTK6, EVA1, EPHA2, ITGA6, TNFRSF21, TM4SF3, IL18, BMP4, SMPDL3B, TMPRSS2, GDA, MST1R, ITGB4, ANXA3, CCL15, DPEP1, NOXO1, IF127, CYP3A43, and PKP2. In some embodiments, the method further comprises comparing the expression levels of the four to fifty biomarker genes to a first or second set of expression level threshold values for the biomarker genes, and indicating that the cancer is sensitive to a HDAC inhibitor if the expression levels of the biomarker genes are lower than the first set of expression level threshold values, or indicating that the cancer is resistant to a HDAC inhibitor if the expression levels are greater than the second set of expression level threshold values. In some embodiments, the one or more cells are cancer cells. In some embodiments, the at least four biomarker genes are selected from DEFA6, ITGB4, TM4SF4, SYK, PPAP2C, RAB25, HEPH, NOXO1, TM4SF4, PTPN3, EPHA2, FGFBP1, ABCC3, TPMT, IL18, and DPEP. In some embodiments, the method further comprises determining the expression levels of no more than four to twenty biomarker genes. In some embodiments, the method comprises determining the expression levels of no more than four biomarker genes. In some embodiments, the four biomarker genes consist of DEFA6, RAB25, TM4SF4, and IL18.

In yet another aspect provided herein is a nucleic acid hybridization array comprising nucleic acid probes that hybridize under high stringency hybridization conditions to nucleic acids of no more than four to fifty biomarker genes, wherein at least four of the biomarker genes are selected from PTPN3, ABCC3, SARG, PPAP2C, NPDC1, CTEN, RAB25, HEPH, TPMT, PKP3, GALNT5, CALML4, GALNT12, TPK1, DEFA6, EPLIN, CLIC5, PERP, SYK, SLC12A2, GUCY2C, TM4SF4, TGFA, FGFBP1, PTK6, EVA1, EPHA2, ITGA6, TNFRSF21, TM4SF3, IL18, BMP4, SMPDL3B, TMPRSS2, GDA, MST1R, ITGB4, ANXA3, CCL15, DPEP1, NOXO1, IF127, CYP3A43, and PKP2. In some embodiments, the nucleic acid hybridization array comprises at least four biomarker genes selected from DEFA6, ITGB4, TM4SF4, SYK, PPAP2C, RAB25, HEPH, NOXO1, TM4SF4, PTPN3, EPHA2, FGFBP1, ABCC3, TPMT, IL18, and DPEP. In some embodiments, the at least four biomarker genes consist of DEFA6, RAB25, TM4SF4, and IL18.

It is to be understood that the methods and compositions described herein are not limited to the particular methodology, protocols, cell lines, constructs, and reagents described herein and as such may vary. It is also to be understood that the terminology used herein is for the purpose of describing particular embodiments only, and is not intended to limit the scope of the methods and compositions described herein, which will be limited only by the appended claims.

As used herein and in the appended claims, the singular forms "a," "an," and "the" include plural reference unless the context clearly indicates otherwise.

The term "biomarker gene" refers to a gene whose expression or activity yields at least one expression product the level of which is quantitatively correlated to a phenotypic state of interest (e.g., drug resistance, pathology).

The term "detectable label" refers to a label which is observable using analytical techniques including, but not limited to, fluorescence, chemiluminescence, electron-spin resonance, ultraviolet/visible absorbance spectroscopy, mass spectrometry, nuclear magnetic resonance, magnetic resonance, and electrochemical methods.

The terms "differentially expressed gene," "differential gene expression," and their synonyms, which are used interchangeably, refer to a gene whose expression is upregulated or downregulated in a first cell population relative to the expression of the same gene in a second population of cells. Such differences are evidenced by, e.g., a change in mRNA levels, surface expression, secretion or other partitioning of a polypeptide. Differential gene expression includes, in some embodiments, a comparison of expression between two or more genes or their gene products, or a comparison of the ratios of the expression between two or more genes or their gene products, or even a comparison of two differently processed products of the same gene, which differ between two populations of cells. Differential expression includes both quantitative, as well as qualitative, differences in the temporal or cellular expression pattern in a gene or its expression products among, for example, normal and diseased cells, or among cells which have undergone different disease events or disease stages, or cells that are significantly sensitive or resistant to certain therapeutic drugs.

The term "fluorophore" refers to a molecule which upon excitation emits photons and is thereby fluorescent.

The phrase "gene amplification" refers to a process by which multiple copies of a gene or gene fragment are formed in a particular cell or cell line. The duplicated region (a stretch of amplified DNA) is often referred to as "amplicon." Frequently, the amount of the messenger RNA (mRNA) produced, i.e., the level of gene expression, also increases in proportion to the number of copies made of the particular gene.

The term "gene expression profiling," unless otherwise specified, is used in the broadest sense, and includes methods of quantification of a gene's mRNA or nucleic acids derived therefrom, and/or protein levels or peptides derived therefrom and/or protein functions in a biological sample.

The term "high stringency hybridization" refers to hybridization conditions of incubating at 68° C. for an hour, followed by washing 3 times for 20 minutes each at room temperature in 2×SSC and 0.1% SDS and twice at 50° C. in 0.1×SSC and 0.1% SDS, or any art-recognized equivalent hybridization conditions.

The term "internal expression control gene" refers to a gene the expression level of which is known to or expected to be very similar in cells that differ in one or more phenotypes, or which have been subjected to differing experimental treatments. For example, the expression of the gene HDAC3 is shown to be to very similar in colon cancer cells that are resistant or sensitive to treatment with an HDACi compound.

The term "isolated" refers to separating and removing a component of interest from components not of interest. Isolated substances are optionally in either a dry or semi-dry state, or in solution, including but not limited to an aqueous solution. The isolated component is optionally in a homogeneous state or the isolated component is optionally a part of a pharmaceutical composition that comprises additional pharmaceutically acceptable carriers and/or excipients. Purity and homogeneity are determined, for example, using analytical chemistry techniques including, but not limited to, polyacrylamide gel electrophoresis or high performance liquid chromatography. In addition, when a component of interest is isolated and is the predominant species present in a preparation, the component is described herein as substantially purified. The term "purified," as used herein, refers to a component of interest which is at least 85% pure, at least 90% pure, at least 95% pure, at least 99% or greater pure. By way of example only, nucleic acids or proteins are "isolated" when such nucleic acids or proteins are free of at least some of the cellular components with which it is associated in the natural state, or that the nucleic acid or protein has been concentrated to a level greater than the concentration of its in vivo or in vitro production.

The term "label" refers to a substance which is incorporated into a compound and is readily detected, whereby its physical distribution is detected and/or monitored.

The term "microarray" refers to an ordered arrangement of hybridizable array elements, preferably polynucleotide probes, on a substrate.

The term "nucleic acid" or "nucleic acid probe," when used in singular or plural, generally refers to any polyribonucleotide or polydeoxyribonucleotide, which includes unmodified RNA or DNA or modified RNA or DNA. Thus, for instance, nucleic acids as defined herein include, without limitation, single- and double-stranded DNA, DNA including single- and double-stranded regions, single- and double-stranded RNA, and RNA including single- and double-stranded regions, hybrid molecules comprising DNA and RNA that are optionally single-stranded or, more typically, double-stranded or include single- and double-stranded regions. In addition, the term "nucleic acid" as used herein refers to triple-stranded regions comprising RNA or DNA or both RNA and DNA. The strands in such regions are optionally from the same molecule or from different molecules. The regions optionally include all of one or more of the molecules, but more typically involve only a region of some of the molecules. One of the molecules of a triple-helical region often is an oligonucleotide. The term "nucleic acid" specifically includes cDNAs. The term includes DNAs (including cDNAs) and RNAs that contain one or more modified bases. Thus, DNAs or RNAs with backbones modified for stability or for other reasons are "nucleic acids" as referred to herein. DNAs or RNAs comprising unusual bases, such as inosine, or modified bases, such as tritiated bases, are included within the term "nucleic acid" as defined herein. In general, the term "nucleic acid" embraces all chemically, enzymatically and/or metabolically modified forms of unmodified polynucleotides, as well as the chemical forms of DNA and RNA characteristic of viruses and cells, including simple and complex cells.

The term "oligonucleotide" refers to a relatively short polynucleotide, including, without limitation, single-stranded deoxyribonucleotides, single- or double-stranded ribonucleotides, RNA:DNA hybrids and double-stranded DNAs. Oligonucleotides, such as single-stranded DNA probe oligonucleotides, are often synthesized by chemical methods, for example using automated oligonucleotide synthesizers that are commercially available. However, oligonucleotides are optionally made by a variety of other methods, including in vitro recombinant DNA-mediated techniques and by expression of DNAs in cells and organisms.

The terms "prediction," "predicting," "prognostic," or "prognosis" are used herein to refer to the likelihood that a patient will respond either favorably or unfavorably to a drug (e.g., an anti-cancer compound) or set of drugs, and also the extent of those responses. The predictive methods of described herein are valuable tools in predicting if a patient suffering from a cancer is likely to respond favorably to an HDAC inhibitor compound treatment regimen alone or in combination with another therapeutic agent (e.g., a second anti-cancer compound).

The term "subject" or "patient" refers to an animal which is the object of treatment, observation or experiment. By way of example only, a subject includes, but is not limited to, a mammal including, but not limited to, a human.

The term "substantially purified" refers to a component of interest that is substantially or essentially free of other components which normally accompany or interact with the component of interest prior to purification. By way of example only, a component of interest is "substantially purified" when the preparation of the component of interest contains less than about 30%, less than about 25%, less than about 20%, less than about 15%, less than about 10%, less than about 5%, less than about 4%, less than about 3%, less than about 2%, or less than about 1% (by dry weight) of contaminating components. Thus, a "substantially purified" component of interest optionally has a purity level of about 70%, about 75%, about 80%, about 85%, about 90%, about 95%, about 96%, about 97%, about 98%, about 99% or greater.

The term "therapeutically effective amount" refers to the amount of a composition administered to a patient already suffering from a disease, condition or disorder, sufficient to cure or at least partially arrest, or relieve to some extent one or more of the symptoms of the disease, disorder or condition being treated. The effectiveness of such compositions depend conditions including, but not limited to, the severity and course of the disease, disorder or condition, previous therapy, the patient's health status and response to the drugs, and the judgment of the treating physician. By way of example only, therapeutically effective amounts are determined by methods, including but not limited to a dose escalation clinical trial.

The terms "treat," "treating" or "treatment," include alleviating, abating or ameliorating a disease or condition symptoms, preventing additional symptoms, ameliorating or preventing the underlying metabolic causes of symptoms, inhibiting the disease or condition, e.g., arresting the development of the disease or condition, relieving the disease or condition, causing regression of the disease or condition, relieving a condition caused by the disease or condition, or stopping the symptoms of the disease or condition. The terms "treat," "treating" or "treatment", include, but are not limited to, prophylactic and/or therapeutic treatments.

The term "tumor" or "cancer" refers to all neoplastic cell growth and proliferation, whether malignant or benign, and all pre-cancerous and cancerous cells and tissues.

Unless otherwise indicated, conventional methods of cell culture, protein chemistry, biochemistry, recombinant DNA techniques including gene amplification and hybridization techniques, mass spectroscopy, and pharmacology, are employed.

DETAILED DESCRIPTION OF THE INVENTION

Figure 1:
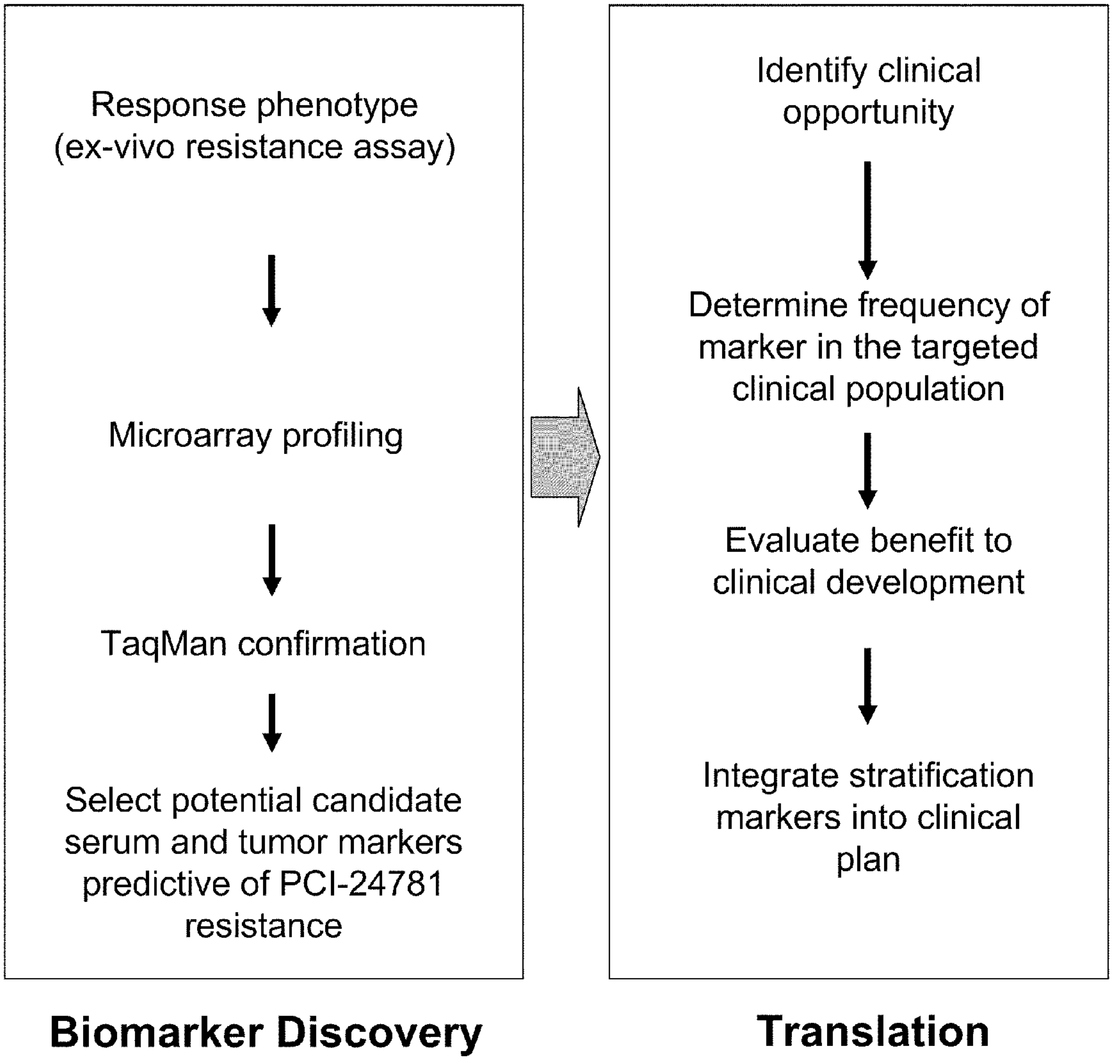
FIG. 1 is an illustrative schematic flow diagram of a method for identifying biomarker genes for HDACi compound resistance in cancer cells based on gene expression profiling, and the clinical application of expression profiling of the identified biomarker genes.

The methods described herein include classifying a cancer in a patient as resistant or sensitive to a histone deacetylase inhibitor (HDACi) compound by comparing the expression levels of at least four biomarker genes expressed in the cancer to biomarker gene expression level threshold values, as described herein. Where the expression levels of at least four biomarker genes are greater than the expression level threshold values, the cancer is indicated as being resistant to the HDACi compound. Conversely, if the expression levels of the at least four biomarker genes are lower than the expression level threshold values, the cancer is indicated to be sensitive to the HDACi compound.

Also described herein is a population of nucleic acids derived from a cancer cell, where the cancer cell is a type of cancer cell that is resistant to an HDACi compound. Further described herein is a population of nucleic acids derived from a cancer cell, where the cancer cell is a type of cancer cell that is sensitive to an HDACi compound. Also described herein are methods for generating these populations of nucleic acids. Such populations of nucleic acids are optionally used as expression level reference standards for setting biomarker gene expression threshold levels as described herein. Further described herein are cell lines determined to be resistant to an HDACi compound. Also described herein are cell lines determined to be sensitive to an HDACi compound.

Also described herein is a method for increasing the likelihood of therapeutically effective treatment of a cancer with an HDACi compound by providing an indication that a cancer is sensitive to treatment with an HDACi compound if the expression levels of at least four of the biomarker genes described herein are lower than the expression level threshold values for those biomarker genes, or providing an indication that a cancer is resistant to treatment with an HDACi compound if the expression levels of at least four of the biomarker genes described herein are higher than the expression level threshold values for those biomarker genes.

Further described herein are methods for optimizing selection of an anti-cancer agent for treating cancer in combination with an HDACi compound by comparing a first set of biomarker genes the expression of which is correlated to resistance or sensitivity of the cancer to the anti-cancer agent to a second set of biomarker genes the expression of which is correlated with resistance to the HDACi compound, and then selecting the anti-cancer agent for treatment of the cancer in combination with the HDAC inhibitor only if all of the biomarker genes in the first set are different from the biomarker genes in the second set.

Identification of HDACi Compound Resistance Biomarker Genes (HDACiR-BGs)

Described herein are methods for identifying genes whose expression levels in cancer cells are significantly and consistently correlated with resistance of the cells to an HDACi compound. Such genes are termed HDACi compound resistance biomarker genes (HDACiR-BGs). In an exemplary embodiment, HDACiR-BGs are identified as follows.

The ex-vivo response of primary tumor cells (e.g., colon cancer cells) from various patients to an HDAC inhibitor is determined by culturing the cells in the presence of varying concentrations of the HDACi compound.

After determining the HDACi compound sensitivity the cancer cells from each patient, mRNA expression profiles are determined for HDACi-resistant and sensitive tumors. Total RNA is isolated and fluorescent probes are prepared and hybridized to a whole genome cDNA microarray (e.g., Codelink Human Whole Genome oligonucleotide microarrays containing ~55,000 unique probes; GE Healthcare Bio-Sciences Corp., Piscataway, N.J.) according to the manufacturer's instructions. Following hybridization, the microarrays are scanned (e.g., in a GenePix 4000B scanner; Molecular Devices Corporation, Sunnyvale Calif.). The images are then processed with Codelink software and the data are normalized to the median.

The median-normalized microarray data are imported into a microarray data analysis program for principal component analysis (PCA) and hierarchical clustering analysis (e.g., Genespring software from Agilent). Multiple analysis methods are employed to provide additional confidence in the mRNA expression analysis. For multiple hypothesis correction, the q-values approach for false discovery rates (FDR) are optionally used as described in Storey et al. (2003), *Proc. Nat. Acad. Sci. USA,* 100:9440-9445. As a second analytical approach the Bayesian ANOVA approach described in Ishwaran et al. (2003), *J. Amer. Stat. Assoc.,* 98:438-455 is optionally used.

In the Bayesian ANOVA method, the contributions of irrelevant genes to the ANOVA model are selectively shrunk to balance total false detections against total false non-detections. The output is a Zcut score which identifies genes whose contribution to the ANOVA model is larger than the standard z-score. See Ishwaran et al., ibid., and the website at bamarray.com.

The just-described method and variants thereof is optionally used to identify biomarker genes for other specific phenotypic states, e.g., resistance to anti-cancer agents other than HDACi compounds.

HDACiR-BGs identified by the just-described methods include those listed in Table 1. The sequence for the mRNA of each of the listed genes is included herein in an appendix.

TABLE 1

HDACi Compound Resistance Biomarker Genes (HDACiR-BGs)

| Gene Name | Gene Symbol | GenBank Accession # | SEQ ID NO |
|---|---|---|---|
| PTPN3 | PTPN3 | AK096975 | 1 |
| ATP-binding cassette, sub-family C (CFTR/MRP), member 3 | ABCC3 | NM_020037 | 2 |
| specifically androgen-regulated protein | SARG | NM_023938 | 3 |
| phosphatidic acid phosphatase type 2C | PPAP2C | NM_177526 | 4 |
| neural proliferation, differentiation and control, 1 | NPDC1 | NM_015392 | 5 |
| C-terminal tensin-like | CTEN | NM_032865 | 6 |
| RAB25, member RAS oncogene family | RAB25 | NM_020387 | 7 |
| Hephaestin | HEPH | NM_138737 | 8 |
| thiopurine S-methyltransferase | TPMT | NM_000367 | 9 |
| plakophilin 3 | PKP3 | NM_007183 | 10 |
| UDP-N-acetyl-alpha-D-galactosamine: polypeptide N-acetylgalactosaminyltransferase 5 (GalNAc-T5) | GALNT5 | NM_014568 | 11 |
| calmodulin-like 4 | CALML4 | NM_033429 | 12 |
| UDP-N-acetyl-alpha-D-galactosamine: polypeptide N-acetylgalactosaminyltransferase 12 (GalNAc-T12) | GALNT12 | AK024865 | 13 |
| thiamin pyrophosphokinase 1 | TPK1 | NM_022445 | 14 |
| defensin, alpha 6, Paneth cell-specific | DEFA6 | NM_001926 | 15 |
| epithelial protein lost in neoplasm beta | EPLIN | NM_016357 | 16 |
| chloride intracellular channel 5 | CLIC5 | NM_016929 | 17 |
| PERP, TP53 apoptosis effector | PERP | NM_022121 | 18 |
| spleen tyrosine kinase | SYK | NM_003177 | 19 |
| solute carrier family 12 (sodium/potassium/chloride transporters), member 2 | SLC12A2 | NM_001046 | 20 |
| guanylate cyclase 2C (heat stable enterotoxin receptor) | GUCY2C | NM_004963 | 21 |
| transmembrane 4 superfamily member 4 | TM4SF4 | NM_004617 | 22 |
| transforming growth factor, alpha | TGFA | NM_003236 | 23 |
| fibroblast growth factor binding protein 1 | FGFBP1 | NM_005130 | 24 |
| PTK6 protein tyrosine kinase 6 | PTK6 | NM_005975 | 25 |
| epithelial V-like antigen 1 | EVA1 | NM_005797 | 26 |
| EPH receptor A2 | EPHA2 | NM_004431 | 27 |
| integrin, alpha 6 | ITGA6 | NM_000210 | 28 |
| tumor necrosis factor receptor superfamily, member 21 | TNFRSF21 | NM_014452 | 29 |
| transmembrane 4 superfamily member 3 | TM4SF3 | NM_004616 | 30 |
| interleukin 18 (interferon-gamma-inducing factor) | IL18 | NM_001562 | 31 |

TABLE 1-continued

| HDACi Compound Resistance Biomarker Genes (HDACiR-BGs) | | | |
|---|---|---|---|
| Gene Name | Gene Symbol | GenBank Accession # | SEQ ID NO |
| bone morphogenetic protein 4 | BMP4 | NM_130850 | 32 |
| sphingomyelin phosphodiesterase, acid-like 3B | SMPDL3B | NM_014474 | 33 |
| transmembrane protease, serine 2 | TMPRSS2 | NM_005656 | 34 |
| guanine deaminase | GDA | NM_004293 | 35 |
| macrophage stimulating 1 receptor (c-met-related tyrosine kinase) | MST1R | NM_002447 | 36 |
| integrin, beta 4 | ITGB4 | NM_000213 | 37 |
| annexin A3 | ANXA3 | NM_005139 | 38 |
| chemokine (C-C motif) ligand 15 | CCL15 | NM_032965 | 39 |
| dipeptidase 1 (renal) | DPEP1 | NM_004413 | 40 |
| NADPH oxidase organizer 1 | NOXO1 | NM_172167 | 41 |
| interferon, alpha-inducible protein 27 | IFI27 | NM_005532 | 42 |
| cytochrome P450, family 3, subfamily A, polypeptide 43 | CYP3A43 | NM_057095 | 43 |
| plakophilin 2 | PKP2 | NM_004572 | 44 |

Classification of Individual Patient Cancers as Resistant or Sensitive to an HDACi Compound In some embodiments, gene expression profiling is performed on a biological sample obtained from an individual patient suffering from a cancer (e.g., a colon cancer tumor) to classify the cancer in the patient as resistant or sensitive to an HDACi compound. The gene expression profiling includes profiling the expression of at least one of the HDACi compound resistance biomarker genes (HDACiR-BGs) listed in Table 1, which were identified as described herein.

In some embodiments the HDACiR-BG is selected from among DEFA6, TM4SF4, TGFA, FGFBP1, EPHA2, TNFRSF2, TM4SF3, IL18, TMPRSS2, and CCL15.

In some embodiments, at least four of the HDACiR-BGs are expression profiled. In some embodiments, at least one of the four HDACiR-BGs are selected from among DEFA6, ITGB4, TM4SF4, SYK, PPAP2C, RAB25, HEPH, NOXO1, TM4SF3, PTPN3, EPHA2, FGFBP1, ABCC3, TPMT, IL18, or DPEP1. In some embodiments, all of the at least four HDACiR-BGs are selected from among DEFA6, ITGB4, TM4SF4, SYK, PPAP2C, RAB25, HEPH, NOXO1, TM4SF3, PTPN3, EPHA2, FGFBP1, ABCC3, TPMT, IL18, or DPEP1.

In some embodiments, the expression of at least sixteen of the HDACiR-BGs is profiled. In some embodiments, the at least sixteen HDACiR-BGs include one or more of DEFA6, ITGB4, TM4SF4, SYK, PPAP2C, RAB25, HEPH, NOXO1, TM4SF3, PTPN3, EPHA2, FGFBP1, ABCC3, TPMT, IL18, or DPEP1. In some embodiments, the at least 16 HDACiR-BGs include DEFA6, ITGB4, TM4SF4, SYK, PPAP2C, RAB25, HEPH, NOXO1, TM4SF3, PTPN3, EPHA2, FGFBP1, ABCC3, TPMT, IL18, or DPEP1.

In various embodiments, the types of cancers and tumors that are optionally classified (from individual patients) for resistance or sensitivity to an HDACi compound include, but are not limited to, colorectal cancer, ovarian cancer, pancreatic cancer biliary tract cancer; bladder cancer; bone cancer; brain and CNS cancer; breast cancer; cervical cancer; choriocarcinoma; connective tissue cancer; cancer of the digestive system; endometrial cancer; esophageal cancer; eye cancer; cancer of the head and neck; gastric cancer; intra-epithelial neoplasm; kidney cancer; larynx cancer; leukemia; liver cancer; lung cancer (e.g., small cell and non-small cell); lymphoma including Hodgkin's and non-Hodgkin's lymphoma; melanoma; myeloma; neuroblastoma; oral cavity cancer (e.g., lip, tongue, mouth, and pharynx); prostate cancer; retinoblastoma; rhabdomyosarcoma; rectal cancer; renal cancer; cancer of the respiratory system; sarcoma; skin cancer; stomach cancer; testicular cancer; thyroid cancer; uterine cancer; cancer of the urinary system, as well as other carcinomas and sarcomas.

Types of cancer cells that are optionally classified in various embodiments include, but are not limited to, squamous cell papilloma, squamous cell carcinoma, basal cell tumor, basal cell carcinoma, transitional cell papilloma, transitional cell carcinoma, glandular epithelium adenoma, melanocytes glomus tumor, melanocytic nevus, malignant melanoma, fibroma, fibrosacroma, an adenocarcinoma, gastrinoma, malignant gastrinoma, an oncocytoma, cholangiocellular adenoma, cholangiocellular carcinoma, hepatocellular adenoma, hepatocellular carcinoma, renal tubular adenoma, renal cell carcinom (Grawitz tumor), myxoma, myxosarcoma, lipoma, liposarcoma, leiomyoma, leiomyosarcoma, rhabdomyoma, rhabdomyosarcoma, benign teratoma, malignant teratoma, hemangioma, hemangiosarcoma, Kaposi sarcoma, lymphangioma, lymphangiosarcoma, an osteoma, an osteosarcoma, an osteogenic sarcoma, cartilage chondroma, chondrosarcoma, meninges meningioma, malignant meningioma, oligoastrocytoma, an ependymoma, an astrocytoma, pilocytic astrocytoma, glioblastommultiforme, an oligodendroglioma, neuroblastoma, schwanoma, retinoblastoma, or neurofibroma. Other types of cancers and tumors include those described in reference sources, e.g., the "International Classification of Diseases for Oncology," 3rd Edition, International Association of Cancer Registries.

A biological sample is any biological sample that includes cellular material from which DNA, RNA or protein are optionally isolated, e.g., solid tissue samples, such as a biopsy specimen or tissue cultures or cells derived therefrom and the progeny thereof, blood and other liquid samples of biological origin, e.g., sputum (including saliva, buccal wash, or bronchial brush), stool, semen, urine, ascitic fluid, cerebral spinal fluid, bladder wash, or pleural fluid. The term "biological sample" also encompasses samples that have been manipulated in any way after their procurement, such as by treatment with reagents, solubilization, or enrichment for certain components. The term encompasses a clinical sample, and also includes cells in cell culture, cell supernatants, cell lysates, serum, plasma, biological fluids, and tissue samples, e.g., freshly collected tissue, frozen tissue, archived tissue, or biological fluids In some embodiments, the biological sample is a tumor biopsy (e.g., a core biopsy, a needle biopsy, or an excisional biopsy) containing one or more cancer cells. In one embodiment the biological sample is a population of cancer cells obtained by laser capture dissection from a tumor tissue section as described in, e.g., U.S. Pat. No. 6,040,139. Methods for optimizing tissue sample preparation and processing for expression profiling include, e.g., Bova et al. (2005), *Methods Mol. Med.,* 103:15-66.

In some embodiments, one or more cells (e.g., from a cultured cancer cell line), are classified by determining the expression levels of no more than four to fifty biomarker genes described herein., e.g., 5, 6, 7, 8, 9, 10, 12, 16, 18, 20, 24, 30, 32, 35, 40, 44, 45, 47, or any other number of biomarker genes from four to fifty. In some embodiments, four to fourty four of the biomarker genes are selected from Table 3, e.g., 5, 6, 7, 8, 9, 10, 12, 16, 18, 20, 24, 30, 32, 35, 40, or any other number of biomarker genes from four to fourty four is selected from Table 3. In some embodiments, at least four of the biomarker genes are selected from PTPN3, ABCC3, SARG, PPAP2C, NPDC1, CTEN, RAB25, HEPH, TPMT, PKP3, GALNT5, CALML4, GALNT12, TPK1, DEFA6, EPLIN, CLIC5, PERP, SYK, SLC12A2, GUCY2C, TM4SF4, TGFA, FGFBP1, PTK6, EVA1, EPHA2, ITGA6, TNFRSF21, TM4SF3, IL18, BMP4, SMPDL3B, TMPRSS2, GDA, MST1R, ITGB4, ANXA3, CCL15, DPEP1, NOXO1, IF127, CYP3A43, and PKP2. In some embodiments, the four to fifty biomarker comprises one or more genes selected from DEFA6, ITGB4, TM4SF4, SYK, PPAP2C, RAB25, HEPH, NOXO1, TM4SF4, PTPN3, EPHA2, FGFBP1, ABCC3, TPMT, IL18, and DPEP In some embodiments, classification of the cells comprises comparing the determined expression levels to a first or second set of expression level threshold values for the biomarker genes, and indicating that the one or more cells are sensitive to a HDAC inhibitor if the expression levels of the biomarker genes are lower than the first set of expression level threshold values, or indicating that the one or more cells are resistant to a HDAC inhibitor if the expression levels are greater than the second set of expression level threshold values. In some embodiments, the expression of no more than four to twenty biomarker genes is determined. In some embodiments, the expression levels of no more than four biomarker genes is determined. In some embodiments, the four biomarker genes the expression level of which is determined are: DEFA6, RAB25, TM4SF4, and IL18.

Methods for HDACiR-BG Expression Profiling

HDACiR-BG expression profiles are optionally generated by any convenient means for determining differential gene expression between two samples, e.g. quantitative hybridization of mRNA, labeled mRNA, amplified mRNA, cRNA, etc., quantitative PCR, ELISA for protein quantitation, and the like.

In some embodiments, HDACiR-BG mRNA levels (including cDNA copy or aRNA copies) are quantified. The expression profile is optionally generated from the initial nucleic acid sample using any convenient protocol. While a variety of different manners of generating expression profiles are known, such as those employed in the field of differential gene expression analysis, one representative and convenient type of protocol for generating expression profiles is array based gene expression profile generation protocols. Such applications are hybridization assays in which a nucleic acid that displays "probe" nucleic acids for each of the genes to be assayed/profiled in the profile to be generated is employed. In these assays, a sample of target nucleic acids is first prepared from the initial nucleic acid sample being assayed, where preparation optionally includes labeling of the target nucleic acids with a label, e.g., a member of signal producing system. Following target nucleic acid sample preparation, the sample is contacted with the array under hybridization conditions, whereby complexes are formed between target nucleic acids that are complementary to probe sequences attached to the array surface. HDACiR-BG hybridization complexes are then detected and quantified.

Specific hybridization technologies which are optionally practiced to generate the HDACiR-BG expression profiles employed in the methods described herein includes the technology described in U.S. Pat. Nos. 5,143,854; 5,288,644; 5,324,633; 5,432,049; 5,470,710; 5,492,806; 5,503,980; 5,510,270; 5,525,464; 5,547,839; 5,580,732; 5,661,028; 5,800,992; as well as WO 95/21265; WO 96/31622; WO 97/10365; WO 97/27317; EP 373 203; and EP 785 280. In these methods, an array of "probe" nucleic acids that includes a probe for each of the phenotype determinative genes whose expression is being assayed is contacted with target nucleic acids as described above. Contact is carried out under hybridization conditions, e.g., stringent hybridization conditions as those conditions are practiced in the art, and unbound nucleic acid is then removed. The resultant pattern of hybridized nucleic acid provides quantitative information regarding expression for each of the HDACiR-BGs that have been probed.

Evaluation of differences in expression values is optionally performed using any convenient methodology, e.g., by comparing digital images of the expression profiles, by comparing databases of expression data, etc. Patents describing ways of comparing expression profiles include, but are not limited to, U.S. Pat. Nos. 6,308,170 and 6,228,575 and U.S. patent application Ser. No. 10/858,867.

In some embodiments, the methods described herein are performed on nucleic acid hybridization arrays comprising nucleic acid probes that hybridize under high stringency hybridization conditions to nucleic acids of no more than four to fifty biomarker genes, e.g., 5, 6, 7, 8, 9, 10, 12, 16, 18, 20, 24, 30, 32, 35, 40, 44, 45, 47, or any other number of biomarker genes from four to fifty. In some embodiments, four to fourty four of the biomarker genes are selected from Table 3, e.g., 5, 6, 7, 8, 9, 10, 12, 16, 18, 20, 24, 30, 32, 35, 40, or any other number of biomarker genes from four to fourty four is selected from Table 3. In some embodiments, at least four of the biomarker genes for the array probes are selected from PTPN3, ABCC3, SARG, PPAP2C, NPDC1, CTEN, RAB25, HEPH, TPMT, PKP3, GALNT5, CALML4, GALNT12, TPK1, DEFA6, EPLIN, CLIC5, PERP, SYK, SLC12A2, GUCY2C, TM4SF4, TGFA, FGFBP1, PTK6, EVA1, EPHA2, ITGA6, TNFRSF21, TM4SF3, IL18, BMP4, SMPDL3B, TMPRSS2, GDA, MST1R, ITGB4, ANXA3, CCL15, DPEP1, NOXO1, IFI27, CYP3A43, and PKP2. In some embodiments, the at least four biomarker genes are selected from DEFA6, ITGB4, TM4SF4, SYK, PPAP2C, RAB25, HEPH, NOXO1, TM4SF4, PTPN3, EPHA2, FGFBP1, ABCC3, TPMT, IL18, and DPEP. In some embodiments, the at least four biomarker genes are DEFA6, RAB25, TM4SF4, and IL18.

Alternatively, non-array based methods for quantitating the levels of one or more nucleic acids in a sample are employed, including quantitative PCR, and the like.

In some embodiments, expression profiling of HDACiR-BGs expressed in a biological sample (e.g., a tumor biopsy) is done by a quantitative reverse transcription PCR assay (qRT-PCR). In this method, RNA from a biological sample is reverse transcribed to generate segments of cDNA which are then be amplified by gene-specific quantitative PCR. The rate of accumulation of specific PCR products is optionally correlated to the abundance of the corresponding RNA species in the original sample and thereby provide an indication of gene expression levels.

In one embodiment, the qPCR assay is a TaqMan™ assay. In brief, PCR typically utilizes the 5' exonuclease activity of Taq or Tth polymerase to hydrolyze a fluorescently-labelled hybridization probe bound to its target amplicon, but any enzyme with equivalent 5' exonuclease activity is optionally used. Two oligonucleotide primers are used to generate an amplicon typical of a PCR reaction. A third oligonucleotide, or probe, is designed to hybridize to a nucleotide sequence located between the two PCR primers. The probe is non-extendible by Taq DNA polymerase enzyme, and is 5' labeled with a reporter fluorescent dye and a 3' labeled with a quencher fluorescent dye. Any laser-induced emission from the reporter dye is quenched by the quenching dye when the two dyes are located close together as they are on the probe. During the amplification reaction, the Taq DNA polymerase enzyme cleaves the probe in a template-dependent manner. The resultant probe fragments disassociate in solution, and signal from the released reporter dye is free from the quenching effect of the second chromophore. One molecule of reporter dye is liberated for each new molecule synthesized, and detection of the unquenched reporter dye provides the basis for quantitative interpretation of the data.

qRT-PCR is optionally performed using commercially available equipment, such as, for example, the ABI PRISM 7900™ Sequence Detection System™ (Perkin-Elmer-Applied Biosystems, Foster City, Calif.), or LightCycler™. (Roche Molecular Biochemicals, Mannheim, Germany). In one embodiment, the 5' exonuclease procedure is run on a real-time quantitative PCR device such as the ABI PRISM 7900™ Sequence Detection System™ or one of the similar systems in this family of instruments. The system consists of a thermocycler, laser, charge-coupled device (CCD), camera and computer. The system amplifies samples in 96-well or 384 well formats on a thermocycler. During amplification, laser-induced fluorescent signal is collected in real-time through fiber optic cables for all reaction wells, and detected at the CCD. The system includes software for running the instrument and for analyzing the data.

Exonuclease assay data are initially expressed as a $C_T$ value, i.e., the PCR cycle at which the fluorescent signal is first recorded as statistically significant.

In order to minimize errors and the effects of sample-to-sample variation and process variability mRNA level measurements are generally normalized to the expression level of an internal expression control gene. Methods for normalizing qPCR assays include, see, e.g., the website at normalisation gene-quantification.info. The ideal internal expression control gene is one that is expressed at a relatively constant level among different patients or subjects, and is unaffected by the experimental treatment.

In some embodiments, the internal expression control gene is RNA polymerase II (GenBank Accession No. X74870).

In other embodiments, the internal expression control gene is HDAC3 (NM_003883). In further embodiments, the internal expression control gene is ZNF217 (NM_006526).

In some embodiments, HDAiR-BG mRNA expression levels for each sample are normalized by the total amount of RNA in each sample. The amount of RNA in a sample is optionally determined, e.g., by UV-spectrophotometry or by using an RNA detection reagent, e.g., RiboGreen® from Invitrogen (Carlsbad, Calif.).

Where the HDACiR-BG expression profile to be determined is a protein expression profile, any convenient protein quantitation protocol is optionally employed, where the levels of one or more proteins in the assayed sample are determined. Representative methods include, but are not limited to; proteomic arrays, mass spectrometry, or standard immunoassays (e.g., RIA or ELISA). See, e.g., the methods set forth in R. Scopes, *Protein Purification*, Springer-Verlag, N.Y. (1982); Sandana (1997) *Bioseparation of Proteins*, Academic Press, Inc.; Bollag et al. (1996) Protein Methods. 2nd Edition Wiley-Liss, NY; Walker (1996) The Protein Protocols Handbook Humana Press, NJ, Harris and Angal (1990) Protein Purification: Principles and Practice 3rd Edition Springer Verlag, NY; Janson and Ryden (1998) Protein Purification: Principles, High Resolution Methods and Applications, Second Edition Wiley-VCH, NY; and Satinder Ahuja ed., *Handbook of Bioseparations*, Academic Press (2000); Harlow et al., *Antibodies: A Laboratory Manual*, Cold Spring Harbor Laboratory, Cold Spring Harbor, N.Y., 353-355 (1988).

Proteomic expression profiling methods detection methods include various multidimensional electrophoresis methods (e.g., 2-D gel electrophoresis), mass spectrometry based methods e.g., SELDI, MALDI, electrospray, etc.), or surface plasmon resonance methods. For example, in MALDI, a sample is usually mixed with an appropriate matrix, placed on the surface of a probe and examined by laser desorption/ionization. See, e.g., U.S. Pat. Nos. 5,045,694, 5,202,561, and 6,111,251. Similarly, for SELDI, a first aliquot is contacted with a solid support-bound (e.g., substrate-bound) adsorbent. A substrate is typically a probe (e.g., a biochip) that is optionally positioned in an interrogatable relationship with a gas phase ion spectrometer. SELDI has been applied to diagnostic proteomics. See, e.g. Issaq et al. (2003), *Anal. Chem.* 75: 149A-155A.

In one embodiment, any of the just-described protein detection methods are used to determine the expression level of one or more HDACiR-BG proteins that are known to be secreted proteins, e.g., DEFA6, TM4SF4, TM4SF3, TGFA, FGFBP1, EPHA2, TNFRSF2, IL18, CCL15, or TMPRSS2.

Expression Level Reference Samples

In some embodiments, expression profiles of HDACiR-BGs in a biological sample of interest (e.g., a colon cancer biopsy) are compared to HDACiR-BG expression profiles in an expression level reference sample. The expression level reference sample is a biological sample derived from one or more cancer patients determined to be suffering from a particular cancer or tumor for which sensitivity or resistance to treatment with an HDACi compound (e.g., PCI-24781) has been determined. In other words, the expression level reference sample serves as a standard with which to compare expression level values for each HDACiR-BG in a test sample. The deviation of HDACiR-BG expression levels from the expression level values in a reference sample indicates whether the cancer in the patient from the biological sample was derived is sensitive or resistant to treatment with an HDACi compound. In some embodiments, HDACiR-BG threshold expression level values are optionally set based on one or more statistical criteria for deviation from HDACiR-BG expression level values in an expression level reference sample, e.g., two or more SDs away from the value for a reference sample HDACiR-BG expression level.

In some embodiments, the expression level reference sample is a "negative" reference sample, i.e., a sample derived from a patient having a cancer or tumor determined to be sensitive to an HDACi compound. Thus, where expression levels of multiple HDACiR-BGs (e.g. at least 4, 5, 6, 8, 10, 12, or 16) are significantly greater than the threshold expression level values based on the negative reference sample, the patient's cancer is indicated as resistant to the HDACi compound.

In some embodiments, the expression level reference sample is a "positive" reference sample, i.e., a sample derived from a patient having a cancer or tumor determined to be resistant to an HDACi compound. Thus, where expression levels of multiple HDACiR-BGs (e.g. at least 4, 5, 6, 8, 10, 12, or 16) are significantly lower than the threshold expression level values based on the negative reference sample, the patient's cancer is indicated as sensitive to the HDACi compound.

In some embodiments, HDACiR-BG expression profiles are compared to those in both positive and negative reference samples.

In some embodiments, HDACiR-BGs expression level measurements are performed in parallel for the biological sample of interest and the (positive or negative) expression level reference. For example, where an array hybridization method is used, HDACiR-BG mRNA levels in the biological sample of interest and in an expression level reference sample are optionally measured simultaneously by separately labeling nucleic acid populations (e.g., mRNA, cDNA, aRNA populations) from each with a detectably distinct fluorophore, and then hybridizing the fluorescently labeled nucleic acids to the same array.

In some embodiments an expression level reference sample is a population of nucleic acids (e.g., mRNAs, aRNAs, cDNAs, or aRNAs) derived from a cancer biopsy sample within which the sequences of at least four HDACiR-BGs are represented, and for which sensitivity to an HDACi compound has been determined. In some embodiments, the population of nucleic acids is derived from patient tumor cells cultivated in culture. In other embodiments, the population is derived directly from a biopsy without a cell culture step.

In some embodiments, the population of nucleic acids serving as an expression level reference sample is generated as follows. A cancer biopsy is obtained from a patient as described above, and afterwards viable tumors cells are then isolated and grown in culture as described in, e.g., Kern et al. (1990), *J. Natl. Cancer Inst.,* 82:582-588. In order to determine if cancer cells are sensitive to an HDACi compound, they are then grown in the presence of the HDACi compound at a range of concentrations, e.g., (0-10 μM), and cell proliferation is measured by any number of methods, e.g., tritiated thymidine incorporation. Inhibition of tumor cell proliferation by the HDACi compound is measured relative to tumor cell proliferation in the absence of the compound (i.e., no inhibition). Assignment of the cancer as sensitive or resistant is optionally determined based on a number of cell proliferation criteria. For example, if the $IC_{50}$ of the HDACi compound in the tested cancer cells is significantly lower (e.g., by 2 SDs) than that observed for cells known to be sensitive to the compound, the cancer is characterized as resistant. Thus, cells derived from the resistant cancer (e.g., directly or after passage in culture) are optionally used to generate a population of nucleic acids serving as an expression level (positive) reference sample used for setting HDACiR-BG expression level threshold values as described above. Conversely, tumor cells found to be sensitive to an HDACi compound are used generate a population of nucleic acids serving as an expression level (negative) reference sample.

Methods for obtaining RNA from biological samples (e.g., tissues or cells) including linear aRNA amplification from single cells include, e.g., Luzzi et al. (2005), *Methods Mol. Biol.,* 293:187-207. Further, diverse kits for high quality RNA purification are available commercially, e.g., from Qiagen (Valencia, Calif.), Invitrogen (Carlsbad, Calif.), Clontech (Palo Alto, Calif.), and Stratagene (La Jolla, Calif.).

In some embodiments, the expression level reference sample is an RNA sample isolated from one or more HDACi compound-resistant colon cancer cells. In one embodiment, the cells were derived from colon carcinoma biopsy R5247682266, R9866135153, R1078103114, or R4712781606 described herein.

HDACi Inhibitor Compounds

In another embodiment, HDACi inhibitor tumor compounds for which cancer resistance or sensitivity include, but are not limited to carboxylates, short-chain fatty acids, hydroxamic acids, electrophilic ketones, epoxides, cyclic peptides, and benzamides. In a further embodiment, HDACi inhibitor tumor compounds for which cancer resistance or sensitivity include, but are not limited to hydroxamic acids having the structure of Formula (A):

Formula (A)

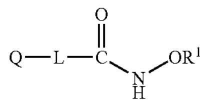

wherein

Q is an optionally substituted $C_{5-12}$ aryl or an optionally substituted $C_{5-12}$ heteroaryl;

L is a linker having at least 4 atoms;

$R^1$ is H or alkyl;

and a pharmaceutically acceptable salt, pharmaceutically acceptable N-oxide, pharmaceutically active metabolite, pharmaceutically acceptable prodrug, pharmaceutically acceptable solvate thereof.

HDACi inhibitor tumor compounds for which cancer resistance or sensitivity include, but are not limited to compounds having the structure of Formula (I):

Formula (I)

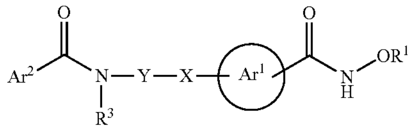

wherein:

$R^1$ is hydrogen or alkyl;

X is —O—, —$NR^2$—, or —$S(O)_n$ where n is 0-2 and $R^2$ is hydrogen or alkyl;

Y is alkylene optionally substituted with cycloalkyl, optionally substituted phenyl, alkylthio, alkylsulfinyl, alkysulfonyl, optionally substituted phenylalkylthio, optionally substituted phenylalkylsulfonyl, hydroxy, or optionally substituted phenoxy;

$Ar^1$ is phenylene or heteroarylene wherein said $Ar^1$ is optionally substituted with one or two groups independently selected from alkyl, halo, hydroxy, alkoxy, haloalkoxy, or haloalkyl;

$R^3$ is hydrogen, alkyl, hydroxyalkyl, or optionally substituted phenyl; and $Ar^2$ is aryl, aralkyl, aralkenyl, heteroaryl, heteroaralkyl, heteroaralkenyl, cycloalkyl, cycloalkylalkyl, heterocycloalkyl, or heterocycloalkylalkyl;

and individual stereoisomers, individual geometric isomers, or mixtures thereof; or a pharmaceutically acceptable salt thereof.

In another embodiment, HDACi inhibitor tumor compounds for which cancer resistance or sensitivity include, but are not limited to, PCI-24781.

In some embodiments, a patient is prescribed or administered an HDAC inhibitor to the patient based on a classification of the patient's cancer as being sensitive or resistant to an HDAC inhibitor according to the methods described herein.

In some embodiments, the methods described herein are used to optimize the selection of an anti-cancer agent for use in combination with an HDACi compound. In some embodiments, optimized selection of the second anti-cancer agent is performed by first comparing the set of known biomarker genes for resistance to the HDACi compound to sets of biomarker genes identified for other anti-cancer agents. The second anti-cancer agent is then selected for use in combination with the HDACi compound based on minimal overlap of the respective sets of resistance biomarker genes.

Examples of anti-cancer agents that are optionally used in combination with an HDACi compound include, but are not limited to, any of the following: gossyphol, genasense, polyphenol E, Chlorofusin, all trans-retinoic acid (ATRA), bryostatin, tumor necrosis factor-related apoptosis-inducing ligand (TRAIL), 5-aza-2'-deoxycytidine, all trans retinoic acid, doxorubicin, vincristine, etoposide, gemcitabine, imatinib (Gleevec®), geldanamycin, 17-N-Allylamino-17-Demethoxygeldanamycin (17-AAG), flavopiridol, LY294002, bortezomib, trastuzumab, BAY 11-7082, PKC412, or PD184352, Taxol™, also referred to as "paclitaxel", is an anti-cancer drug which acts by enhancing and stabilizing microtubule formation, and analogs of Taxol™, such as Taxotere™. Compounds that have the basic taxane skeleton as a common structure feature, have also been shown to have the ability to arrest cells in the G2-M phases due to stabilized microtubules and are optionally useful for treating cancer in combination with the compounds described herein.

Further examples of anti-cancer agents for use in combination with an HDACi compound include inhibitors of mitogen-activated protein kinase signaling, e.g., U0126, PD98059, PD184352, PD0325901, ARRY-142886, SB239063, SP600125, BAY 43-9006, wortmannin, or LY294002.

Other anti-cancer agents that are optionally employed in combination with an HDACi compound include Adriamycin, Dactinomycin, Bleomycin, Vinblastine, Cisplatin, acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cladribine; crisnatol mesylate; cyclophosphamide; cytarabine; dacarbazine; daunorubicin hydrochloride; decitabine; dexormaplatin; dezaguanine; dezaguanine mesylate; diaziquone; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine; gemcitabine hydrochloride; hydroxyurea; idarubicin hydrochloride; ifosfamide; iimofosine; interleukin II (including recombinant interleukin II, or rIL2), interferon alfa-2a; interferon alfa-2b; interferon alfa-n1; interferon alfa-n3; interferon beta-1a; interferon gamma-1 b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazoie; nogalamycin; ormaplatin; oxisuran; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride.

Other anti-cancer agents that are optionally employed in combination with an HDACi compound include: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B;

deslorelin; dexamethasone; dexifosfamide; dexrazoxane; dexverapamil; diaziquone; didemnin B; didox; diethylnorspermine; dihydro-5-azacytidine; 9-dioxamycin; diphenyl spiromustine; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylerie conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; R11 retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen-binding protein; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; and zinostatin stimalamer.

Yet other anticancer agents that are optionally employed in combination with an HDACi compound include alkylating agents, antimetabolites, natural products, or hormones, e.g., nitrogen mustards (e.g., mechloroethamine, cyclophosphamide, chlorambucil, etc.), alkyl sulfonates (e.g., busulfan), nitrosoureas (e.g., carmustine, lomusitne, ete.), or triazenes (decarbazine, etc.). Examples of antimetabolites include but are not limited to folic acid analog (e.g., methotrexate), or pyrimidine analogs (e.g., Cytarabine), purine analogs (e.g., mercaptopurine, thioguanine, pentostatin).

Examples of natural products useful in combination with an HDACi compound include but are not limited to vinca alkaloids (e.g., vinblastin, vincristine), epipodophyllotoxins (e.g., etoposide), antibiotics (e.g., daunorubicin, doxorubicin, bleomycin), enzymes (e.g., L-asparaginase), or biological response modifiers (e.g., interferon alpha).

Examples of alkylating agents that are optionally employed in combination an HDACi compound include, but are not limited to, nitrogen mustards (e.g., mechloroethamine, cyclophosphamide, chlorambucil, meiphalan, etc.), ethylenimine and methylmelamines (e.g., hexamethlymelamine, thiotepa), alkyl sulfonates (e.g., busulfan), nitrosoureas (e.g., carmustine, lomusitne, semustine, streptozocin, etc.), or triazenes (decarbazine, ete.). Examples of antimetabolites include, but are not limited to folic acid analog (e.g., methotrexate), or pyrimidine analogs (e.g., fluorouracil, floxouridine, Cytarabine), purine analogs (e.g., mercaptopurine, thioguanine, pentostatin.

Examples of hormones and antagonists useful in combination with an HDACi compound include, but are not limited to, adrenocorticosteroids (e.g., prednisone), progestins (e.g., hydroxyprogesterone caproate, megestrol acetate, medroxyprogesterone acetate), estrogens (e.g., diethlystilbestrol, ethinyl estradiol), antiestrogen (e.g., tamoxifen), androgens (e.g., testosterone propionate, fluoxymesterone), antiandrogen (e.g., flutamide), gonadotropin releasing hormone analog (e.g., leuprolide). Other agents that are optionally used in the methods and compositions described herein for the treatment or prevention of cancer include platinum coordination complexes (e.g., cisplatin, carboblatin), anthracenedione (e.g., mitoxantrone), substituted urea (e.g., hydroxyurea), methyl hydrazine derivative (e.g., procarbazine), adrenocortical suppressant (e.g., mitotane, aminoglutethimide).

Examples of anti-cancer agents which act by arresting cells in the G2-M phases due to stabilized microtubules and which are optionally used in combination with an HDACi compound include without limitation the following marketed drugs and drugs in development: Erbulozole (also known as R-55104), Dolastatin 10 (also known as DLS-10 and NSC-376128), Mivobulin isethionate (also known as CI-980), Vincristine, NSC-639829, Discodermolide (also known as NVP-XX-A-296), ABT-751 (Abbott, also known as E-7010), Altorhyrtins (such as Altorhyrtin A and Altorhyrtin C), Spongistatins (such as Spongistatin 1, Spongistatin 2, Spongistatin 3, Spongistatin 4, Spongistatin 5, Spongistatin 6, Spongistatin 7, Spongistatin 8, and Spongistatin 9), Cemadotin hydrochloride (also known as LU-103793 and NSC-D-669356), Epothilones (such as Epothilone A, Epothilone B, Epothilone C (also known as desoxyepothilone A or dEpoA), Epothilone D (also referred to as KOS-862, dEpoB, and desoxyepothilone B), Epothilone E, Epothilone F, Epothilone B N-oxide, Epothilone A N-oxide, 16-aza-epothilone B, 21-aminoepothilone B (also known as BMS-310705), 21-hydroxyepothilone D (also known as Desoxyepothilone F and dEpoF), 26-fluoroepothilone), Auristatin PE (also known as NSC-654663), Soblidotin (also known as TZT-1027), LS-4559-P (Pharmacia, also known as LS-4577), LS-4578 (Pharmacia, also known as LS-477-P), LS-4477 (Pharmacia), LS-4559 (Pharmacia), RPR-112378 (Aventis), Vincristine sulfate, DZ-3358 (Daiichi), FR-182877 (Fujisawa, also known as WS-9885B), GS-164 (Takeda), GS-198 (Takeda), KAR-2 (Hungarian Academy of Sciences), BSF-223651 (BASF, also known as ILX-651 and LU-223651), SAH-49960 (Lilly/Novartis), SDZ-268970 (Lilly/Novartis), AM-97 (Armad/Kyowa Hakko), AM-132 (Armad), AM-138 (Armad/Kyowa Hakko), IDN-5005 (Indena), Cryptophycin 52 (also known as LY-355703), AC-7739 (Ajinomoto, also known as AVE-8063A and CS-39.HCl), AC-7700 (Ajinomoto, also known as AVE-8062, AVE-8062A, CS-39-L-Ser.HCl, and RPR-258062A), Vitilevuamide, Tubulysin A, Canadensol, Centaureidin (also known as NSC-106969), T-138067 (Tularik, also known as T-67, TL-138067 and TI-138067), COBRA-1 (Parker Hughes Institute, also known as DDE-261 and WHI-261), H10 (Kansas State University), H16 (Kansas State University), Oncocidin A1 (also known as BTO-956 and DIME), DDE-313 (Parker Hughes Institute), Fijianolide B, Laulimalide, SPA-2 (Parker Hughes Institute), SPA-1 (Parker Hughes Institute, also known as SPIKET-P), 3-IAABU (Cytoskeleton/Mt. Sinai School of Medicine, also known as MF-569), Narcosine (also known as NSC-5366), Nascapine, D-24851 (Asta Medica), A-105972 (Abbott), Hemiasterlin, 3-BAABU (Cytoskeleton/Mt. Sinai School of Medicine, also known as MF-191), TMPN (Arizona State University), Vanadocene acetylacetonate, T-138026 (Tularik), Monsatrol, lnanocine (also known as NSC-698666), 3-1AABE (Cytoskeleton/Mt. Sinai School of Medicine), A-204197 (Abbott), T-607 (Tuiarik, also known as T-900607), RPR-115781 (Aventis), Eleutherobins (such as Desmethyleleutherobin, Desaetyleleutherobin, lsoeleutherobin A, and Z-Eleutherobin), Caribaeoside, Caribaeolin, Halichondrin B, D-64131 (Asta Medica), D-68144 (Asta Medica), Diazonamide A, A-293620 (Abbott), NPI-2350 (Nereus), Taccalonolide A, TUB-245 (Aventis), A-259754 (Abbott), Diozostatin, (−)-Phenylahistin (also known as NSCL-96F037), D-68838 (Asta Medica), D-68836 (Asta Medica), Myoseverin B, D-43411 (Zentaris, also known as D-81862), A-289099 (Abbott), A-318315 (Abbott), HTI-286 (also known as SPA-110, trifluoroacetate salt) (Wyeth), D-82317 (Zentaris), D-82318 (Zentaris), SC-12983 (NCl), Resverastatin phosphate sodium, BPR-OY-007 (National Health Research Institutes), and SSR-250411 (Sanofi).

Applications of HDACiR-BGs

The methods and compositions described herein are optionally used to increase the likelihood of a therapeutically effective treatment of a patient's cancer with an HDACi compound by providing an indication (e.g. by oral or written communication in any analog or digital medium) of which genes are HDACiR-BGs, as well as HDACiR-BG expression level reference values (e.g., expression level threshold values) above which HDACi compound resistance is likely (i.e., greater than the probability by chance) or below which HDACi compound sensitivity is likely.

In some embodiments, the indication includes a document with an interpretation of expression levels of at least four biomarker genes selected from Table 1 as to the likelihood that a patient's cancer is resistant or sensitive to treatment with an HDACi compound.

In some embodiments, the document includes an interpretation of the expression levels of at least one HDACiR-BG selected from DEFA6, ITGB4, TM4SF4, SYK, PPAP2C, RAB25, HEPH, NOXO1, TM4SF4, PTPN3, EPHA2, FGFBP1, ABCC3, TPMT, IL18, and DPEP1.

In some embodiments an indication is provided in one or more databases containing information concerning one or more HDACiR-BGs, including one or more expression level threshold values that permit the interpretation of the effect of HDACiR-BG expression levels on the resistance or sensitivity of a cancer to an HDACi compound according to any of the methods described herein. Such expression level threshold values include those set based on, e.g., deviation of HDACiR-BG expression levels in a test sample from the corresponding HDACiR-BG expression levels in an expression level (positive or negative) reference sample as described herein. Alternatively, or in addition, expression level threshold values are optionally set based on deviation of the expression ratios of HDACiR-BGs to one or more internal expression control genes (e.g., RNA polymerase II, HDAC3, or ZNF217). For example, as described herein, the mean expression ratio (based on TaqMan fluorescence intensity) of the HDACiR-BG DEFA6 to the internal expression control gene ZNF217 is 5.83 in HDACi-resistant colon cancer cells and 0.24 in HDACi-sensitive colon cancer cells.

In some embodiments, the databases include HDACiR-BG expression level profiles or thresholds associated with resistance to one or more HDACi compounds for one or more types of cancer.

Other information that is optionally included in the databases or in other types of indication include, but are not limited to, HDACiR-BG sequence information, frequency distributions of HDACiR-BG expression levels in a particular cancer population, descriptive information concerning the clinical status of a biological sample analyzed for HDACiR-BG expression profiles, or the clinical status of the patient from which the sample was derived. The database is optionally be designed to include different parts, for instance an HDACiR-BG list database, and an informative HDACiR-BG expression profile database, e.g., a database associating with each HDACiR-BG expression profile record the probability that the expression profile is associated with resistance to an HDACi compound. Methods for the configuration and construction of databases are widely available, for instance, see U.S. Pat. No. 5,953,727.

The databases described herein are optionally linked to an outside or external database. In some embodiments, the database optionally communicates with outside data sources, such as database of the developmental therapeutics program of the national cancer institute or the National Center for Biotechnology Information through the Internet.

Any appropriate computer platform is used to perform the methods for interpreting one or more HDACiR-BG expression profiles by the methods described herein. In some embodiments, the computer platform receive direct input from a database, e.g., one of the databases described herein. For example, a large number of computer workstations are available from a variety of manufacturers, such has those available from Silicon Graphics. Client-server environments, database servers and networks are also widely available and are appropriate platforms for the databases described herein.

The databases described herein are optionally used to present information identifying a set of HDACiR-BG expression profiles in an individual and such a presentation is optionally used to predict or diagnose the likelihood of a effective therapeutic treatment of the individual's cancer with a particular HDACi compound based on a statistical comparison of the individual's expression profile to HDACiR-BG expression level thresholds as described herein. Accordingly, one chooses to partition cancer patients into subgroups at any threshold value of the measured HDACiR-BG expression, where all patients with expression values above the threshold have higher risk, and all patients with expression values below the threshold have lower risk, of and HDACi compound-resistant cancer resistance or vice versa, depending on whether the expression level threshold is based on an expression level in a cancer determined to be resistant to an HDACi compound treatment (i.e., a positive reference sample) or sensitive to the HDACi compound treatment (i.e., a negative reference sample). Alternatively, HDACiR-BG expression profiles ranked on a probability continuum, where the more an HDACiR-BG expression level deviates negatively from (i.e., is less than) an expression level positive reference value, the higher the probability that the cancer is sensitive to treatment with an HDACi compound. Conversely, the more an HDACiR-BG expression level deviates positively from (i.e., is greater than) an expression level negative reference value, the higher the probability that the cancer is resistant to treatment with an HDACi compound.

EXAMPLES

The following specific examples are to be construed as merely illustrative, and not limitative of the remainder of the disclosure in any way whatsoever. Without further elaboration, it is believed that one skilled in the art can, based on the description herein, utilize the present invention to its fullest extent.

Example 1 mRNA Expression Profiling of HDACi Sensitive Versus Resistant Colorectal Tumor Cells Ex Vivo We and others previously developed several pharmacodynamic markers for HDACi compounds (such as tubulin or histone acetylation, p21 expression etc). However, there is currently no clinically predictive biomarker for response to these agents available. In this work, we developed a strategy to identify such biomarkers for the HDACi compound PCI-24781 in primary human colorectal tumors.

The method used soft agar chemosensitivity assays in which primary human tumors were exposed in culture to PCI-24781. Either a trititated thymidine or alamar blue assay was then used to estimate the percentage of resistance to PCI-24781. For example in the trititated thymidine assay, sensitive tumor cells affected by the drug divided less and therefore incorporated less thymidine, whereas resistant tumor cells continued to grow and divide and therefore incorporated more thymidine into their DNA. It has been shown historically that under the optimized conditions of this assay, a patient whose tumor is classified as resistant to a given drug has <1% probability of response to that drug in the clinic (in published correlations to clinical outcome, these assays predicted resistance with an accuracy of 99% in solid cancers and 92% in blood cancers). For example, a recent paper correlated in vitro sensitivity or resistance to fludarabine in the DISC assay in B-cell CLL patients with clinical outcome (median survival 7.9 months in resistant vs 41.7 months in sensitive patients). Similar data has also been published for solid tumors: e.g., for sensitivity or resistance to Pt in ovarian tumors, and to CPX and DOX in breast tumors.

After determining ex vivo sensitivity or resistance to PCI-24781 for each tumor, RNA isolated from tumor cells was then profiled on microarrays and a marker set was identified by statistical analysis of the data. This marker set was validated by RT-PCR (TaqMan™) analysis. Such pharmacogenomic biomarkers that are used for patient stratification in the clinic provide a competitive advantage in the development of PCI-24781. A graphic summary of the method and its clinical applications is illustrated in FIG. 1.

We examined the ex-vivo response of primary colorectal tumors from various patients to an HDAC inhibitor, PCI-24781, and subsequently determined whether there were robust differences in the mRNA expression profiles of sensitive versus resistant tumor cells prior to HDACi treatment.

Figure 2:
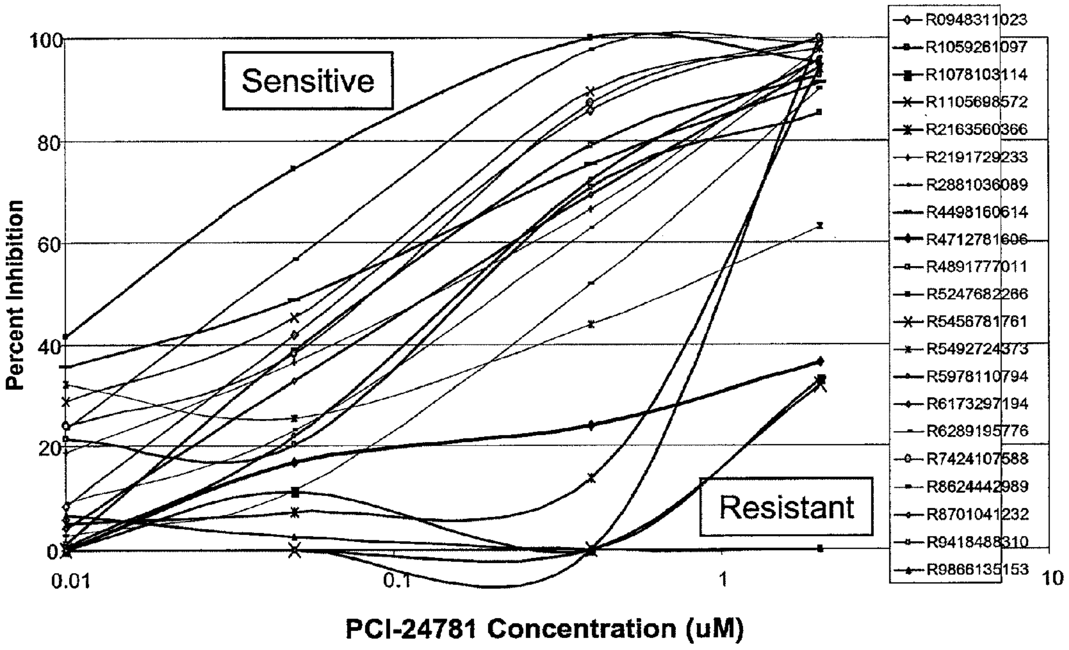
FIG. 2 is an illustrative graph showing in vitro inhibition of cell proliferation versus concentration of the HDACi compound PCI-24781 for a series of colon carcinoma cell lines.

Primary colorectal cancer (CRC) samples were obtained from patient biopsies (Table 2). Viable tumor cells were plated and cultured in soft agar as described in Kern et al. (1990), *J. Natl. Cancer Inst.,* 82:582-588, and were treated with a range of PCI-24781 concentrations (0.01-2 μM). Tritiated thymidine was added to the culture after 3 days of exposure to the drug, and the amount of radioactivity incorporated into the cells after a further 2 days was quantified. The percentage of cell growth inhibition (% G1) was calculated by comparing the treated cells to the control cells, and from these growth profiles the tumors were classified as either sensitive or resistant based on deviation from the median profile. As shown in FIG. 2, primary tumors displayed a spectrum of growth inhibition phenotypes from 100% to 0% relative to control at the PCI-24781 concentrations tested (up to 2 μM).

TABLE 2

Clinical data for colorectal cancer biopsies

| Research ID | Cancer Name | Age | Sex | Site | Clinical Diagnosis | Histology | Specimen Type |
|---|---|---|---|---|---|---|---|
| R1078103114 | Colon Carcinoma | 54 | F | R Ovary | Colon Carcinoma | ADENOCARCINOMA | Solid Tumor Biopsy |
| R1105698572 | Colon Carcinoma | 72 | F | Portion of Terminal Ileum | Colon Carcinoma | NA | Solid Tumor Biopsy |

TABLE 2-continued

Clinical data for colorectal cancer biopsies

| Research ID | Cancer Name | Age | Sex | Site | Clinical Diagnosis | Histology | Specimen Type |
|---|---|---|---|---|---|---|---|
| R2163560366 | Colon Carcinoma | 58 | F | Uterus | Rectal Cancer | NA | Solid Tumor Biopsy |
| R4712781606 | Colon Carcinoma | 59 | M | Colon Resection | Colon Carcinoma | NA | Solid Tumor Biopsy |
| R5247682266 | Colon Carcinoma | 51 | F | Upper Lobe Lung | Colon Carcinoma | ADENOCARCINOMA | Solid Tumor Biopsy |
| R5891015174 | Colon Carcinoma | 43 | F | Colon | Cecal Carcinoma | NA | Solid Tumor Biopsy |
| R6173297194 | Colon Carcinoma | 65 | M | Omentum | Colon Carcinoma | ADENOCARCINOMA | Solid Tumor Biopsy |
| R7103644976 | Colon Carcinoma | 52 | F | R Tube & Ovary | Colon Cancer | NA | Solid Tumor Biopsy |
| R9866135153 | Colon Carcinoma | 55 | F | R Hepatic Lobe | Colon Carcinoma | ADENOCARCINOMA | Solid Tumor Biopsy |
| R2881036089 | Colon Carcinoma | 79 | F | Colon | Colon Carcinoma | CARCINOMA, PD | Solid Tumor Biopsy |
| R5492724373 | Colon Carcinoma | 55 | F | Cecum | Colon Carcinoma | COLON CARCINOMA | Solid Tumor Biopsy |
| R8624442989 | Colon Carcinoma | 47 | F | Brain | Colon Carcinoma | NA | Solid Tumor Biopsy |
| R0948311023 | Colon Carcinoma | 33 | F | L Lower Lung Lobe Nodule | Colon Carcinoma | ADENOCARCINOMA | Solid Tumor Biopsy |
| R1059261097 | Colon Carcinoma | 50 | M | Liver | Colon Cancer | ADENOCARCINOMA | Solid Tumor Biopsy |
| R2191729233 | Colon Carcinoma | 62 | F | Ovary | Colon Cancer | ADENOCARCINOMA | Solid Tumor Biopsy |
| R4498160614 | Colon Carcinoma | 40 | F | L Ovary | Colon Carcinoma | ADENOCARCINOMA | Solid Tumor Biopsy |
| R4891777011 | Colon Carcinoma | 53 | F | R Abdominal Sidewall | Colon Carcinoma | ADENOCARCINOMA | Solid Tumor Biopsy |
| R5456781761 | Colon Carcinoma | 65 | F | Liver Lobes 5&6 | Met. Colon CA to L | NA | Solid Tumor Biopsy |
| R5978110794 | Colon Carcinoma | 63 | F | Sigmoid Rectum | Colon Carcinoma | NA | Solid Tumor Biopsy |
| R6289195776 | Colon Carcinoma | 56 | M | Liver | Colon Carcinoma | ADENOCARCINOMA | Solid Tumor Biopsy |
| R6324805249 | Colon Carcinoma | 55 | F | Ovary | Colon Carcinoma | ADENOCARCINOMA | Solid Tumor Biopsy |
| R7424107588 | Colon Carcinoma | 48 | M | Lumbar/Spine Biopsy | Colon Carcinoma | NA | Solid Tumor Biopsy |
| R8701041232 | Colon Carcinoma | 65 | M | Sigmoid Colon | Colon Carcinoma | ADENOCARCINOMA | Solid Tumor Biopsy |
| R9418488310 | Colon Carcinoma | 55 | F | Cecum | Colon Carcinoma | ADENOCARCINOMA | Solid Tumor Biopsy |

resistant and sensitive tumors that were treated with PCI-24781 (2 μM) or untreated. Total RNA was isolated using Qiagen procedures (Qiagen, Inc., Valencia, Calif.) and fluorescent probes were prepared and hybridized to Codelink Human Whole Genome oligonucleotide microarrays containing ~55,000 unique probes (GE Healthcare Bio-Sciences Corp., Piscataway, N.J.) according to the manufacturer's instructions. The microarrays were scanned in a GenePix 4000B scanner (Molecular Devices Corporation, Sunnyvale Calif.). The images were processed with Codelink software and the exported data was analyzed as follows.

The median-normalized microarray data were imported into Genespring software (Agilent), and principal component analysis (PCA) and hierarchical clustering analysis were performed. We looked for consistent results from multiple analysis methods to provide additional confidence in our results. For multiple hypothesis correction, we used the q-values approach for false discovery rates (FDR) as described in Storey et al. (2003), *Proc. Nat. Acad. Sci. USA,* 100:9440-9445. As a second analytical approach we adopted the Bayesian ANOVA approach described in Ishwaran et al. (2003), *J. Amer. Stat. Assoc.,* 98:438-455.

Figure 3:
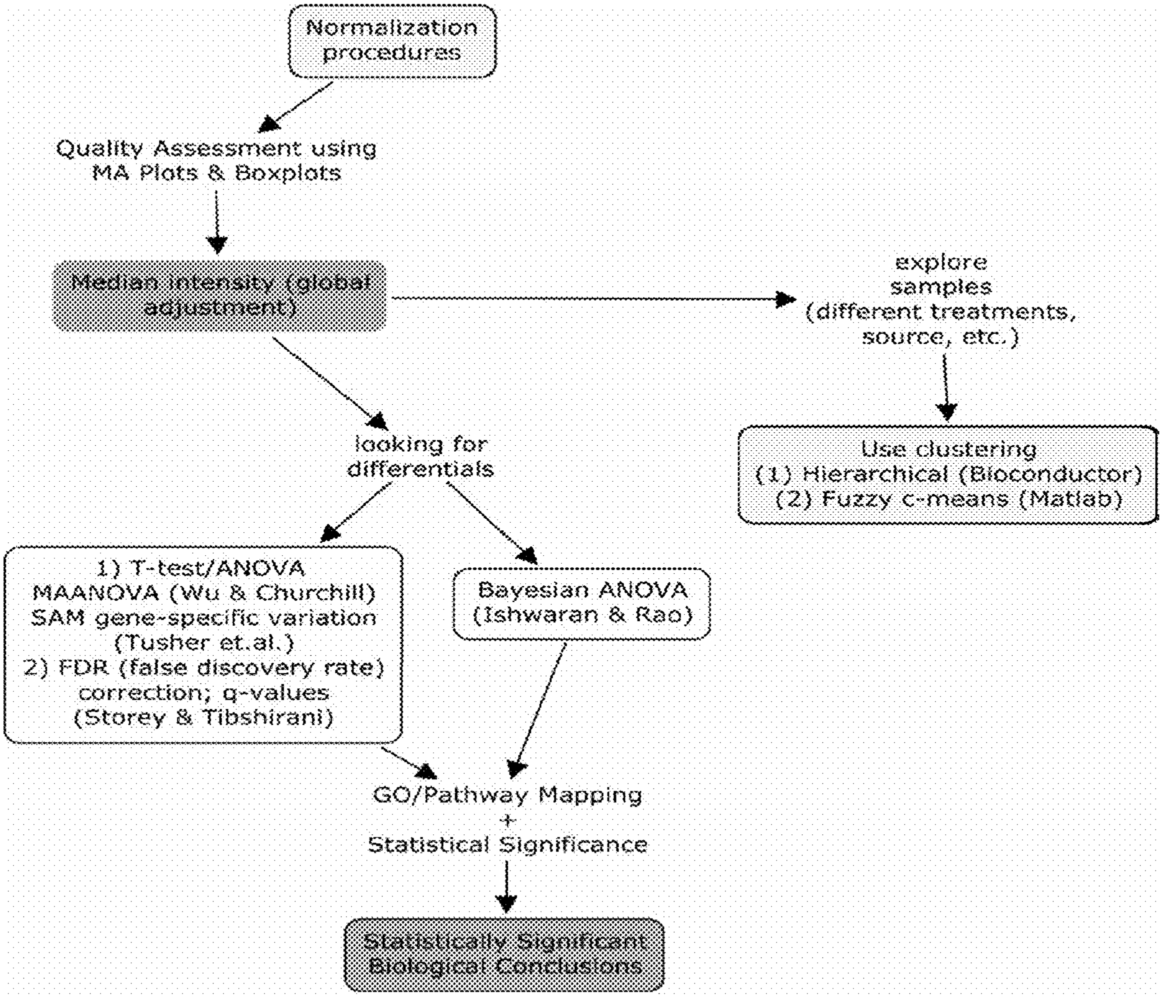
FIG. 3 is an illustrative flow diagram illustrating the statistical approach used to analyze microarray data to identify differentially expressed genes in populations of cancer cells resistant to a HDACi compound versus cancer cells that are sensitive to the compound.

In the Bayesian ANOVA method, the contribution of irrelevant genes to the ANOVA model are selectively shrunk to balance total false detections against total false non-detections. The output is a Zcut score which identifies genes whose contribution to the ANOVA model is larger than the standard z-score. See Ishwaran et al., ibid., and the website at bamarray.com. For the identification of biomarkers predictive of PCI-24781 resistance, we used only the untreated control samples divided into pools based on the sensitivity or resistance classification in the assay described above. This analytical approach is summarized in FIG. 3.

Figure 4:
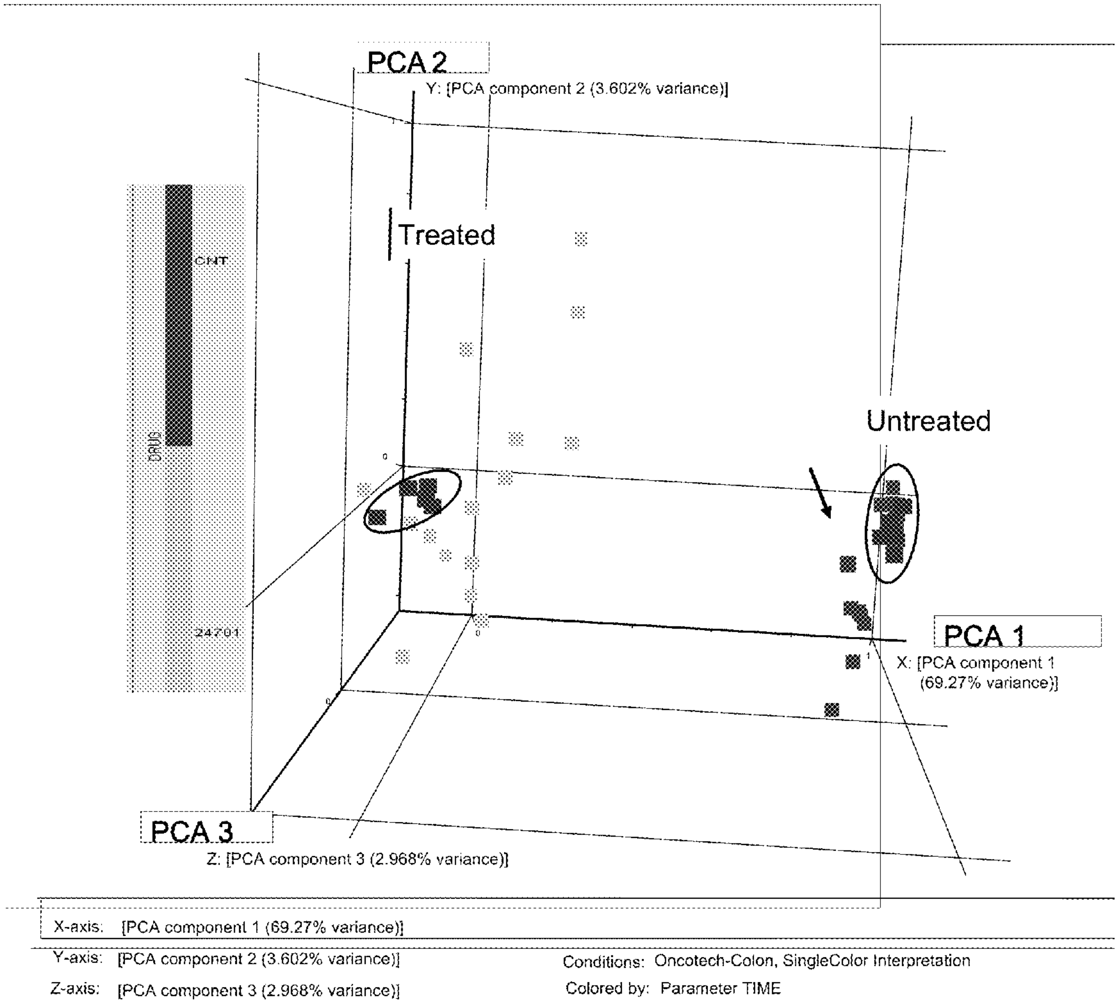
FIG. 4 is an illustrative scatter plot illustrating principal component analysis of gene expression microarray data in HDACi compound-treated and untreated cancer cells, and sensitive and resistant cancer cells.
Figure 5:
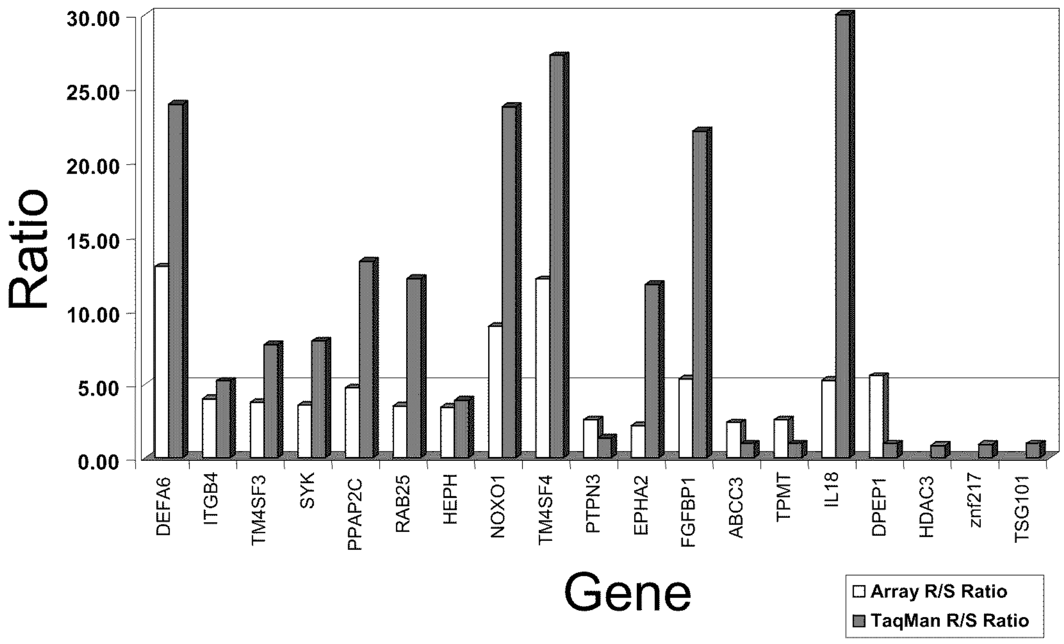
FIG. 5 is an illustrative bar graph comparing the results of a microarray method versus TaqMan® quantitative RT-PCR method for determining the ratio of mRNA expression levels for a series of identified HDACi compound resistance biomarker genes in PCI-24781-resistant versus PCI-24781 colon carcinoma cells.
Figure 6:
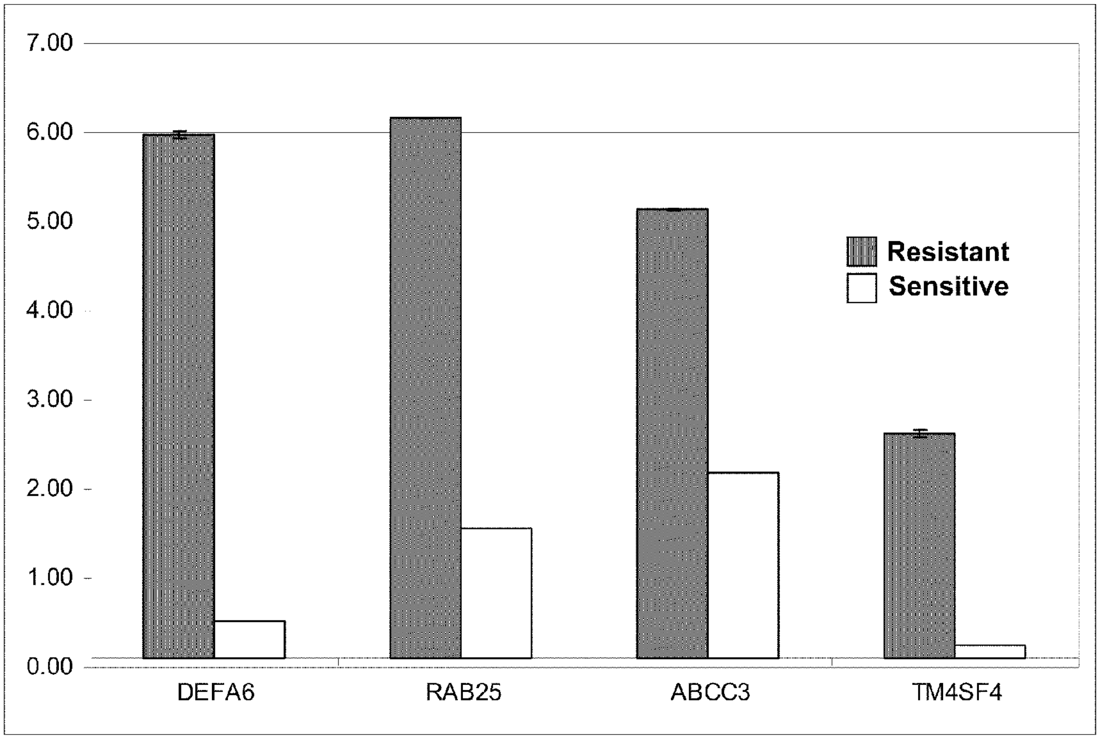
FIG. 6 is an illustrative bar graph comparing relative expression levels of four HDACi compound resistance biomarker genes in cancer cells that are resistant to the HDAC inhibitor compound (PCI-24781) versus expression of the biomarker genes in cancer cells that are sensitive to the compound.

As shown in FIG. 4, principal components analysis clearly distinguished untreated cell expression profiles from treated cell expression profiles. Controls (arrowhead) are more similar to each other and well separated from the treated samples. The major component PCA1 clearly resolves treated from control samples. Interestingly, the resistant cell expression profiles (circled in both the treated and untreated samples) clustered together before and after treatment, whereas the sensitive samples varied widely in their profiles after treatment with PCI-24781. This suggested that it is easier to identify patients with the most resistant tumors and exclude them from a clinical trial rather than to identifying patients with sensitive tumors.

Based on the microarray analysis, we identified a total of 44 genes (see table 3) whose level of expression was significantly higher (z-score greater than 3.5) in PCI-24781 resistant cells than in PCI-24781 sensitive cells (data not shown). Of note, the expression of the identified biomarker genes was not altered by treatment with PCI-24781.

TABLE 3

Microarray Analysis: Upregulated Genes in PCI-24781-resistant Colorectal Tumor Cells

| Gene Name | Gene Symbol | GenBank Accession # | z-score | Res./Sens. Fold Expression Difference |
|---|---|---|---|---|
| PTPN3 | PTPN3 | AK096975 | 14.19 | 2.58 |
| ATP-binding cassette, sub-family C (CFTR/MRP), member 3 | ABCC3 | NM_020037 | 13.24 | 2.37 |
| specifically androgen-regulated protein | SARG | NM_023938 | 13.04 | 4.00 |

TABLE 3-continued

Microarray Analysis: Upregulated Genes in PCI-24781-resistant Colorectal Tumor Cells

| Gene Name | Gene Symbol | GenBank Accession # | z-score | Res./Sens. Fold Expression Difference |
|---|---|---|---|---|
| phosphatidic acid phosphatase type 2C | PPAP2C | NM_177526 | 12.95 | 4.75 |
| neural proliferation, differentiation and control, 1 | NPDC1 | NM_015392 | 11.88 | 2.45 |
| C-terminal tensin-like | CTEN | NM_032865 | 11.32 | 3.83 |
| RAB25, member RAS oncogene family | RAB25 | NM_020387 | 10.96 | 3.51 |
| hephaestin | HEPH | NM_138737 | 10.49 | 3.38 |
| Thiopurine S-methyltransferase | TPMT | NM_000367 | 9.97 | 2.56 |
| plakophilin 3 | PKP3 | NM_007183 | 9.31 | 3.13 |
| UDP-N-acetyl-alpha-D-galactosamine: polypeptide N-acetylgalactosaminyltransferase 5 (GalNAc-T5) | GALNT5 | NM_014568 | 9.31 | 2.54 |
| calmodulin-like 4 | CALML4 | NM_033429 | 9.14 | 3.51 |
| UDP-N-acetyl-alpha-D-galactosamine: polypeptide N-acetylgalactosaminyltransferase 12 (GalNAc-T12) | GALNT12 | AK024865 | 8.86 | 2.51 |
| thiamin pyrophosphokinase 1 | TPK1 | NM_022445 | 8.81 | 3.55 |
| defensin, alpha 6, Paneth cell-specific | DEFA6 | NM_001926 | 8.58 | 12.92 |
| epithelial protein lost in neoplasm beta | EPLIN | NM_016357 | 8.49 | 2.33 |
| chloride intracellular channel 5 | CLIC5 | NM_016929 | 7.20 | 3.60 |
| PERP, TP53 apoptosis effector | PERP | NM_022121 | 6.94 | 2.60 |
| spleen tyrosine kinase | SYK | NM_003177 | 6.90 | 3.59 |
| solute carrier family 12 (sodium/potassium/chloride transporters), member 2 | SLC12A2 | NM_001046 | 6.75 | 4.85 |
| guanylate cyclase 2C (heat stable enterotoxin receptor) | GUCY2C | NM_004963 | 6.72 | 3.53 |
| transmembrane 4 superfamily member 4 | TM4SF4 | NM_004617 | 6.54 | 12.09 |
| transforming growth factor, alpha | TGFA | NM_003236 | 6.44 | 3.11 |
| fibroblast growth factor binding protein 1 | FGFBP1 | NM_005130 | 6.27 | 5.35 |
| PTK6 protein tyrosine kinase 6 | PTK6 | NM_005975 | 6.24 | 3.10 |
| epithelial V-like antigen 1 | EVA1 | NM_005797 | 5.96 | 4.55 |
| EPH receptor A2 | EPHA2 | NM_004431 | 5.90 | 2.18 |
| integrin, alpha 6 | ITGA6 | NM_000210 | 5.53 | 4.09 |
| tumor necrosis factor receptor superfamily, member 21 | TNFRSF21 | NM_014452 | 5.47 | 2.16 |
| transmembrane 4 superfamily member 3 | TM4SF3 | NM_004616 | 5.32 | 3.75 |
| interleukin 18 (interferon-gamma-inducing factor) | IL18 | NM_001562 | 5.24 | 5.22 |
| bone morphogenetic protein 4 | BMP4 | NM_130850 | 4.82 | 3.91 |
| sphingomyelin phosphodiesterase, acid-like 3B | SMPDL3B | NM_014474 | 4.62 | 5.49 |
| transmembrane protease, serine 2 | TMPRSS2 | NM_005656 | 4.62 | 3.51 |
| guanine deaminase | GDA | NM_004293 | 4.56 | 6.52 |
| macrophage stimulating 1 receptor (c-met-related tyrosine kinase) | MST1R | NM_002447 | 4.49 | 4.52 |
| integrin, beta 4 | ITGB4 | NM_000213 | 4.41 | 3.98 |
| annexin A3 | ANXA3 | NM_005139 | 4.11 | 3.34 |
| chemokine (C-C motif) ligand 15 | CCL15 | NM_032965 | 3.87 | 3.74 |
| dipeptidase 1 (renal) | DPEP1 | NM_004413 | 3.72 | 5.53 |
| NADPH oxidase organizer 1 | NOXO1 | NM_172167 | 3.71 | 8.92 |
| interferon, alpha-inducible protein 27 | IFI27 | NM_005532 | 3.69 | 3.65 |
| cytochrome P450, family 3, subfamily A, polypeptide 43 | CYP3A43 | NM_057095 | 3.65 | 3.40 |
| plakophilin 2 | PKP2 | NM_004572 | 3.54 | 3.45 |

Analysis of the biological pathways associated with these genes showed that homologous recombination, nucleotide excision repair, cell cycle, and apoptosis were among those that affect sensitivity to PCI-24781.

In order to validate the higher expression of each resistance biomarker gene identified by microarray analysis, we analyzed the expression of each biomarker gene by the TaqMan® quantitative RT-PCR method as described below.

TaqMan® Gene Expression Assays for selected genes were obtained from Applied Biosystems (Foster City, Calif.). One-step RT-PCR was carried out in triplicate on 25 ng of total RNA from each sample on an ABI PRISM® 7900HT sequence detection system. The mRNA levels for each gene were normalized to the amount of RNA in the well as measured in parallel using Ribogreen (Invitrogen, Inc., Carlsbad, Calif.). We then calculated the ratios of expression levels of the biomarker genes in the resistant & sensitive samples (R/S) and compared them to the corresponding ratios obtained from the microarray analysis. The comparative analysis for 16 of the biomarker genes listed in Table 3 is shown in Table 4. As a further validation of our microarray analysis, we performed TaqMan assays for three genes whose expression, as measured by microarray hybridization, was not found to correlate with PCI-24781 resistance (see last three genes in Table 3).

TM4SF4. Further, a number of the identified genes encode secreted proteins or transmembrane proteins that shed their extracellular domains. Genes encoding secretable proteins include, e.g., DEFA6 (NM_001926), TM4SF4 (NM_004617), TGFA (NM_003236), FGFBP1 (NM_005130), EPHA2 (NM_004431), TNFRSF21 (NM_014452), TMF4SF3 (NM_004616), IL18 (NM_001562), TMPRSS2 (NM_005656), and CCL15 (NM_032965).

Based on these data, we concluded that the expression pattern of subsets (e.g., four or more) of the identified biomarker genes provide "resistance signatures" that are optionally used to reliably identify colorectal tumors that are resistant or susceptible to the HDAC inhibitor PCI-24781.

Figure 11:
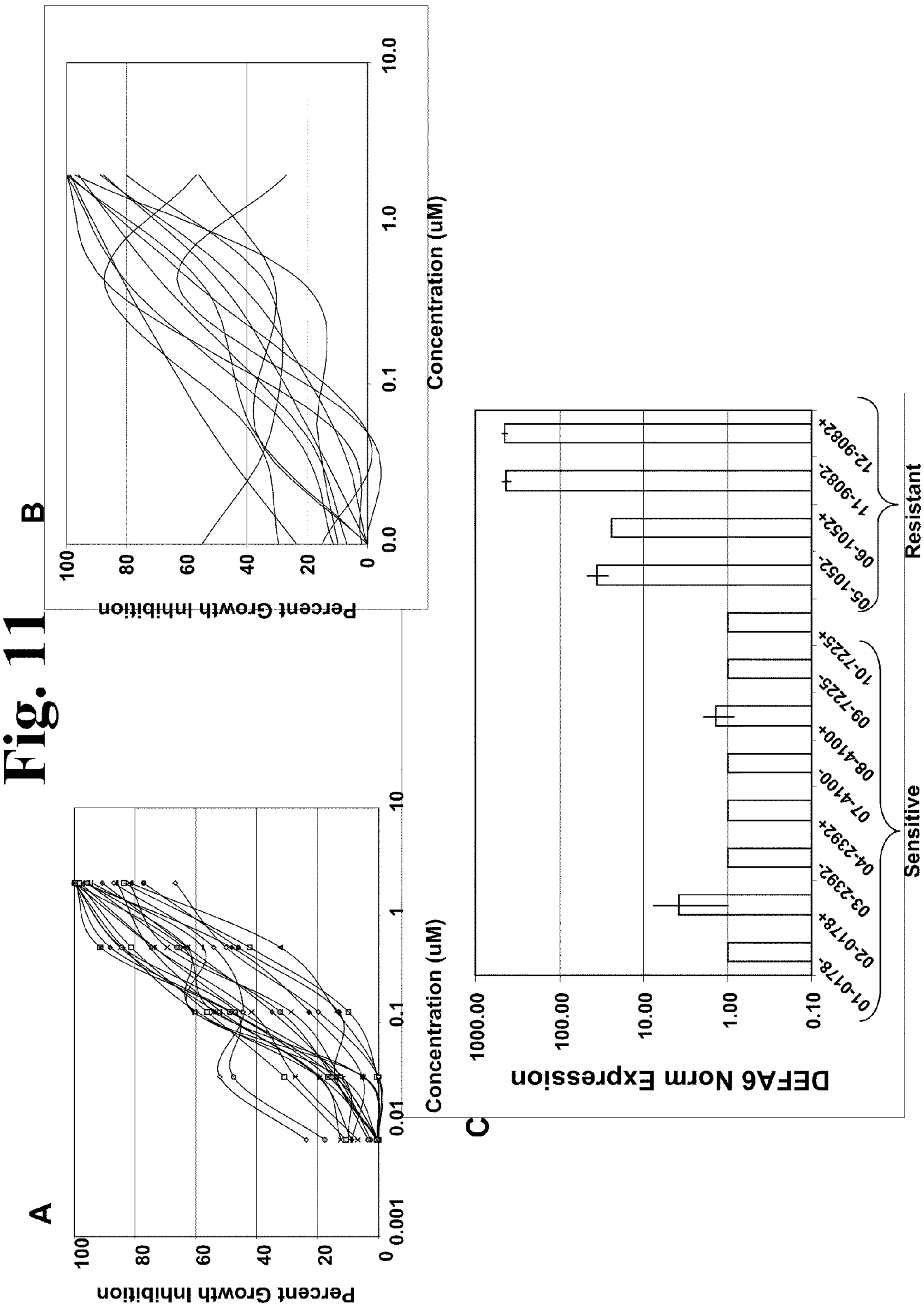

In a validation experiment, we found that ex vivo cultured primary colon tumor cells from twelve newly diagnosed, naive patients were all sensitive to growth inhibition by the HDAC inhibitor PCI-24781 (FIG. 11A). In contrast, we found that in a number of cases, advanced metastatic colon tumor cells were resistant to growth inhibition by the HDAC inhibitor PCI-24781 (FIG. 11B), and the DEFA6 mRNA expression levels were higher in HDAC-resistant cells than in HDAC-sensitive cells (FIG. 11C).

TABLE 4

Microarray vs TaqMan Analysis of Genes Upregulated in PCI-24781-Resistant vs Sensitive Colorectal Tumor Cells

| | | Microarrays | | | | Taqman | | | | |
|---|---|---|---|---|---|---|---|---|---|---|
| GeneName | GeneCards | Zcut | Resist mean | Sens mean | Ratio ArR/S | Sens Ct | ResistAvg | SensAvg | Ratio TaqR/S | Taq/Arr |
| defensin, alpha 6, Paneth cell-specific | DEFA6 | 8.58 | 8.57 | 0.65 | 12.92 | 37.20 | 1.34 | 0.06 | 23.94 | 1.85 |
| integrin, beta 4 | ITGB4 | 4.41 | 0.67 | 0.17 | 3.98 | 28.99 | 86.18 | 16.59 | 5.20 | 1.31 |
| transmembrane 4 superfamily member 3 | TM4SF3 | 5.32 | 239.99 | 65.01 | 3.75 | 29.21 | 108.96 | 14.30 | 7.62 | 2.03 |
| spleen tyrosine kinase | SYK | 6.90 | 5.16 | 1.48 | 3.59 | 35.45 | 1.50 | 0.19 | 7.90 | 2.20 |
| phosphatidic acid phosphatase type 2C | PPAP2C | 12.95 | 5.35 | 1.14 | 4.75 | 36.45 | 1.26 | 0.09 | 13.31 | 2.80 |
| RAB25, member RAS oncogene family | RAB25 | 10.96 | 55.31 | 15.92 | 3.51 | 32.56 | 16.97 | 1.40 | 12.10 | 3.45 |
| hephaestin | HEPH | 10.49 | 8.11 | 2.46 | 3.38 | 32.90 | 4.34 | 1.11 | 3.93 | 1.16 |
| NADPH oxidase organizer 1 | NOXO1 | 3.71 | 0.98 | 0.11 | 8.92 | 35.41 | 4.60 | 0.19 | 23.76 | 2.66 |
| transmembrane 4 superfamily member 4 | TM4SF4 | 6.54 | 2.06 | 0.18 | 12.09 | 40.00 | 0.22 | 0.01 | 27.22 | 2.25 |
| PTPN3 | PTPN3 | 14.19 | 5.45 | 2.16 | 2.58 | 30.71 | 6.60 | 5.04 | 1.31 | 0.51 |
| EPH receptor A2 | EPHA2 | 5.90 | 29.27 | 13.49 | 2.18 | 31.91 | 25.80 | 2.20 | 11.73 | 5.37 |
| fibroblast growth factor binding protein 1 | FGFBP1 | 6.27 | 27.93 | 5.30 | 5.35 | 37.76 | 0.84 | 0.04 | 22.08 | 4.13 |
| ATP-binding cassette, sub-family C, member 3 | ABCC3 | 13.24 | 4.14 | 1.82 | 2.37 | 40.00 | 0.01 | 0.01 | 0.96 | 0.41 |
| thiopurine S-methyltransferase | TPMT | 9.97 | 26.21 | 10.11 | 2.56 | 40.00 | 0.01 | 0.01 | 0.96 | 0.38 |
| interleukin 18 (interferon-gamma-inducing factor) | IL18 | 5.24 | 26.57 | 5.04 | 5.22 | 40.00 | 0.62 | 0.01 | 77.06 | 14.77 |
| dipeptidase 1 (renal) | DPEP1 | 3.72 | 2.93 | 0.54 | 5.53 | 40.00 | 0.01 | 0.01 | 0.96 | 0.17 |
| HDAC3 | HDAC3 | | Not significant | | | 25.66 | 141.70 | 167.11 | 0.85 | |
| Zinc Finger Protein znt217 | ZNF217 | | Not significant | | | 35.07 | 0.23 | 0.25 | 0.93 | |
| TSG101 | TSG101 | | Not significant | | | 40.00 | 0.01 | 0.01 | 0.96 | |

The comparison of microarray versus results is graphically summarized in FIG. 2. As shown in Table 4 and FIG. 2, genes found to be significantly upregulated by the microarray method were also found to be upregulated by the TaqMan method, though the latter generally yielded higher R/S ratios. Likewise, three genes whose expression did not differ significantly in the microarray analysis also showed no significant difference in the TaqMan assay.

Interestingly, several of the identified biomarker genes have previously been studied in relation to cancer, e.g., DEFA6, RAB25 small GTPase, MRP3 (ABCC3), and

Example 2

Identification and Cross-Validation of Functional Biomarkers for HDAC Inhibitor Compounds and Selection of Clinical Indications In order to determine relevant tumor types and to identify pharmacodynamic (PD) markers that are useful in the clinic, we first identified biomarkers of HDAC inhibition in mice and used these to identify HDACi-"sensitive" tissues. This was done by identifying, in HDACi-treated mice, genes in peripheral blood mononuclear cells (PBMC) whose mRNA levels showed the same timecourse as acetylated tubulin levels, an index of HDAC inhibition. These biomarker genes were then used to identify HDACi responsive mouse tissues. Primary human tumors corresponding to sensitive tissues were then tested ex-vivo with PCI-24781, and it was found that tumors from tissues that showed higher levels of activity were sensitive to inhibition by PCI-24781, thus validating that this technique does indeed predict sensitive tumor types.

In brief, female BALB/c mice were injected IV with 50 mg/kg PCI-24781 or vehicle. Blood and various tissues were collected at 0.25, 0.5, 1, 2, 3 & 8 hours after dosing. For acetylated histone and tubulin detection, organs/tissues were pooled for each vehicle and drug-treated organ group. RNA and protein were extracted from the samples with the PARIS Protein and RNA Isolation System (Ambion). Levels of acetylated and total α-tubulin & histones were evaluated by immunoblotting.

RNA expression profiles were determined using on a GE-Codelink Mouse Uniset1 10K oligonucleotide arrays in duplicate. Each treated sample was normalized to the corresponding vehicle control. In order to validate the expression profile of HDADi-responsive genes identified by the gene expression array assays, Taqman gene expression assays were performed using Applied Biosystems Inc. assays. One-step RT-PCR was carried out in triplicate on 25 ng of total RNA from each sample on a ABI PRISM 7700 instrument. The mRNA levels for each gene were normalized to the amount of RNA in the well as measured in parallel using Ribogreen (Molecular Probes). The treated samples were then normalized to the vehicle control at that time point.

Figure 7:
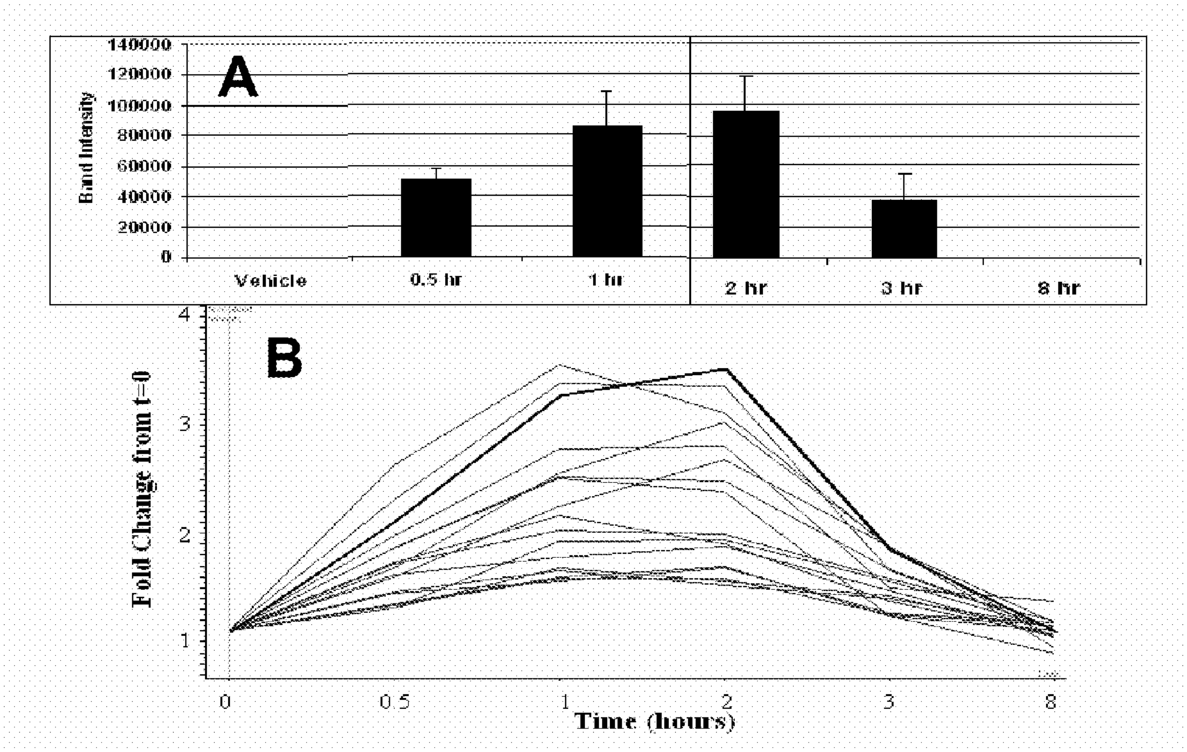
FIG. 7 (A) is an illustrative bar graph showing the time course of tubulin acetylation in peripheral blood mononuclear cells from mice treated with the HDAC inhibitor compound PCI-24781; (B) is a time course of the expression profile of genes whose mRNA levels are correlated with changes in tubulin acetylation.

A set of 16 genes (Table 5) whose expression profile in PBMC (FIG. 7A) closely tracked increases in tubulin acetylation levels (FIG. 7B) following treatment with the HDAC inhibitor PCI-24781.

TABLE 5

HDAC Inhibitor (HDACi)-Responsive Biomarker Genes

| Common | Description | Function |
|---|---|---|
| Slc9a3r1 | solute carrier family 9 isoform 3 regulator 1 | ION TRANSPORT |
| Ingl1 | inhibitor of growth family, member 1-like | CELL PROLIFERATION AND DIFFERENTIATION |
| Gadd45g | growth arrest and DNA-damage-inducible 45 gamma | CELL PROLIFERATION AND DIFFERENTIATION; APOPTOSIS |
| Plaur | urokinase plasminogen activator receptor | MULTIPLE |
| EST | RIKEN cDNA 2810405O22 gene | UNKNOWN |
| Insl6 | insulin-like 6 | BIOLOGICAL PROCESS UNKNOWN |
| Luc7l | Luc7 homolog (*S. cerevisiae*)-like | RNA PROCESSING |
| Taf9 | TAF9 RNA polymerase II | MRNA TRANSCRIPTION |
| Gadd45b | growth arrest and DNA-damage-inducible 45 beta | CELL PROLIFERATION AND DIFFERENTIATION |
| Syngr2 | synaptogyrin 2 | UNKNOWN |
| Polr2e | polymerase (RNA) II (DNA directed) polypeptide E | MRNA TRANSCRIPTION |
| Kras2 | Mouse c-Ki-ras oncogene | ONCOGENE |
| Hspa5 | heat shock 70 kD protein 5 | STRESS RESPONSE |
| Fgf15 | fibroblast growth factor 15 | CELL PROLIFERATION AND DIFFERENTIATION |
| Tuba4 | tubulin, alpha 4 | CELL STRUCTURE |
| H2afz | H2A histone family, member Z | CHROMATIN PACKAGING |

Figure 8:
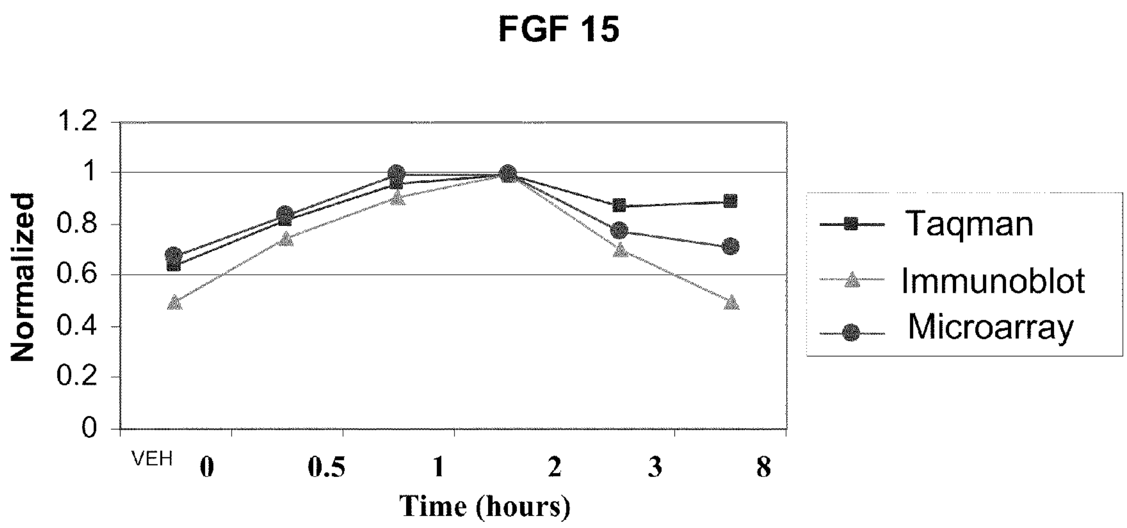
FIG. 8 is an illustrative set of two line graphs illustrating the expression profiles of two HDAC inhibitor-responsive biomarker genes as determined by microarray analysis, quantitative RT-PCR, and immunoblotting.
Figure 8:
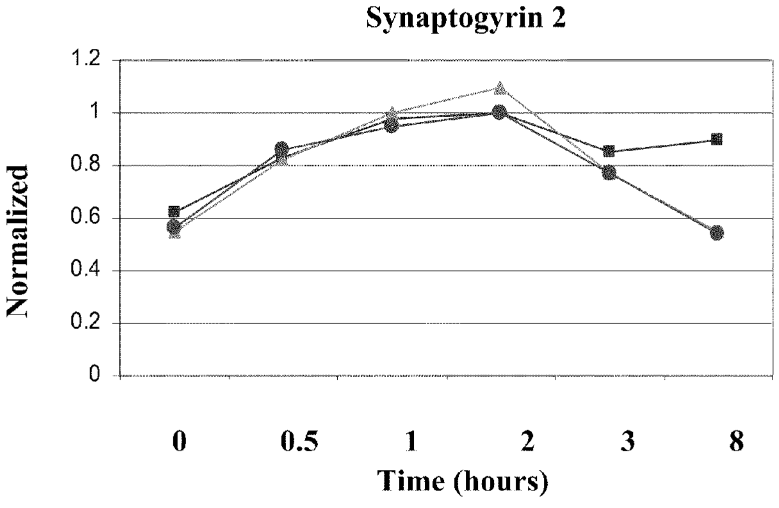

Subsequently, we validated the expression profile of two of HDACi-responsive genes, Fgf15 and Syngr2, by quantitative RT-PCR and immunoblotting. As shown in FIG. 8, the expression profiles obtained the three different methods closely matched one another, suggesting that the microarray analysis identified HDACi-responsive genes reliably.

Figure 9:
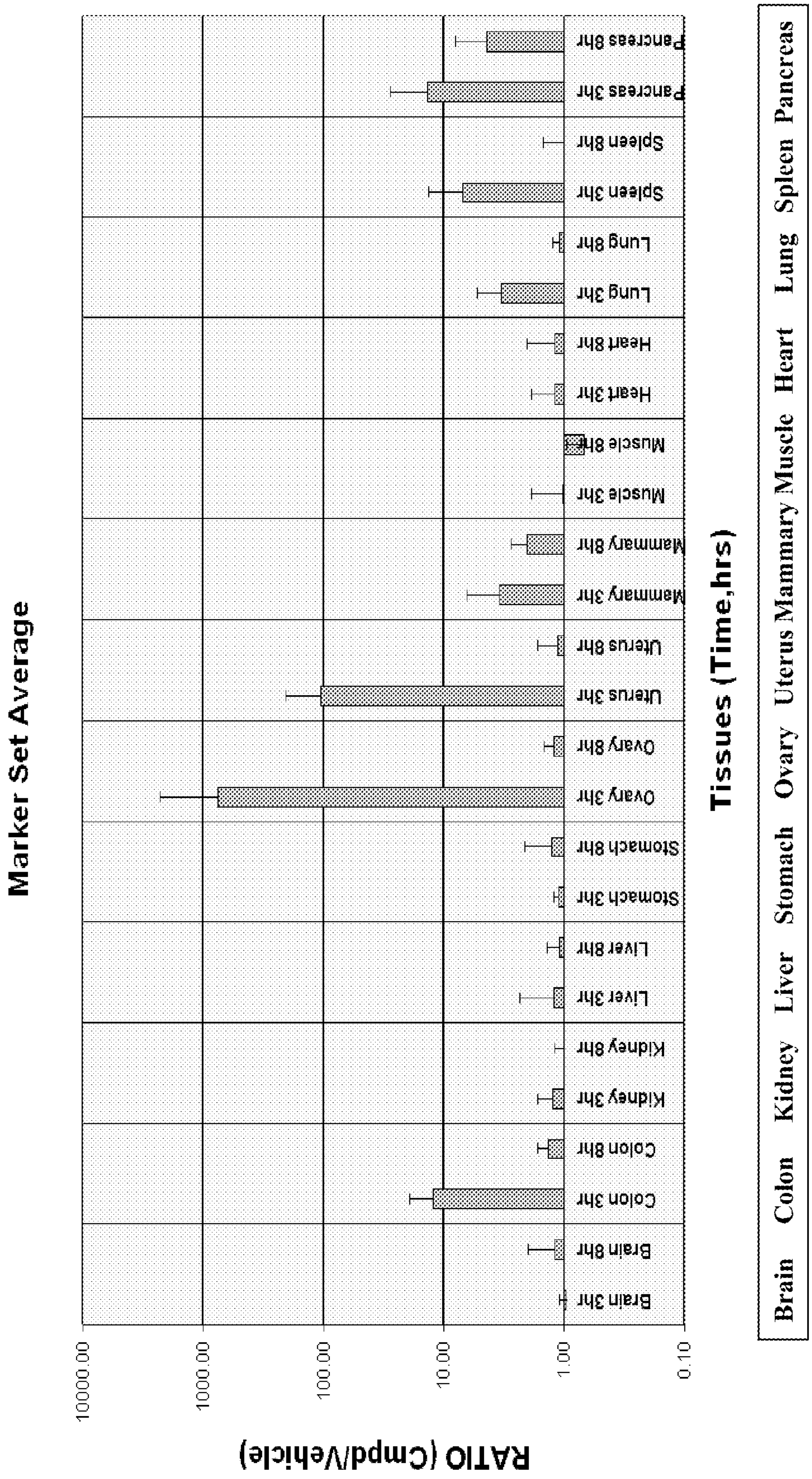
FIG. 9 is an illustrative bar graph showing average in vivo mRNA levels in various tissues of five of the HDAC inhibitor-responsive biomarker genes at 3 and 8 hours post-HDAC inhibitor treatment.

We then determined the in vivo expression levels for five of the HDACi-responsive biomarker genes in various tissues following 3 hours or 8 hours following administration of PCI-24781 (50 mg/kg). A Taqman assay was performed to determine mRNA expression levels in brain, colon, kidney, liver, stomach, ovary, uterus, mammary, muscle, heart, lung, spleen, and pancreas. The mean and SD for mRNA expression levels of all 5 genes in each tissue at each time point are shown in FIG. 9. The issue distribution pattern was very reproducible across the biomarker set. Ovary showed the highest level of induction, followed by uterus.

Figure 10:
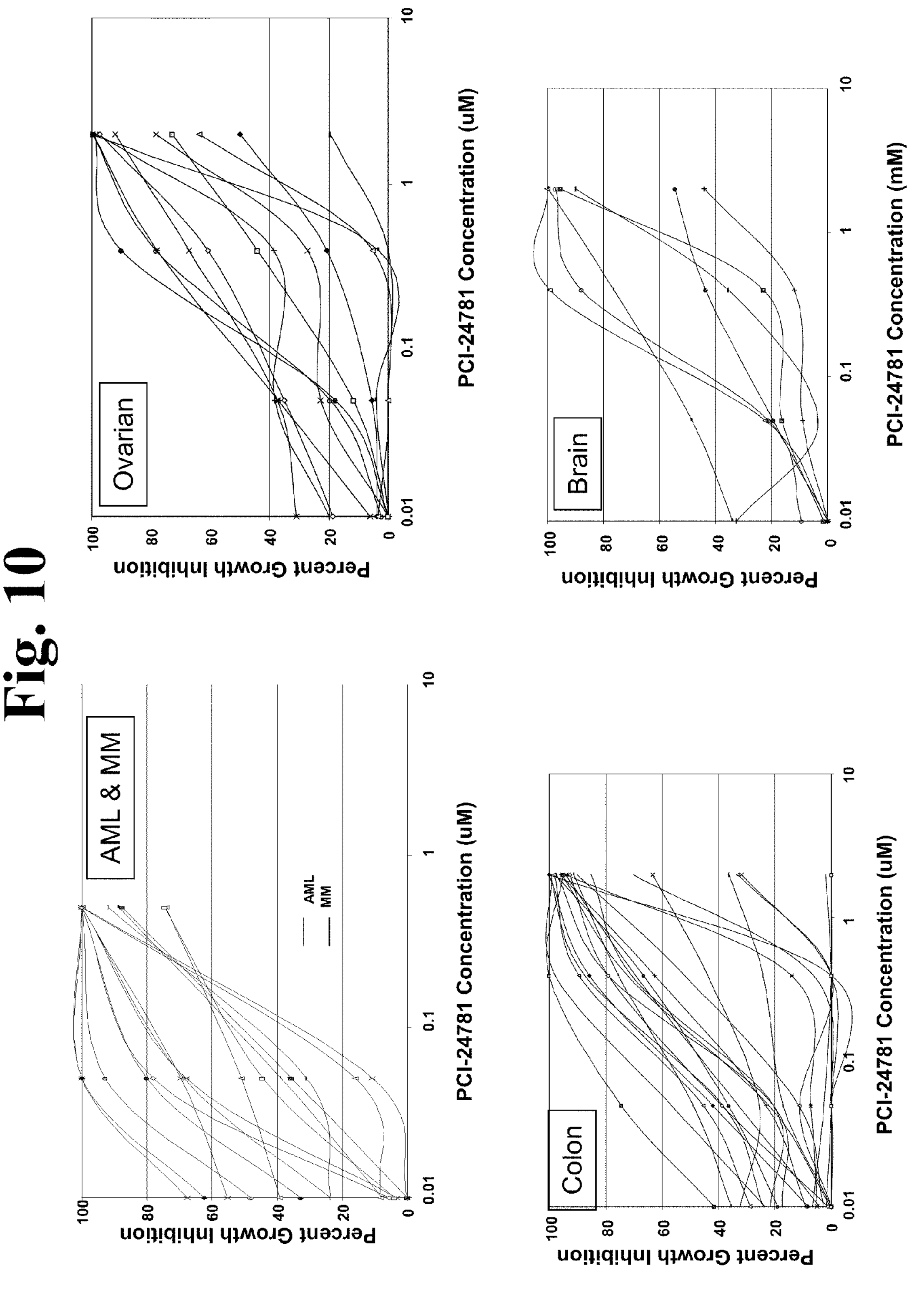
FIG. 10 is an illustrative series of dose response curves for the effect of the HDAC inhibitor PCI-24781 on tumors derived from the indicated tumors FIG. 11 (A) is a series of line graphs illustrating the amount of in vitro growth inhibition by the HDAC inhibitor PCI-24781 of primary colon tumor cells derived from newly diagnosed, naive colon cancer patients; (B) is a series of line graphs illustrating the amount of in vitro growth inhibition by the HDAC inhibitor PCI-24781 of colon cancer cells derived from patients having advanced, metastatic colon tumors; C) is a bar graph illustrating the correlation between metastatic tumor cell resistance to an HDAC inhibitor in vitro and the mRNA expression level of the HDAC resistance biomarker gene DEFA6.

Subsequently, primary human tumor samples were obtained and viable tumor cells were plated in soft agar and treated with the HDAC inhibitor PCI-24781. Tritiated thymidine was added after 3 days, and 2 days later the radioactivity incorporated into the DNA was quantified. The tumors were then classified as either resistant (EDR: Extreme Drug Resistance), sensitive (LDR) or intermediate (IDR) based on deviation from the median profile (Oncotech, Inc. Tustin, Calif.). As predicted based on the HDACi responsive biomarker gene profiles hematopoietic tumors had the lowest proportion of resistant (EDR) tumors, and colon the most (38%). See FIG. 10 and Table 6. Among the solid tumors, ovarian had the lowest proportion of resistant tumors, consistent with the high HDACi-biomarker responsiveness of this tissue.

TABLE 6

Tumor Resistance to HDAC Inhibitor PCI-24781

| Tumor Type | Resistant EDR | Intermediate IDR | Sensitive LDR | Total | % Resistance |
|---|---|---|---|---|---|
| AML | 1 | 4 | 5 | 10 | 10 |
| Multiple Myeloma | 2 | 0 | 4 | 6 | 33 |
| Ovarian | 3 | 4 | 5 | 12 | 25 |
| Glioblastoma | 2 | 1 | 4 | 7 | 29 |
| Colon | 9 | 3 | 12 | 24 | 38 |

Note:
EDR/LDR status as determined by Oncotech's algorithm from their assay data Based on the above results, we concluded that expression profiles of the orthologous human biomarkers will reflect PCI-24781 activity in human blood, and serve as PD markers in the clinic. Further, the identified set of HDACi-responsiveness biomarker genes accurately predicts tumor sensitivity to treatment with HDAC inhibitors.

What is claimed is:

1. A nucleic acid hybridization array, comprising nucleic acid probes that hybridize under high stringency hybridization conditions to a set of nucleic acids of biomarker genes comprising DEFA6, ITGB4, TM4SF3, SYK, PPAP2C, RAB25, and IL18.

2. The nucleic acid hybridization array of claim 1, further comprising nucleic acid probes that hybridize under high stringency hybridization conditions to nucleic acids of at least one biomarker gene selected from the group consisting of: HEPH, NOXO1, TM4SF4, PTPN3, EPHA2, FGFBP1, ABCC3, TPMT, DPEP1, SARG, NPDC1, CTEN, PKP3, GALNT5, CALML4, GALNT12, TPK1, EPLIN, CLIC5, PERP, SLC12A2, GUCY2C, TGFA, PTK6, EVA1, EPHA2, ITGA6, TNFRSF21, BMP4, SMPDL3B, TMPRSS2, GDA, MST1R, ITGB4, ANXA3, CCL15, NOXO1, IF127, CYP3A43, and PKP2.

3. The nucleic acid hybridization array of claim 2, wherein the nucleic acid probes hybridize under high stringency hybridization conditions to a set of nucleic acids consisting of DEFA6, ITGB4, TM4SF3, SYK, PPAP2C, RAB25, TM4SF4, and IL18.

4. The nucleic acid hybridization array of claim 1, consisting essentially of 7 to 44 nucleic acid probes that hybridize under high stringency hybridization conditions.

5. The nucleic acid hybridization array of claim 1, wherein the nucleic acid hybridization array indicates if a cancer is sensitive or resistant to an HDAC inhibitor.

6. The nucleic acid hybridization array of claim 4, wherein the nucleic acid hybridization array indicates if a cancer is sensitive or resistant to 3-((dimethylamino)methyl)-N-(2-(4-(hydroxycarbamoyl)phenoxy)ethyl)benzofuran-2-carboxamide (PCI-24781).

7. The nucleic acid hybridization array of claim 4, further comprising nucleic acid probes that hybridize under high stringency hybridization conditions to nucleic acids of at least one biomarker gene selected from the group consisting of: HEPH, NOXO1, TM4SF4, PTPN3, EPHA2, FGFBP1, ABCC3, TPMT, and DPEP1.

8. The nucleic acid hybridization array of claim 7, wherein the nucleic acid probes hybridize under high stringency hybridization conditions to a set of nucleic acids consisting of DEFA6, ITGB4, TM4SF3, SYK, PPAP2C, RAB25, IL18, HEPH, NOXO1, TM4SF4, PTPN3, EPHA2, FGFBP1, ABCC3, TPMT, and DPEP1.

* * * * *